US009958461B2

(12) United States Patent
Stagljar et al.

(10) Patent No.: US 9,958,461 B2
(45) Date of Patent: May 1, 2018

(54) DETECTION OF PROTEIN TO PROTEIN INTERACTIONS

(71) Applicant: THE GOVERNING COUNCIL OF THE UNIVERSITY OF TORONTO, Toronto (CA)

(72) Inventors: Igor Stagljar, Mississauga (CA); Julia Petschnigg, Hertfordshire (GB); Bella Groisman, Thornhill (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 24 days.

(21) Appl. No.: 14/897,048

(22) PCT Filed: Jun. 10, 2014

(86) PCT No.: PCT/CA2014/050539
§ 371 (c)(1),
(2) Date: Dec. 9, 2015

(87) PCT Pub. No.: WO2014/197986
PCT Pub. Date: Dec. 18, 2014

(65) Prior Publication Data
US 2016/0124000 A1    May 5, 2016

Related U.S. Application Data

(60) Provisional application No. 61/833,304, filed on Jun. 10, 2013.

(51) Int. Cl.
*G01N 33/74* (2006.01)
*C12N 15/10* (2006.01)

(52) U.S. Cl.
CPC ......... *G01N 33/74* (2013.01); *C12N 15/1055* (2013.01); *G01N 2333/71* (2013.01); *G01N 2500/02* (2013.01); *G01N 2500/10* (2013.01)

(58) Field of Classification Search
None
See application file for complete search history.

(56) References Cited

U.S. PATENT DOCUMENTS

2012/0230999 A1* 9/2012 Sierks ............... C07K 16/18
424/136.1

FOREIGN PATENT DOCUMENTS

EP    1348766 B1    12/2006

OTHER PUBLICATIONS

Wehrman et al. PNAS 2002 vol. 99, p. 3469-3474).*
Furman et al. (Bioorg Med Chem Lett 2009 vol. 19, p. 3748-3751).*
Bublil, E.M. et al. (2007) The EGF receptor family: spearheading a merger of signaling and therapeutics, Current Opinion in Cell Biology, 19(2): 124-134.
Da Cunha Santos, G. et al. (2011) EGFR mutations and lung cancer, Annual Review of Pathology: Mechanisms of Disease, 6:49-69.
Dünkler, A. et al. (2012) Detecting protein-protein interactions with the split-ubiquitin sensor, Bart Deplancke and Nele Gheldof (eds.), Gene Regulatory Networks: Methods and Protocols, Methods in Molecular Biology, vol. 786: 115-130.
Fields, S. et al. (1989) A novel genetic system to detect protein protein interactions, Nature, 340: 245-246.
Goh, K.I. et al. (2007) The human disease network. Proceedings of the National Academy of Sciences USA, 104(21), 8685-8690.
Johnsson, N. et al. (1994) Split ubiquitin as a sensor of protein interactions in vivo, Proceedings of the National Academy of Sciences USA, 91(22): 10340-10344.
Johnsson, N. et al. (1994) Ubiquitin-assisted dissection of protein transport across membranes, The EMBO Journal, 13(11):2686-2698.
Kolch, W. et al. (2010) Functional proteomics to dissect tyrosine kinase signalling pathways in cancer, Nature Reviews Cancer, 10(9): 618-629.
Michnick, S.W. et al. (2007) Universal strategies in research and drug discovery based on protein-fragment complementation assays, Nature Reviews Drug Discovery, 6(7): 569-582.
Pines, G. et al. (2010) Oncogenic mutant forms of EGFR: lessons in signal transduction and targets for cancer therapy, FEBS Letters, 584(12): 2699-2706.
Schulze, W.X. et al. (2005) Phosphotyrosine interactome of the ErbB-receptor kinase family, Molecular Systems Biology, 1(1):1-13.
Snider, J. et al. (2010) Detecting interactions with membrane proteins using a membrane two-hybrid assay in yeast, Nature Protocols, 5(7): 1281-1293.

(Continued)

*Primary Examiner* — Changhwa J Cheu
(74) *Attorney, Agent, or Firm* — Foley & Lardner LLP; Antoinette F. Konski

(57) ABSTRACT

The present invention relates to methods and kits for detecting the interaction between a first membrane protein and a second protein in mammalian cells as well as to identify molecules that can disrupt protein to protein interactions. The invention relies on the functional reconstitution of an active human ubiquitin by two inactive fragments upon the interaction of two proteins attached through a linker to the inactive fragments. The reconstituted ubiquitin is then cleaved by human ubiquitin proteases resulting in the release of an artificial transcription factor, which in turn activates a reporter gene transcription. Activation of the reporter gene is indicative of the interaction between the two proteins.

23 Claims, 18 Drawing Sheets

(56) References Cited

OTHER PUBLICATIONS

Stagljar, I. et al. 1998) A genetic system based on split-ubiquitin for the analysis of interactions between membrane proteins in vivo, Proceedings of the National Academy of Sciences USA, 95(9): 5187-5192.

Yarden, Y. et al. (2001) Untangling the ErbB signalling network, Nature Reviews Molecular Cell Biology, 2(2): 127-137.

* cited by examiner c d a

| | DBD | AD | activity |
|---|---|---|---|
| TF-1 | Gal4 1-147 | mNFkB 364-550 | 100% |
| TF-2 | Gal4 1-147 | mNFkB 451-550 | 38% |
| TF-3 | Gal4 1-147 | hNFkB 451-549 | 31% |
| TF-4 | Gal4 1-147 | hNFkB 521-549 | 0.3% |
| TF-5 | LexA 1-202 | VP16 413-490 | 100% |
| TF-6 | mLexA 1-202 | VP16 413-490 | 91% |
| TF-7 | mLexA 1-202 | Gal4 | 10% |
| TF-8 | mLexA 1-202 | mNFkB 364-550 | 31% |
| TF-9 | mLexA 1-202 | hNFkB 451-549 | 4% |
| TF-10 | mLexA 1-202 | VP16-dimer | 64% |
| TF-11 | mLexA 1-202 | VP16-trimer | 75% | b c

| | linker regions | activity |
|---|---|---|
| linker 1 | S-S-L-S-I-P-S-T | 45% |
| linker 2 | (G-G-G-G-S)2 | 100% |
| linker 3 | (G-G-G-G-S)3 | 97% |
| linker 4 | R-S-I-A-T | 13% |
| linker 5 | R-P-A-C-K-I-P-N-D-L-Q-K-V-M-N-H | 68% |
| linker 6 | A-A-A-N-S-S-I-D-L-I-S-V-P-V-D-S-R | 55% | d e f g

DETECTION OF PROTEIN TO PROTEIN INTERACTIONS

CROSS-REFERENCE TO RELATED APPLICATIONS

This application is a national stage application under 35 U.S.C. § 371 of International Application No. PCT/CA2014/050539, filed Jun. 10, 2014, which in turn claims priority under 35 U.S.C. § 119(e) to U.S. Provisional Application No. 61/833,304, filed Jun. 10, 2013, the content of each of which is incorporated herein by reference in its entirety.

FIELD OF THE INVENTION

The present invention is relates to novel reagents for methods for detecting protein-protein interactions with a mammalian in vivo genetic system.

BACKGROUND OF THE INVENTION

Membrane proteins play vital roles in many facets of biology and, due to their association with a variety of diseases, are of great therapeutic interest[1]. Mechanistic understanding of membrane protein function depends critically on knowledge of their physical interactions and organization into multi-protein complexes. Despite extensive research in the past decade, there is a lack of in-depth information about the various interacting partners of these integral membrane proteins, mainly due to their biochemical features, enormous complexity and multiplicity[2]. This consequently represents a major obstacle in attempts to investigate the biology of deregulation of integral membrane proteins leading to numerous human diseases such as cancer, cystic fibrosis, cardiovascular and neurodegenerative disorders and therefore also become an obstacle in designing improved targeted therapies.

To tackle the above-mentioned problems regarding the proteomic analysis of integral membrane proteins, the inventors previously developed the Membrane Yeast Two-Hybrid (MYTH) system (EP 1348766), a yeast-based technology for identification of protein interactors of integral membrane proteins from an organism of interest[3]. Since its development, MYTH has been successfully applied to study protein-protein interactions (PPIs) among various membrane proteins from yeast, plant, worm and humans[4-10].

Despite the fact that MYTH is a powerful and robust system suitable for mapping the interactions of a wide-range of membrane proteins, our extensive experience in membrane proteomics during the past 10 years has taught us that many mammalian integral membrane proteins cannot be analyzed using MYTH. A potentially significant limitation is the host organism, yeast, which is used for identifying membrane PPIs. Specifically, yeast does not carry out some of the post-translational modifications (e.g. most tyrosine-phosphorylation events as well as some glycosylation events) that are responsible for mediating PPIs between many integral membrane proteins. In addition, the composition of the yeast cellular milieu and the membrane in particular (e.g. ergosterol in place of cholesterol) is different from that in mammals, which can result in improper localization of mammalian integral membrane proteins in yeast[11]. Furthermore, a number of mammalian integral membrane proteins have been discovered to be toxic when expressed in yeast (Stagljar, I., unpublished data). Lastly, although yeast is a popular model organism for the elucidation of PPIs, it's not ideal for drug discovery purposes, such as the identification of small molecule drugs that can disrupt a PPI of therapeutic significance[12]. All of the above-mentioned facts limit our ability to detect PPIs between mammalian integral membrane proteins and their interacting partners via MYTH and prevent us of using MYTH as a drug discovery tool. Thus, successful analysis of PPIs involving mammalian integral membrane proteins requires the development of a new technology that can detect these interactions in their natural membrane environment. Such a genetic system designed in a mammalian host organism would alleviate many of the above-mentioned concerns and provide an attractive method for uncovering the biological roles of many mammalian integral membrane proteins, which cannot be studied in yeast.

Transfer of the original yeast MYTH system into mammalian cells is not trivial and it requires significant protein engineering and modification, as use of original MYTH reagents are not compatible for mammalian cells.

Accordingly, what is needed is a genetic system that can probe PPIs involving mammalian integral membrane proteins, can detect stimuli-mediated PPIs or molecules that can disrupt PPIs, can detect the phosphorylation status of proteins. These and other needs, which cannot be met by the systems of the prior art, are now met by the present invention.

SUMMARY OF THE INVENTION

In one embodiment, the present invention provides for a method for detecting the interaction between a first membrane protein or part thereof and a second membrane or soluble protein or part thereof. In one embodiment, the method includes: (a) providing a host mammalian cell including at least one detectable (reporter) gene having a binding site for a transcription factor, such that the detectable gene expresses a detectable product; (b) expressing in the host mammalian cell the first protein or part thereof, the first protein or part thereof being attached through a suitable first linker to a C-terminal sub-domain of a human ubiquitin (Cub) and a transcription factor; (c) expressing in the host mammalian cell the second protein or part thereof, the second protein or part thereof being attached to a N-terminal sub-domain of the human ubiquitin protein (Nub) through a second suitable linker; and (d) determining whether the detectable product is detected, detection of the detectable product being indicative that the first protein and the second protein interact.

In another embodiment, the present invention provides for a method for the measurement of interaction between a first membrane protein or part thereof and a second membrane or soluble protein or part thereof. The method, in one embodiment includes: (a) providing a host mammalian cell including a detectable (reporter) gene having a binding site for a transcription factor, such that the detectable gene expresses a measurable detectable product when the detectable gene is transcriptionally activated; (b) expressing in the host mammalian cell the first protein or part thereof, the first protein or part thereof being attached through a suitable first linker to a C-terminal sub-domain of a human ubiquitin (Cub) and the transcription factor; (c) expressing in the host mammalian cell the second protein or part thereof, the second protein or part thereof being attached to a N-terminal sub-domain of the human ubiquitin protein (Nub) through a second suitable linker; and (d) measuring an expression output of the detectable product as a measure of the amount of interaction between the first and the second proteins.

In one embodiment of the method for a method for the measurement of interaction between a first membrane protein or part thereof and a second membrane or soluble protein or part thereof, the expression output of the detectable product is emission of light and step (d) comprises measuring the resulting light emission as a measure of the interaction between the first and the second proteins.

In one embodiment of the methods of the present invention, step (b) comprises introducing into the mammalian host cell as part of a bait vector, a first gene under the control of a promoter, said first gene coding inter alia for the first protein or part thereof which gene is attached to the DNA-sequence of a first module encoding inter alia the Cub, the first suitable linker between the first protein and the Cub and the transcription factor.

In another embodiment of the methods of the present invention, step (c) comprises introducing into the mammalian host cell, as part of a prey vector, a second gene under the control of a promoter, the second gene coding inter alia for the second protein or part thereof which gene is attached to the DNA sequence of a second module encoding inter alia the Nub and the second suitable linker between the second protein and the Nub.

In another embodiment of the methods of the present invention, the first and second suitable linkers are substantially identical.

In another embodiment of the methods of the present invention, the second protein or part thereof is a membrane protein.

In another embodiment of the methods of the present invention, the bait vector is maintained episomally in the host mammalian cell or is integrated into the genome of the host mammalian cell.

In another embodiment of the methods of the present invention, the prey vector is maintained episomally in the host mammalian cell or is integrated into the genome of the host mammalian cell.

In another embodiment of the methods of the present invention, the first and the second linkers is a peptide comprising the amino acid sequence (GGGGS)n, wherein "n" is an integer equal to or larger than 1.

In another embodiment of the methods of the present invention, the first and the second linkers is a peptide comprising the amino acid sequence (GGGGS)n, wherein "n" is an integer equal to or larger than 2.

In another embodiment of the methods of the present invention, the transcription factor is a chimeric transcription factor selected from mLexA-VP16 and Gal4-mouseNFkB.

In another embodiment of the methods of the present invention, the human Nub is wild type.

In yet another embodiment of the methods of the present invention, the detectable gene includes a fluorescent reporter gene or a luciferase reporter gene.

In a further embodiment of the methods of the present invention, the detectable product is selected from firefly luciferase and green fluorescent protein (GFP).

In another embodiment, the present invention relates to a kit of reagents for detecting binding between a first membrane protein or part thereof and a second membrane or soluble protein or part thereof. The kit, according to one embodiment, includes: (a) a host cell including at least one detectable (reporter) gene having a binding site for a transcription factor, such that the detectable gene expresses a detectable product when the detectable gene is transcriptionally activated; (b) a first vector (bait) comprising a first site that can receive a first nucleic acid coding for the first protein or part thereof such that when the first nucleic acid is inserted it becomes attached to the DNA sequence of a first module encoding inter alia a C-terminal sub-domain of a human ubiquitin protein (Cub), a first suitable linker between the first protein and the Cub, the first module further comprising a nucleic acid for the transcription factor, and a promoter; (c) a second vector (prey) comprising a second site that can receive a second nucleic acid coding for the second protein or part thereof such that when the second nucleic acid is inserted it becomes attached to the DNA sequence of a second module encoding inter alia a N-terminal sub-domain of the human ubiquitin protein (Nub) and a second suitable linker between the second protein and the Nub, wherein the second module further comprises a promoter.

In one embodiment of the kit, the first and second suitable linkers are substantially identical.

In another embodiment of the kit, the second protein or part thereof is a membrane protein.

In another embodiment of the kit, the bait vector is maintained episomally in the host mammalian cell or is integrated into the genome of the host mammalian cell.

In another embodiment of the kit, the prey vector is maintained episomally in the host mammalian cell or is integrated into the genome of the host mammalian cell.

In another embodiment of the kit, the first and the second linkers is a peptide comprising the amino acid sequence (GGGGS)n, wherein "n" is an integer equal to or larger than 1.

In another embodiment of the kit of the present invention, the first and the second linkers is a peptide comprising the amino acid sequence (GGGGS)n, wherein "n" is an integer equal to or larger than 2.

In another embodiment of the kit, the transcription factor is a chimeric transcription factor selected from mLexA-VP16 and Gal4-mouseNFkB.

In yet another embodiment of the kit of the present invention, the human Nub is wild type.

In yet another embodiment of the kit of the present invention, the first membrane protein or part thereof and the second membrane or soluble protein or part thereof are mammalian proteins.

In a further embodiment of the kit of the present invention, the detectable product is selected from firefly luciferase and GFP.

In another embodiment, the present invention provides for a method of identifying a potentially pharmaceutically active agent. The method, in one embodiment, includes using the kit of the previous embodiments to screen an agent for the ability to interfere with protein-protein interaction, whereupon the ability to interfere with protein-protein interaction is indicative of the agent being potentially pharmaceutically active.

The present invention, in another embodiment, provides for a method for providing a compound(s) that can interfere with protein-protein interaction. The method, in one embodiment, includes: (a) providing a mammalian host cell having the prey vector and the bait vector of the present invention, the first and second proteins or parts therefore being selected such that they are known to interact when expressed; (b) incubating the host cell in the presence and absence of the compound(s) to be tested; (c) measuring the difference in reporter gene expression between the incubation containing the compound(s) to be tested and the incubation free of the compound(s) to be tested; and optionally (d) purifying or synthesizing the compound that can interfere with protein-protein interaction.

In another embodiment, the present invention provides for novel and inventive interactors of the epidermal growth factor receptor (EGFR). The intereactor, in one embodiment, is selected from the group consisting of the proteins expressed by the genes SOCS6, GRAP2, STAT2, CD33, S100A4, TP53, ARRB1, Rgs4, APP, ICP2, TNS3, SHC4, ARRB2, LRP1, MAPK9, FRK, CDC25C, HDAC7, MAP3K3, WASF3, MAPK8, BAIAP2, PTPN18, YWHAB, WASL, FASLG, MED28, SH2D3C, MAPT, SNCA, CDH5, SNX9, PRKCE, YWHAG, TAB1, HCK, SH3GL3, RELA, REPGEF1, TNFRSF1A, NR3C1, IKBKG, PIM1, RAF1, AKT1, CTTN, LAT, NTRK2, ASAP2, CD3E, STAP2, ACTN4, TRAF2, RET, ITK, FGR, PRKCZ, ITGB2, ITSN2, and PTPN22.

In another embodiment, the present invention relates to a use of a kit of the present invention in a screening process for identifying pharmaceutical drugs.

In another embodiment, the present invention relates to a use of a kit of the present invention in screening the phosphorylation status of the first or second proteins.

In yet a further embodiment of the methods and kits of the present invention, the first and/or the second protein is/are toxic to yeast; or the first and/or second proteins require post-translational modifications that are not carried out by yeast.

Further and other objects of the invention will be realized from the following Summary of the Invention, the Discussion of the Invention and the embodiments and Examples thereof.

BRIEF DESCRIPTION OF THE DRAWINGS

Embodiments will now be described, by way of example only, with reference to the drawings, in which.

DETAILED DESCRIPTION OF THE INVENTION

Definitions

Figure 1:
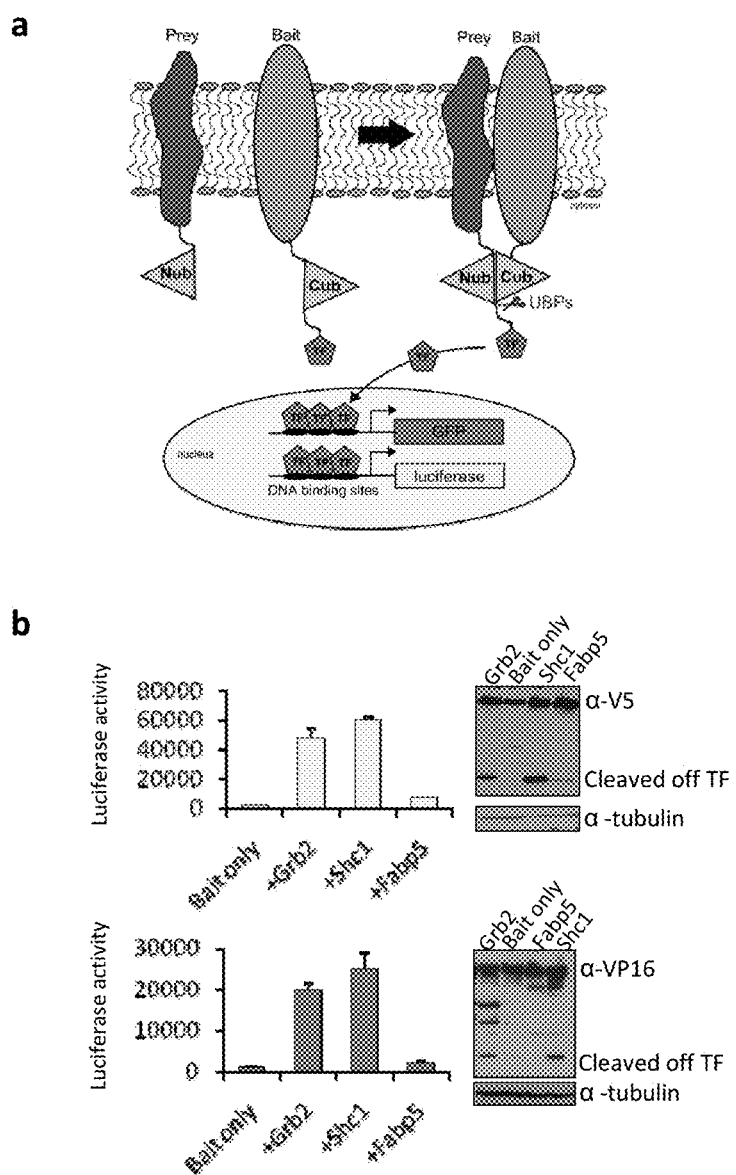
FIG. 1 illustrates a set-up and validation of a mammalian membrane two-hybrid (MaMTH) system in accordance to one embodiment of the present invention. Panel (a) is a graph illustrating the MaMTH system of the present invention. Panel (b) illustrates stable 5×GAL4UAS-luciferase (top) and 8×lexA-ops-luciferase HEK293T (bottom) reporter cells assessed for their performance in MaMTH. Panel (c) are microphotograhs illustrating plasma membrane localization of ErB-baits tagged with Cub-GFP-mLexA-VP16; scale bar=10 µM. Panel (d) are graphs illustrating the validation of MaMTH using EGFR (bottom graph) and ErbB4 (top graph) baits tested against known interactors (Shc1, Grb2, Hsp90) and negative control preys.
Figure 1:
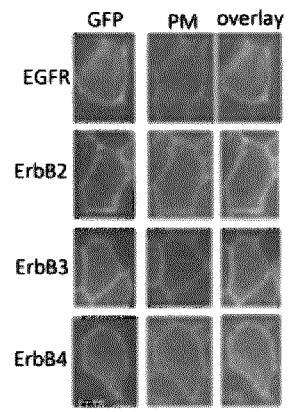
Figure 1:
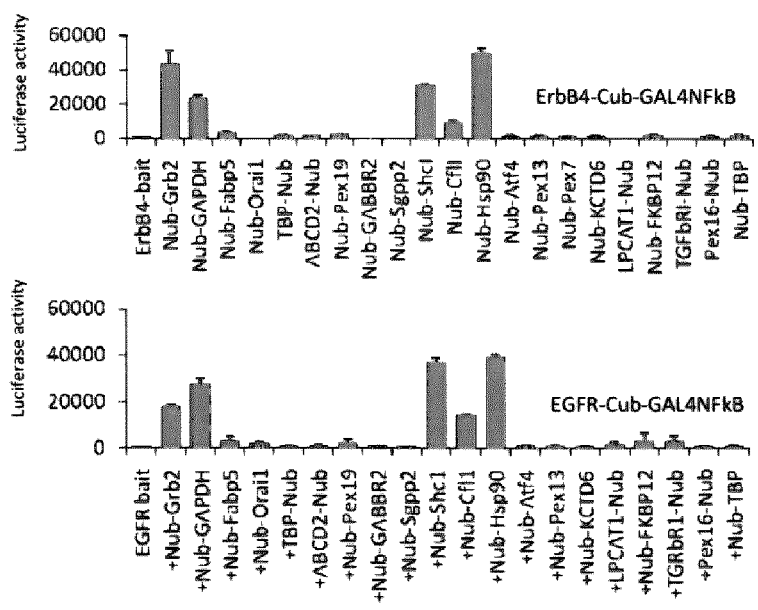

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided. All publications cited in this document and the priority document are incorporated herein by reference.

The term "Nub" as used herein refers to the N-terminal portion of human ubiquitin, which encompasses amino acids 1-37 of human ubiquitin. "Nub" contains either the amino acids 1-37 of wild type human ubiquitin, or the amino acids 1-37 of mutated ubiquitin. For example, "NubI" refers to a wild type form of Nub. "NubV is a mutated form of NubI, in which the amino acid isoleucine at position 13 has been changed for a valine.

The term "Cub" is used to refer to the C-terminal portion of human ubiquitin, which encompasses amino acids 35-76 of human ubiquitin.

The term "bait" as used in this document defines a fusion of a polypeptide and one or more other polypeptides, one of which is a first protein sequence involved in intracellular protein degradation such as Cub. The bait can be used in the mammalian membrane two-hybrid (MaMTH) system of the present invention to investigate interactions between said bait and one or several preys.

The term "bait vector" as used in this document refers to a nucleic acid construct which contains sequences encoding the "bait" and regulatory sequences that are necessary for the transcription and translation of the encoded sequences by the host cell, and preferably regulatory sequences that are needed for the propagation of the nucleic acid construct in mammalian cells. Preferably the "bait vector" also encodes the activator of the host reporter gene(s).

The term "prey" as used in this document defines a fusion between a polypeptide and one or more other polypeptides, one of which is a second protein sequence involved in intracellular protein degradation such as Nub. Nub may be either wild type Nub (NubI) or a mutated version of Nub, where one or several of its amino acids have been replaced by other amino acids, as described in detail for "Nub" above.

The terms "prey vector" and "library vector" as used herein refer to a nucleic acid construct which contains sequences encoding the "prey" and regulatory sequences that are necessary for the transcription and translation of the encoded sequences encoding by the host cell, and preferably regulatory sequences that are needed for the propagation of the nucleic acid construct in E. coli.

The term "Split-ubiquitin" as used herein refers to quasi-native human ubiquitin assembled from non-covalently linked Nub and Cub, which have been brought into close spatial proximity by the interaction of two unrelated polypetides that are fused to Cub and Nub respectively. Split-ubiquitin is recognized by ubiquitin-specific proteases present in the mammalian cell, which attack the polypeptide chain C-terminal to the double glycine motif in Cub. The proteolytic cleavage leads to the breakage of the polypeptide chain after the double glycine motif.

The term "transactivator polypeptide" or "activator" as used in this document refers to any polypeptide that possesses the ability to activate the "reporter gene" of the host cell, e.g. by recruiting and activating the RNA Polymerase II machinery of mammalian cell.

The term "mLexA" as used in this document refers to the nucleic acid sequence encoding the bacterial repressor protein LexA or its translation product, where the sequence may either encode the wild type LexA sequence or a mutated LexA ("mLexA") sequence where the amino acid arginine at position 157 has been replaced by a glycine or where the amino acid arginine at position 159 has been replaced by glutamate or glycine, or any combination of the two mutations.

The term Gal1-147 used in this document refers to the nucleic acid sequence encoding the yeast protein Gal4, corresponding to amino acids 1-147 of its translation product.

The term "artificial transcription factor" or "chimeric transcription factor" as used in this document refers to a hybrid protein including (1) a polypeptide with the intrinsic ability to bind to a defined nucleic acid sequence, such as the bacterial repressor protein LexA or the yeast Gal4 protein or the and (2) any transactivator polypeptide, as defined above (VP16 and mouseNFkB)

The term "TDA" as used in this document refers to a nucleic acid sequence or its translation product, comprising the following elements: (1) an epitope tag which allows the immunological detection of the polypeptide by means of an antibody directed specifically against the epitope, such as V5 tag, HA tag, 3×FLAG tag, (2) an artificial transcription factor.

The term "reporter cell line" as used in this document refers to any host cell that includes at least one "reporter gene" such as any cell line that includes nucleic acid constructs, either integrated into its genome, or as autonomously replicating elements, that produce a signal upon activation by the activator, e.g. by activation of reporter genes such as firefly luciferase or green fluorescent protein (GFP).

The term "reporter gene" as used in this document refers to a nucleic acid sequence comprising the following elements: (1) a binding site for an artificial transcription factor, (2) a minimal promoter sequence (TATA box sequence) (3) a nucleic acid sequence encoding for firefly luciferase or GFP (4) a polyA tail for transcriptional termination.

Overview

The present invention relates to a novel split-ubiquitin based two-hybrid approach that can serve as a much needed solution in the field of proteomics and drug discovery to address the difficult challenge of studying protein-protein interactions (PPIs) in mammalian cells, including PPIs involving full-length integral membrane proteins under various conditions. The novel approach of the present invention, termed Mammalian Membrane Two-Hybrid system (MaMTH) is an inventive improvement of the original membrane yeast two-hybrid system (MYTH). Major differences between MYTH and MaMTH include: (a) use of a wild-type, N-terminal fragment of human ubiquitin (Nub) in contrast to the mutant yeast NubG used in MYTH; (b) specially designed linkers added to bait and prey MaMTH vectors in order to obtain a measurable interaction using a positive control set of known interactors, and (c) the use of fluorescent reporter genes and luciferase reporter, which provides substantially different read-out than the growth selection used in MYTH. While MYTH assay provides readout in yes/no form (whether there is an interaction or not), the methods of the present invention may also provide a quantitative approach enabling accurate measurement of the amount of PPI, such as strength and affinity.

MaMTH may detect transcriptional activation of a reporter gene such as firefly luciferase or GFP located downstream of multiple Gal4- or lexAops-DNA-binding sites. The integral membrane protein-linker-Cub-TF (GAL4 DNA binding domain (DBD) and NFkB activation domain (AD) or mLexA-DBD and VP16-AD) bait and membrane and/or cytosolic protein-linker-Nub-prey may be co-transfected or infected with a lentivirus carrying cDNAs encoding these two proteins into a mammalian cell line stably expressing the above-mentioned reporter genes. If the bait and prey interact, ubiquitin reconstitution may occur, leading to the proteolytic cleavage by UBPs (ubiquitin-specific proteases present in the host cell), and the subsequent release of the transcription factor (TF). The TF may then enter the nucleus resulting in reporter gene activation.

Figure 6:
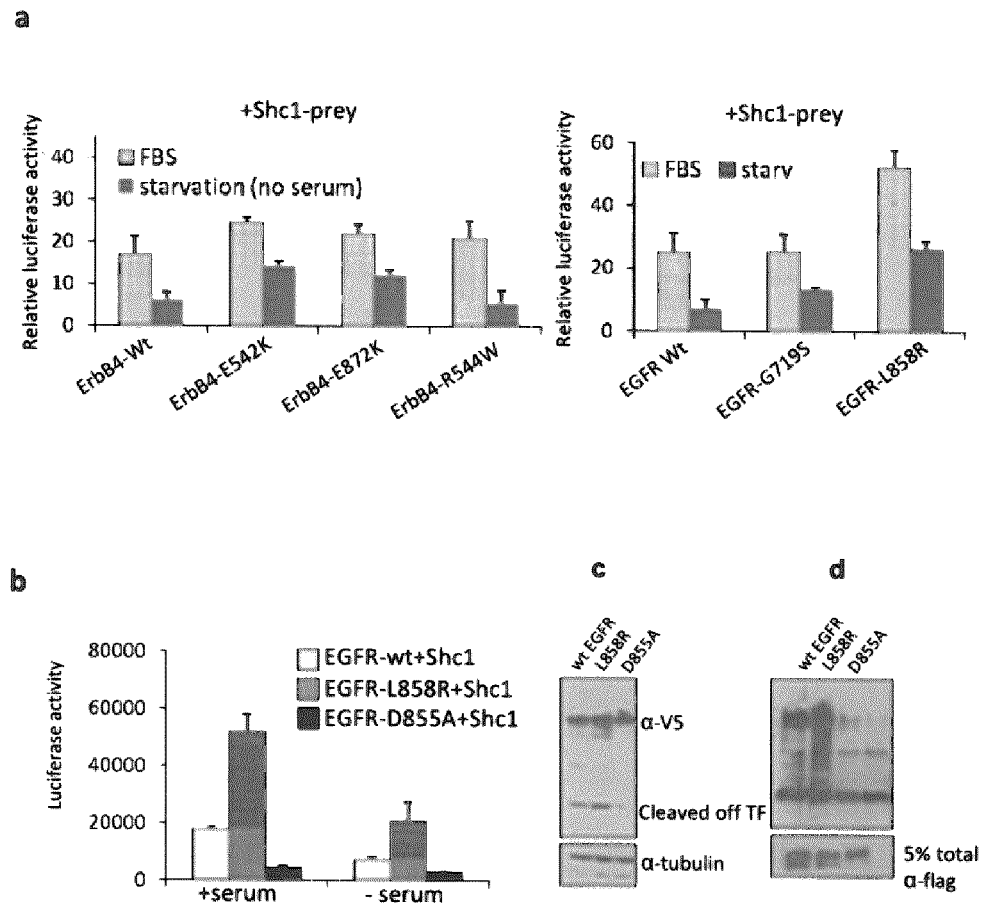
FIG. 6 Graphs illustrating the monitoring of phosphorylation-dependent interactions of oncogenic ErbB family members. (a) Left panel: Relative luciferase activity of stable 5×GAL4UAS-HEK293T luciferase reporter cells co-transfected with various oncogenic ErbB baits and Shc1 prey. (a) Right panel: Relative luciferase activity of stable 5×GAL4UAS-HEK293T luciferase reporter cells co-transfected with oncogenic EGFR variants (L858R and G719S). (b) Luciferase activity of sable 5×GAL4UAS-HEK293T luciferase reporter cells co-transfected with EGFR-Wt, EGFR-L858R or EGFR-D855A-kinase dead baits and Shc1 adaptor prey. (c)-(d) Western Blot showing expression of various receptors using anti-V5 antibodies and phosphor-tyrosine-specific antibodies. (e) Graph illustrating change in luciferase activity of stable 5×GAL4UAS-luciferase HEK293T reporter cells co-transfected with EGFR-Wt, EGFR-L858R or EGFR-exon19del and Shc1 prey at different concentrations of Erlotinib. (f) Graph comparing change in luciferase activity of EGFR-L858R, EGFR-exon19del and the erlotinib-resistant mutant EGFR-L858R/T790A compared to EGFR-Wt in respect to Shc1-binding upon erlotinib treatment. (g) Graph illustrating luciferase activity of stable 5×GAL4UAS-luciferase HEK293T reporter cells transfected with EGFR-Wt, EGFR-L858R, EGFR-exon19del and EGFR-L858R/T790M and tested for Shc1-binding in serum-containing media without Erlotinib. (h) Western Blot analysis of EGFR-Wt, EGFR-L858R, EGFR-exon19de and EGFR-L858R/T790A baits transfected into stable5×GAL4UAS-luciferase HEK293T reporter cells in serum-containing media. After transfection, Erlotinib was added at indicated concentrations and cells were lysed after treatment and Western Blot analysis was performed using anti-EGFR and anti-phospho-EGFR antibodies.
Figure 6:
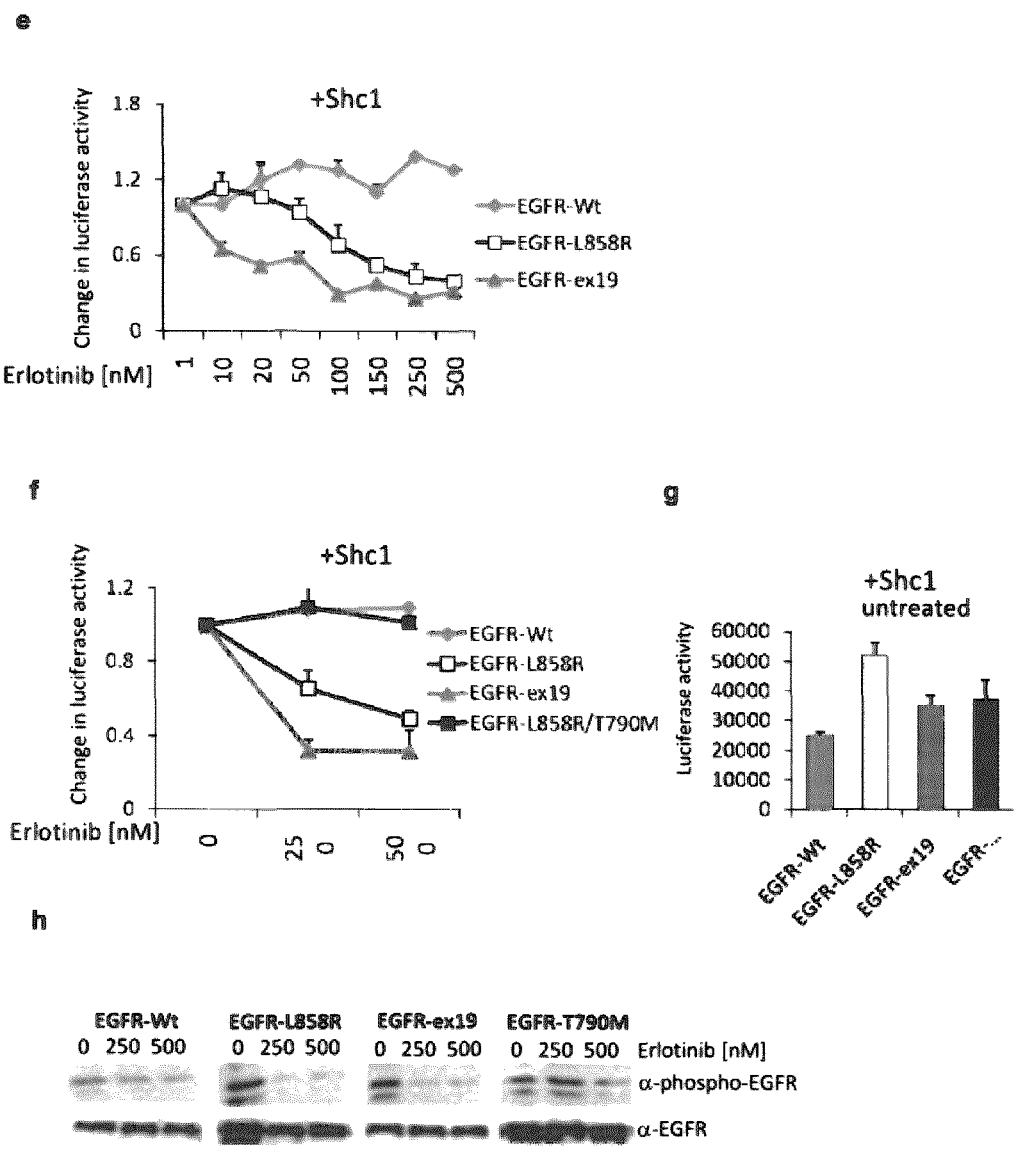
Figure 9:
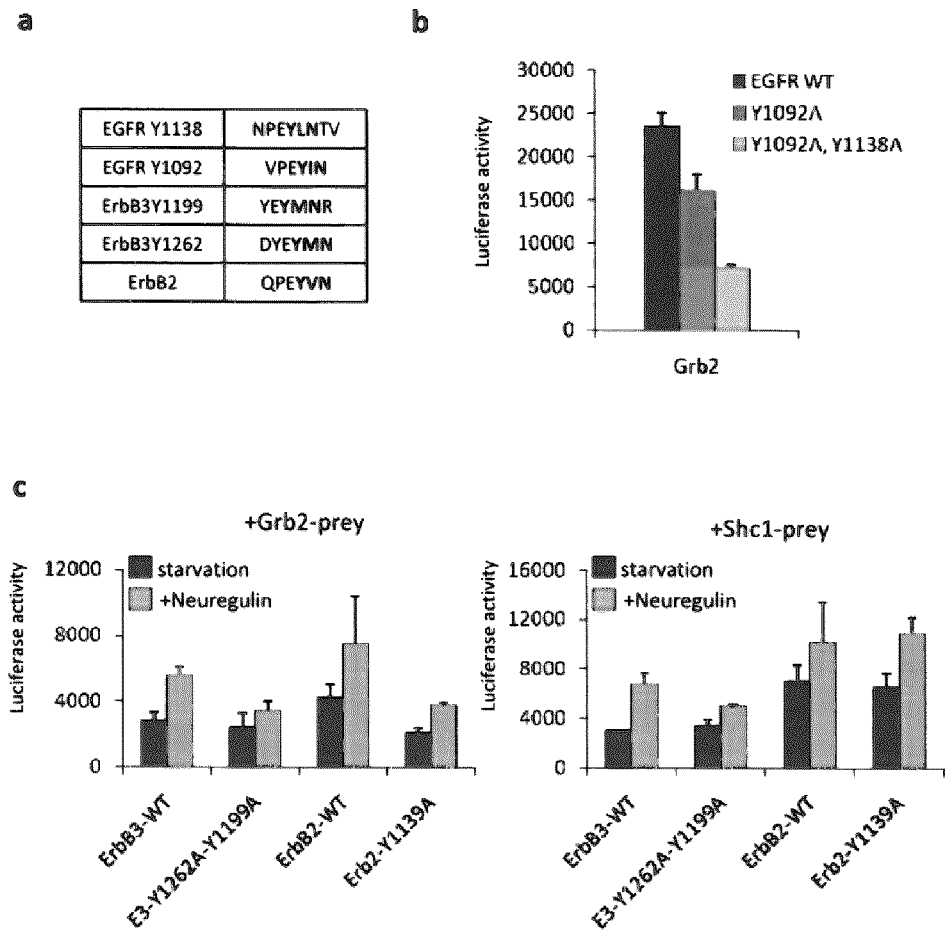
FIG. 9 MaMTH allows sensitive detection of PPIs that utilize Y—X—N Grb2 binding site in ErbB family members. (a) List of ErbB family phospho-mutants generated implicated in Grb2-binding. (b) Graph illustrating luciferase activity of stable 5×GAL4UAS-luciferase reporter cells co-transfected with either EGFR-Wt or Y-p mutants (Y1092A or Y1092, Y1138A) baits with Grb2. Luciferase activity was measured 24 h following transfection. EGFR-Y1092A, Y1138A shows decreased binding with Grb2 adaptor. (c) Graph illustrating ErbB2/Grb2 and ErbB3/Grb2 ligand-dependent interaction. Following overnight starvation cells transiently expressing ErbB3 or ErbB2 baits (Wt or mutated in specific Y-residues) were treated with 10 ng/ml Neuregulin for 4 h, followed by measuring luciferase activity. Significant ErbB3/Grb2- or ErbB2/Grb2-association upon ligand binding was inhibited by introducing two point mutations into Grb2 binding sites. (d) Graph illustrating ErbB2/Shc1 and ErbB3/Shc1 ligand-dependent interaction. Shc1 recruitment was not affected in ErbB2-Y1139A upon ligand binding.

As shown in FIG. 6 (a), the methods of the present invention provide for detection of slight changes in the phosphorylation state of ErbB WT and oncogenic mutants, measured by recruitment of the adaptor protein Shc1. FIG. 6 (d) shows that interaction between EGFRL858R and Shc1 may be inhibited in dose-dependent manner by treatment with the tyrosine-kinase inhibitor erlotinib. FIG. 9 (b) illustrates the additive effect of the double versus single mutation on Grb2 recruitment to EGFR.

Applications (1) PPIs MaMTH May be Used as a High-Throughput Screening Technology for the Identification of PPI of Human Integral Membrane Proteins.

In addition to generating the basic set of bait/prey/reporter reagents, MaMTH is sensitive enough to detect subtle changes in protein interactions, which can differ slightly depending on the presence or absence of various stimuli, like hormones or agonists, or inhibitory drugs. For example, MaMTH may detect the phosphorylation status of oncogenic ErbB receptors through direct measurement of adaptor protein recruitment.

(2) Drug Screening Platform

MaMTH may be used to monitor the interactions of inhibitors or enhancers with mammalian integral membrane proteins. As such, MaMTH may be used as a drug screening platform suitable for the identification of small molecule inhibitors or enhancers that alter a defined set of membrane protein interactions in their natural environment. MaMTH may, for example, be used to monitor drug-inhibited (Erlotinib) interactions of mutated EGFR-receptors, such as EGFR-L858R and EGFR-exon19-deletion, as well as increased adaptor protein binding in the Erlotinib-resistant mutant EGFR-L858R/T790M15.

Using MaMTH as a screening tool, 61 previously unknown interactors of both EGFR-wild type and the oncogenic version EGFR-L858R have been detected, the latter being primarily found in non-small cell lung cancer (NSCLC) patients [15] and highlight that MaMTH allows for the establishment of dynamic interaction patterns of a given human receptor. MaMTH is a genetic assay, which may be applied to test interactors of any membrane proteins under various conditions. Moreover, stable expression of all MaMTH components, like bait/prey/reporter, through lentiviral integration may allow for using the system in virtually any cell line, and decreases overexpression artifacts due to low-copy integration.

As such, the present invention provides for a method for studying or detecting interactions in a mammalian cell setting between a first (membrane or soluble) protein and a second (membrane or soluble) protein. In one embodiment, the method may include: (a) providing a host mammalian cell including at least one detectable gene (reporter gene (firefly luciferase, GFP and so forth)) having a binding site for a transcription factor, such that the detectable gene expresses a detectable product when the detectable gene is transcriptionally activated; (b) expressing in the host mammalian cell the first protein or part thereof, the first protein or part thereof being attached through a suitable first linker to a C-terminal sub-domain of a human ubiquitin (Cub) and the transcription factor; (c) expressing in the host mammalian cell the second protein or part thereof, the second protein or part thereof being attached to a N-terminal sub-domain of the human ubiquitin protein (Nub) through a second suitable linker; and (d) determining whether the detectable product is detected, detection of the detectable product being indicative that the first protein and the second protein interact.

The interaction between the expressed first and second proteins and/or their parts may lead to an interaction of the Nub and the Cub which interaction in turn leads to activation of an intracellular protease and proteolytic separation of the transcription factor, wherein both the bait vector and the prey vector are suitable for being maintained episomally or integrated into the genome.

In another embodiment, the present invention provides for a kit of reagents for detecting binding between a first protein (membrane bound or soluble) or part thereof and a second protein or part thereof (membrane bound or soluble). The kit, in one embodiment, may include: (a) a host cell containing at least one reporter gene (firefly luciferase or GFP and so forth) having a binding site for a transcription factor, such that the detectable gene expresses a detectable product when the detectable gene is transcriptionally activated; (b) a first vector (bait), which may be maintained episomally or integrated into the genome of the host mammalian cell, comprising a first site for receiving a first nucleic acid coding for a first membrane protein or part thereof such that when the first nucleic acid is inserted it becomes attached to the DNA sequence of a first module encoding inter alia a C-terminal sub-domain of a human ubiquitin protein (Cub) and a first suitable linker between the first membrane protein and the Cub, the first module further comprising a nucleic acid for a transcription factor, and a promoter; (c) a second vector (prey), which may be maintained episomally or integrated into the genome of the host cell, comprising a second site for receiving a second nucleic acid coding for a second membrane protein or a soluble protein or part thereof such that when the second nucleic acid is inserted it becomes attached to the DNA sequence of a second module encoding inter alia a N-terminal sub-domain of the human ubiquitin protein (Nub) and a second suitable linker between the second membrane protein and the Nub, wherein the second module further comprises a promoter. In one aspect, the kit further includes (d) a plasmid library encoding second proteins or parts thereof. In another aspect, the baits containing the transcription factor comprises a mutated form of LexA (mLexA) and VP16 or GAL4-mouseNFkB.

Advantages

The system of the present invention presents several advantages over existing techniques to study interactors of membrane proteins, including MYTH: (i) MaMTH can be carried out in virtually any cell line due to the availability of prey/bait/reporter vectors for lentivirus generation, which poses the advantage of single copy integration and diminishes overexpression artifacts. Moreover, MaMTH is carried out in living cells, thus avoiding signal changes arising from cell lysis or protein purification used in biochemical PPI methods; (ii) MaMTH is compatible with the Gateway-recombinatorial cloning technique, allowing for a fast and easy cloning procedure into all vector backbones; (iii) MaMTH can detect subtle changes in interaction patterns, which can be induced/repressed by either drugs, various stimuli or phosphorylation events, in a highly specific manner; (iv) the sensitivity and flexibility of MaMTH makes it amenable for upscaling to high-throughput formats; (v) MaMTH can be used as a platform for drug discovery, specifically used to screen for novel compounds capable of inhibiting signaling mediated by oncogenic receptors; (vi) unlike the MYTH assay, MaMTH may be used in quantitative studies to measure the strength or affinity of PPI.

In order to aid in the understanding and preparation of the present invention, the following illustrative, non-limiting examples are provided.

EXAMPLES

Materials and Methods

Bait, Prey and Reporter Plasmid Construction

Table 5 shows a complete list of plasmid backbones used in this study. Table 6 shows primers used to generate reporters, baits and preys.

Gateway-compatible entry clones: Entry clones were obtained by the human ORFeome library v8.1[49] or PCR-amplified from Mammalian Gene Collection clones to create entry clones in pDONR223 using Gateway BP cloning technology (Invitrogen) according to the manufacturer's protocol. Entry clones were sequence-verified.

Mammalian membrane two-hybrid (MaMTH) reporter vectors: Lentiviral reporter constructs were constructed using pLD-Gateway-Puro-NVF (kind gift of Kim Blakely and Jason Moffat) as a backbone, which was cut with BstBI and KpnI to remove the Puromycin marker. The cPPT-hPGK-Hygro-resistance marker cassette (amplified from pLD-hygro-EcMV, kind gift of Kim Blakely and Jason Moffat) was PCR-amplified with flanking BstBI/KpnI sites and ligated into the cut vector. The resulting vector was cut with SanDI and SalI and the insert 5×GAL4UAS-TATA-box-luciferase (PCR-amplified from template pFR-Luc, Stratagene) was ligated into the vector. The resulting 5×GAL4UAS-TATA-box-luciferase-hygromycin-plasmid was cut with SanDI and BamHI to replace the 5×GAL4UAS-sites with 8×lexAops-sites (PCR-amplified from plasmid L8-Luc[50]). 5×GAL4UAS-TATA-box-luciferase-hygromycinR and 8×lexAops-TATA-box-luciferase-hygromycinR-plasmids were then used to excise luciferase and clone eGFP into BamHI/SalI sites (eGFP was amplified from template pLJM1). Final constructs were sequence-verified.

MaMTH-bait and prey destination vectors: Bait and prey destination vectors were generated using standard restriction digest and T4 ligation protocols. Combinations of Cub-transcription factor inserts were generated by homologous recombination in yeast: briefly, regions of Cub, DNA-binding domain and transciprital activation domain were PCR-amplified (for templates see below) with overhangs complementary to either the yeast vector backbone pCCW-Ste or the adjacent inserts. pCCW-Ste was cut with NotI/FspI and up to 3 inserts (Cub, DBD, AD) were co-transformed into yeast BY4742 using standard Lithium acetate transformation[51]. Recombined constructs were then sequenced and the inserts "Cub-TF" were PCR-amplified containing 1) linker regions and 2) restriction sites suitable for cloning the tags into mammalian vector backbones to generate final destination vectors. Final bait destination vectors are based on pGateway-CMV5'-tripleFLAG or pGateway-CMV3'-tripleFLAG (kind gifts of Jason Moffat's lab), and the tags "linker-Cub-mLexA-VP16" or "linker-Cub-GAL4-mNFkB" were cloned into XbaI sites of pGateway-CMV5'-tripleFLAG to obtain MaMTH bait destination vectors for C-terminal tagging. Final prey destination vectors are also based on pGateway-CMV5'-tripleFLAG or pGateway-CMV3'-tripleFLAG, and linker-tripleFLAG-Nub were cloned into XbaI site of pGateway-CMV5'-tripleFLAG to obtain MaMTH prey vectors for C-terminal tagging or Kozak-Nub-tripleFLAG-linker was cloned into KpnI/HindIII sites of pGateway-CMV3'-tripleFLAG to obtain MaMTH prey vectors for N-terminal tagging. Lentiviral prey backbones were based on pLD-Gateway-Puro-CVF and pLD-Gateway-Puro-NVF (kind gifts of Kim Blakely and Jason Moffat), and linker-tripleFLAG-Nub was cloned into EcoRV/BstBI sites of pLD-Gateway-Puro-CVF to obtain MaMTH lentiviral prey destination vectors for C-terminal tagging or Kozak-Nub-tripleFLAG-linker was cloned into EcoRV/NheI sites of pLD-Gateway-Puro-NVF to obtain MaMTH lentiviral prey destination vectors for N-terminal tagging.

Prey linker regions were introduced by incorporating linkers into primers. C-terminal ubiquitin (aa 35-76) and N-terminal ubiquitin (aa 1-37) was PCR-amplified from yeast genomic DNA (for yCub and yNubi) or from human ubiquitin-cDNA (for hCub and hNubi). Regions after yCub or hCub was amplified from MYTH-TMBValpha and contains a 5'-ATG (ATGcacagatcagcttgcggccgc) to ensure that the cleaved off transcription factor is not degraded according to the N-end rule (REF). Variants of either yNubi or hNubi were generated using site-directed mutagenesis protocols (Stratagene).

All MaMTH bait and prey destination vectors were fully sequenced and expression clones (after LR reaction of entry clones with the respective destination vectors) were sequenced at the junctions between bait- or prey-tags and cDNAs. Bait and prey expression vectors are all created using Invitrogen LR cloning technology using entry clones mentioned above and self-designed destination vectors.

Figure 2:
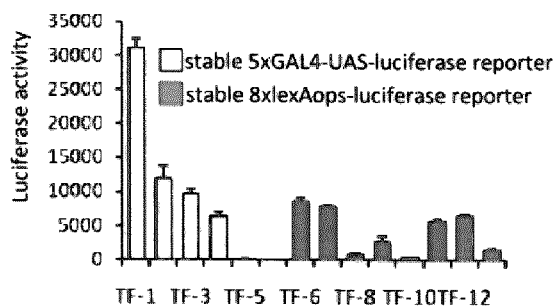
FIG. 2: (a) List of various combinations of chimeric transcription factors consisting of a DNA-binding domain (DBD) and a transcriptional activation domain (AD) that were tested. (b) Graph illustrating luciferase activity of combinations of full-length transcription factors transfected into either stable 5×GAL4-UAS-luciferase or stable 8×lexA-ops-luciferase HEK293T cell lines. Luciferase activity was measured 48 h after transfection. The combinations of GAL4-DBD (amino acid 1-147) and mNFkB-AD (amino acids 364-550) for 5×GAL4-AUS-luciferase cells (=TF-1) and mLexA-DBD (amino acids 1-202) and VP16-AD (amino acids 413-490) for 8×lexA-ops-luciferase cells (TF-6) were incorporated into bait constructs due to best luciferase activity compared to the negative controls (the reason for choosing TF-6 over TF-5 is explained in FIG. 1e). The TF that gave highest signals in either 5×GAL4-UAS-luciferase or stable 8×lexA-ops-luciferase stable reporter cells were set to 100%. (c) List of various linker regions between the C- or N-terminal halves of ubiquitin and the cDNA portion were cloned into both ErbB4 bait and Grb2 prey vectors. (d) Graph illustrating the linker regions of FIG. 2 (c) assayed for reporter gene activation in 5×GAL4UAS-luciferase stable cell lines 48 h after transfection. The linker that gave highest interaction signal for ErbB4-Grb2 control was set to 100%. (e) Graph illustrating the luciferase activity of human and yeast versions of Cub and Nub cloned into ErbB4-bait and Grb2-prey vectors using various versions of Nub that display different affinities for Cub (f) Graph illustrating luciferase activity using ErbB4 bait tagged with either Cub-LexA-VP16 or Cub-mLexA-VP16, which has an additional mutation in the putative nuclear localization sequence of LexA31. (g) Graphs illustrating the final bait, prey and reporter set-ups.
Figure 2:
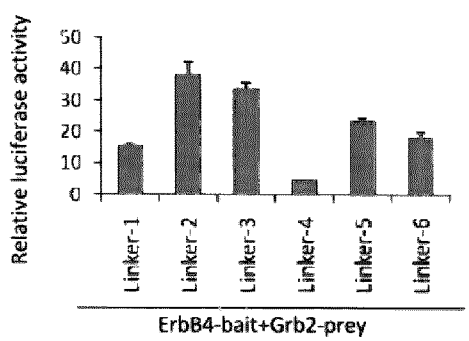
Figure 2:
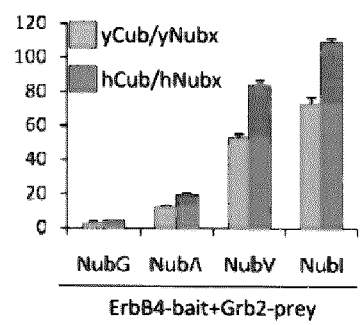
Figure 2:
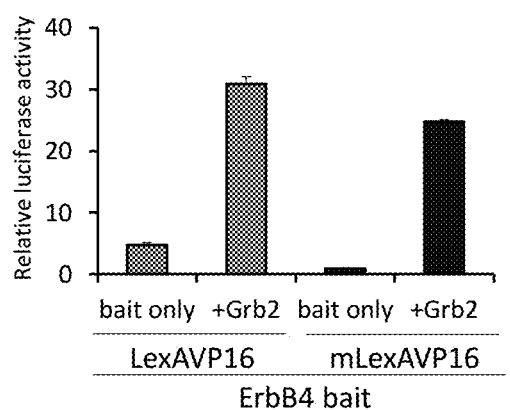
Figure 2:
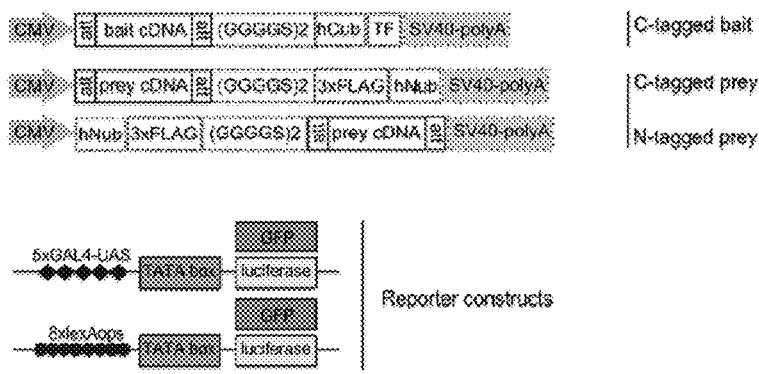

MaMTH-vectors for testing performance: Chimeric transcription factors used in FIG. 2 (a) were PCR-amplified from mouse-RELA-cDNA (mNFkB), human RELA-cDNA (hNFkB), GAL4-DBD (pDEST32 Invitrogen), MYTH-vectors pTMBValpha (LexA and VP16) and pNIA E432 #40 (mLexA[31]) and standard restriction digests and T4-ligation were performed. Chimeric transcription factors were ligated into pGateway-CMV3'-tripleFLAG cut with KpnI and XbaI, where the Gateway cassette was taken out.

Mutants of ErbB family members and β2-AR were generated by site-directed mutagenesis and sequence-verified in full. GFP-constructs for bait localization were constructed by homologous recombination in yeast (final inserts Cub-GFP-mLexAVP16 or Cub-GFP-GAL4-NFkB) and then PCR-amplified with XbaI-restriction sites and ligated into pGateway-CMV5'-tripleFLAG cut with XbaI to generate C-terminally tagged bait-GFP destination vectors.

Lentivirus Generation

Lentiviral reporter or prey plasmids were co-transfected with psPAX2 and pMD2 into HEK293T cells using X-tremeGene9 transfection reagent (Roche) and Optimem-serum-reduced media (Gibco) 18 h after transfection, media was removed and replaced by viral harvesting media (DMEM+1.1 g/100 mL BSA). 24 h later, the first viral harvest was performed and high-BSA harvesting media added to the cells. Again after 24 h, the second harvest was done and combined with the first harvest and virus was stored at −80° C. Lentiviral work was carried out in accordance with all Biosafety requirements.

Stable Cell Line Generation

Lentiviral titers were assayed and target cells are infected at a multiplicity of infection between 0.3-0.5. 24 h after infection, cells were selected with puromycin (2 µg/ml for HEK293T, 1.5 µg/ml for HCC827, H226, H3255) in case of infection with preys, overexpression constructs or shRNAs for at least 48 h and expanded or frozen down for further assays. In case of infection with reporter constructs, cells were selected with hygromycin (100 µg/ml for HEK293T) for at least 7-10 days, and single cells were isolated by limited dilution. Briefly, stable reporter cells were seeded into 96-well plates that on average each well contains 1 cell. About 7 days later, colonies were expanded and assayed for reporter gene activation. Clones that gave high luciferase signal upon transfection with full-length transcription factors compared to negative controls were expanded and used for further experiments. Double bait/reporter double stable cell lines were generated through transfection, as bait-lentiviral constructs exceeded the lentiviral packaging limit and gave low virus titer. MaMTH-baits were co-transfected with a linear puromarker (Clontech) at a ratio 20:1 and selected in puromycin (2 µg/ml) 48 h after transfection for about 7 days. Single colonies were isolated using sterile cylinders and tested for bait expression by Western blot.

Cell Culture

HEK293T cells were cultured in Dulbecco's modified Eagle's medium (DMEM) with 10% fetal bovine serum and 1% antibiotics (penicillin/streptomycin). Lung cancer cell lines HCC827, H3255 and H226 were maintained in RPMI-1640 supplemented with 10% fetal bovine serum and antibiotics. Starvation conditions were performed in DMEM or RPMI without FBS or with 0.1% FBS. Erlotinib (kind gift of Dr. Ming Tsao) was added at indicated concentrations and agonist isoproterenol (Sigma-Aldrich) was added at a concentration of 10 μM.

Transfection Experiments

Transfection experiments were performed using a modified calcium phosphate method. Briefly, for a 12-well plate, 65 μl ddH$_2$O and 75 μl 2×BES (N,N-bis(2-hydroxyethyl)-2-aminoethanesulfonic acid) was added to DNA and 7.5 μl 2.5M CaCl$_2$ was then added and the tubes vortexed and incubated at room temperature and added dropwise to the cells. 8-16 h later, the transfection mix was removed and replaced with media.

Luciferase Reporter Assay

Firefly luciferase activity was measured as follows: infected or transfected reporter cells were lysed between 20 h (for drug treatments) or 48 h after transfection (expression analysis) or 4 days after infection. Wells were washed with PBS and Promega reporter lysis buffer (1×) plus protease inhibitor (Complete-EDTA-Roche) was added. Plates were frozen at −80° C. to ensure complete lysis. Luciferase activity was measured at least from three independent experiments. Cell lysates were then measured on an injectable Berthold luminometer suitable for 96-wells plates.

MaMTH EGFR-interactor Screen 206 top-predicted EGFR-interactors were cloned into lentiviral prey backbones. After lentivirus harvest, target cells (stable 5×GAL4UAS-luciferase reporter-HEK293T cells) were infected at a multiplicity of infection (MOI) of around 0.3-0.4 to ensure single copy integration per cell. Cells were selected in puromycin for at least 48 h and transfected with either EGFR-wildtype or EGFR-L858R baits in triplicates. 24 h after transfection, cells were lysed and luciferase assays performed. On each set of interaction assays, various negative controls were included. To calculate a MaMTH-interaction scores, negative controls were averaged and the fold-change of luciferase activity compared to the averaged controls was calculated and defined as the interaction score.

Thus, interaction score values above 1 can be considered as interactors.

MaMTH Interaction Score

Each set of experiments contains a defined set of negative controls in at least three replicates. Negative controls were chosen as such that there is a range of controls showing high-background luciferase activity (normally cytosolic proteins: Fabp5, Pex19) as well as medium-background luciferase activity (membrane-bound interactors: Pex7, GABBR2). Negative controls were averaged and the fold-change of luciferase activity was calculated. Using this method, we have a stringent cut-off and chose an interaction score >1 to be interacting proteins.

Antibodies and Western Blot Analysis

Western blot analysis was performed using standard protocols. Briefly, cells were either directly harvested in 2×sample buffer or harvested in 1×reporter lysis buffer (Promega) containing protease inhibitors (Complete-EDTA, Roche) and 2×sample buffer was added after freezing the cells at −80° C. For phospho-specific antibodies, cells were lysed in Ripa buffer containing Na-orthovanadate, PMSF and protease inhibitor and 2×SB was added and samples were immediately boiled at 95° C. for 5 min and proceeded for Western Blot analysis. 5-10% of the lysates were separated by 10% SDS-PGE gels and transferred to nitrocellulose membranes. Transferred samples were immunoblotted with primary antibodies, followed by incubation with HRP-coupled secondary antibodies, and detection was performed using GE-Healthcare enhanced luminescence. A list of antibodies used can be found in Table 7.

LUMIER Assay

HEK293T cells were transfected in 96-well plates with EGFR-Renilla or EGFR-L858R-Renilla fusion constructs together with 60 selected 3×Flag-tagged bait plasmids. One day after transfection, normal growth medium (DMEM+ 10% FBS) was replaced by low serum medium (DMEM+ 0.1% FBS) for 16 h. Cells were treated with 100 ng/ml EGF or left untreated for 15 minutes before cell lysis. LUMIER assay was performed as described previously 35, except that interactions were not normalized to the bait protein abundance. LUMIER was performed in duplicates in three independent rounds. Significant interactors were based on p-values after t-test calculations compared to corresponding backgrounds.

Fluorescence Microscopy

Bait constructs (harboring Cub-GFP-mLexA-VP16) were transfected into stable 8×lexAops-luciferase cells seeded on poly-L-lysine-coated glass slips. 48 h after transfection, fluorescence microscopy was performed on a Leica DMI 6000 B using GFP and RFP channels. Cells were washed with warm PBS and covered in 5 μg/ml Invitrogen CellMask Deep Purple dye for 5 min at 37° C. Cells were washed 3 times with warm PBS and immediately used for microscopy. Cells were examined at 63× magnification using a Leica DMI 6000 B microscope with GFP, Texas Red and differential interference contrast filters. Images were analyzed using the Volocity software.

Results

Development of MaMTH

The MaMTH of the present invention is an improvement of PCA (protein fragment-complementation assay)[16]. Briefly, a membrane "bait" protein is tagged with the C-terminal half of human ubiquitin (Cub), a linker and a chimeric transcription factor (TF), and the prey, which can be either cytosolic or membrane-bound, is coupled to the N-terminal half of human ubiquitin (Nub) through a linker. Only upon interaction of the bait and prey, the split-halves form functional ubiquitin, which is then recognized by cytosolic deubiqitinating enzymes (DUBs), resulting in cleavage of the transcription factor and subsequent reporter gene expression (luciferase or GFP, FIG. 1a). Substantial inventive improvement and protein engineering had to be performed to transfer the original yeast MYTH to mammalian cells (FIG. 2a-e). First, stable HEK293T reporter cell lines (having either integrated 8×LexA-binding sites or 5×Gal4-binding sites) were generated by lentiviral infection, and clones were tested for either GFP or luciferase expression. Suitable transcription factors (TF) 18-26 using either LexA-DNA binding domain (DBD) or GAL4-DBD and tested various combinations for reporter gene activation in both 8×lex-Aops-luciferase and 5×GAL4UAS-luciferase stable cell lines. Transcription factors consisting of GAL4 (1-147)-DBD and mNFkB (364-550)-activation domain (AD) and mLexA (modified LexA 1-202)-DBD and VP16 (413-490)-AD were incorporated into final bait constructs as they showed highest luciferase induction upon transfection into reporter cells (FIG. 2a). Negative controls (either DBD domain or AD domain alone) were also transfected to rule out sponanteous reporter gene activation without full-length transcription factor (data not shown). Every "bait" protein used in this study was tested with both TF-set-ups and shows comparable results with both. Furthermore, various linker regions (either used in other PCAs or MYTH[7, 13, 16]) were tested between the bait/prey cDNAs and the ubiquitin portions (either Cub or Nub). Unexpectedly, it was found that linkers influenced the reconstitution of the split-halves (as tested for reconstitution of the known interaction between ErbB4 and Grb2). As shown in FIG. 2d the flexible glycine-serine-hinges $(GGGGS)_2$ or $(GGGGS)_3$ gave a high luciferase signal suggesting that a certain steric flexibility may be required for optimal pseudo-ubiquitin reconstitution. The flexible glycine-serine hinge $(GGGGS)_2$ was chosen for final bait and prey set-ups, as this linker showed highest luciferase signal upon co-transfection of ErbB4 and Grb2 into stable luciferase reporter cells (FIG. 2d). It should be understood that $(GGGS)_n$, where "n" is an integer equal to or larger than 1 may also be used.

MYTH either uses NubI[27] or NubG (Ile13Gly) in prey constructs, which is a stringent mutation causing less affinity of Cub to Nub[12, 28]. Interestingly, as illustrated in FIG. 2e, in MaMTH, NubG does not lead to significant luciferase activity upon ErbB4-bait/Grb2-prey co-transfection, suggesting that NubG is too stringent to be used in mammalian cells, which could be due to different DUB-specificity and abundance in yeast and humans[29, 30]. Thus, less stringent variants of Nub like NubA and NubV as well as the wild-type version NubI were incorporated into Grb2-prey and tested against ErbB4-bait. NubG has least affinity for Cub, followed by NubA and NubV, and NubI is the wildtype version The various versions of Nub were included into Grb2 preys. Bait and prey were co-transfected into 5×GAL4UAS-luciferase stable cell lines and 48 h later, luciferase activity was measured. Luciferase ratios were calculated based on the fold-change of luciferase activity over averaged negative controls.

As shown in FIG. 2e, both yeast and human versions of ubiquitin are recognized by UBPs in human cells, though, human Nub and Cub display about 15% higher luciferase signal. Grb2-preys containing either NubI or NubV show high interaction signal upon co-transfection with ErbB4 bait, whereas NubA and NubG show low signal in MaMTH.

NubV and NubI gave the highest ErbB4-Grb2 interaction signals, and NubI was subsequently chosen to be incorporated into prey vectors (FIG. 2e). Moreover, though yeast and human ubiquitin only differs in 3 amino acids, both variants were incorporated into ErbB4-bait and Grb2-prey. Human NubX and Cub showed increased affinity for each other compared to yeast variants, resulting in increased luciferase activity of ErbB4-Grb2 interaction (FIG. 2e). Thus, human Cub and Nub versions were included into final bait and prey vectors.

Finally, in contrast to MYTH, which uses LexA-VP16 in all bait constructs, we incorporated a mutated form of LexA $(mLexA^{31})$ into bait constructs, which abolishes an NLS-like signal sequence and thus shows less background activation when the bait only is transfected into reporter cells (FIG. 2f). As shown in FIG. 2f, transfection of ErbB4-LexA-VP16 bait alone into 8×lexAops-luciferase stable cells resulted in background luciferase activity, suggesting that part of the baits is transferred to the nucleus via the putative NLS sequence. Using ErbB4-mLexA-VP16 bait decreased self-activation and was thus chosen to be included into final bait constructs. As a positive control, the known interactor Grb2 was co-transfected with ErbB4, showing that mutation of LexA to mLexA has only minor effects on the interaction assay. FIG. 2g shows the final set-up of bait, prey and reporter constructs used for MaMTH. MaMTH baits are normally C-tagged, whereas both versions of preys (N-tagged and C-tagged) exist. All bait and prey constructs are Gateway-compatible, allowing for easy cloning, and contain a (GGGGS)2-linker. Baits can be used in both GAL4-NFkB set-up as well as mLexA-VP16 set-up, which should be determined on a case by case basis. Reporter HEK293T cells stably express either 5×GAL4UAS-luciferase/GFP or 8×lexAops-luciferase/GFP.

MaMTH Performance and Validation

Figure 3:
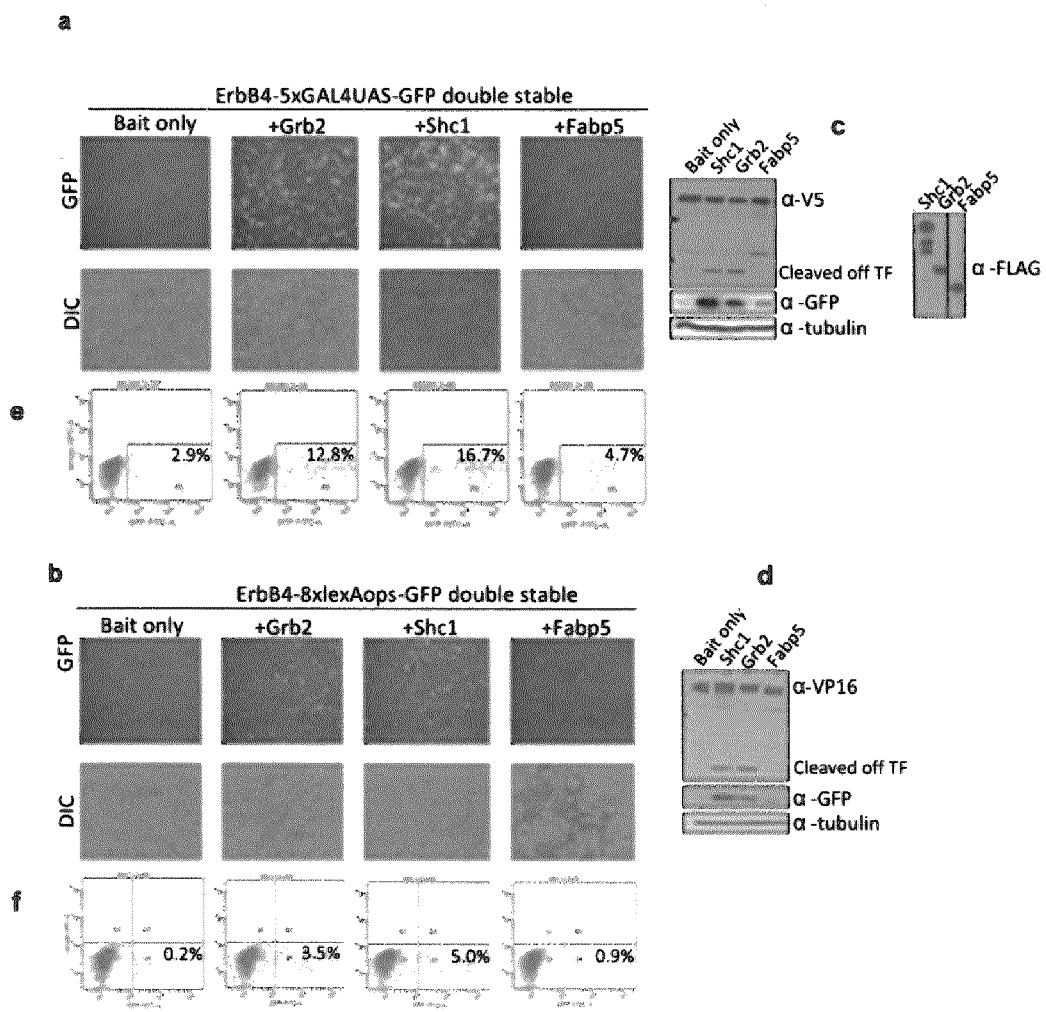
FIG. 3: Microphotographs illustrating the performance of stable (a) 5×GAL4UAS-GFP or (b) 8×lexA-ops-GFP HEK293T reporter cells in MaMTH. Known interaction between ErbB4 and Grb2 or Shc1 can be detected in both transcription factor set-ups, whereas the negative control (Fabp5) and bait alone are close to background. (c)-(d) Western blot illustrating reporter gene activation due to the cleaved off TFs using either VP16 antibody (for baits with mLexA-VP16-TF; panel (d)) or V5 antibody (for baits with GAL4-NfKB-TF; panel (c)). Note that ErbB4-Cub-GAL4-NFkB displays higher background activity in the bait only control due to increased self-activation. (e)-(f) FACS profiles show the percentage of GFP-positive population from each interaction pair.

Induction of reporter gene expression was assessed for both stable GFP and luciferase reporters (in both 5×GAL4-UAS and 8×lexAops-set ups). Double stable ErbB4-reporter cell lines were infected with Shc1 or Grb2 (positive controls) or Fabp5 (negative control) or not infected (to test for self-activation of the bait) and both GFP and luciferase activity were assessed (FIG. 1b, FIG. 3). MaMTH is shown to be highly specific and can detect ErbB4-Grb2/Shc1 interactions in all set-ups tested. Reporter gene activation correlates with the cleaved off transcription factor, which we monitored by Western blot. Baits harboring GAL4-NFKB transcription factor show higher fluorescence as well as luciferase activity, but show slightly more background with the negative control (FIG. 1b, FIG. 3). FIG. 1b illustrates that known interaction between ErbB4 and Grb2 or Shc1 can be detected in both transcription factor set-ups, whereas the negative control (Fabp5) and bait alone are close to background. Reporter gene activation due to the cleaved off TFs can also be followed by Western Blot using either VP16 antibody (for baits with mLexA-VP16-TF) or V5 antibody (for baits with GAL4-NfKB-TF). Overall, both GFP and luciferase reporters can be used in MaMTH, but subtle changes in interactions may be better defined using luciferase activity than GFP and thus, further experiments were all performed using luciferase reporters.

Figure 5:
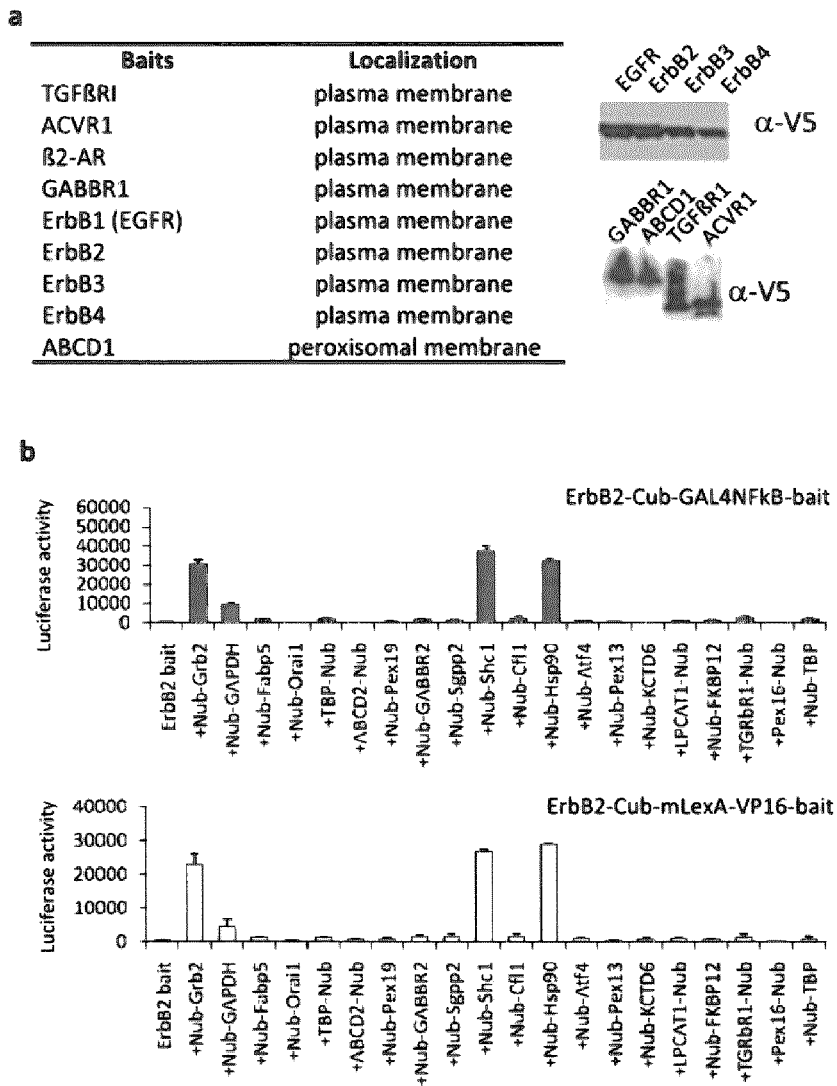
FIG. 5: (a) Western blot analysis of the proteins shown in the table tagged with either Cub-mLexA-VP16 or Cub-GAL4-mNFkB and used for interaction studies. Expression was tested for both transcription factor set-ups, only bait-Cub-GAL4-mNFkB is shown. (b) Graphs illustrating luciferase activity of ErbB2/luciferase-double stable cells (in both transcription factor set-ups) infected with the indicated preys; luciferase assays were performed 4 days after infection. (c) Graphs illustrating luciferase activity of ErbB4 or EGFR-Cub-mLexAVP16-luciferase-double stable cells infected with indicated preys; luciferase assays were performed 4 days after infection. (d) Graphs illustrating luciferase activity of stable 5×GAL4UAS- or 8×lexAops-luciferase reporter cells co-transfected with either GABBR1 baits (top two graphs) or TGFbR1 (bottom two graphs) and indicated preys; luciferase activity assayed 48 h after transfection. (e) Graphs illustrating luciferase activity of stable 5×GAL4UAS-luciferase reporter cells co-transfected with either ACBD1, ErbB3 or ACVR1 baits and indicated preys; assayed for luciferase activity 48 h after transfection.
Figure 5:
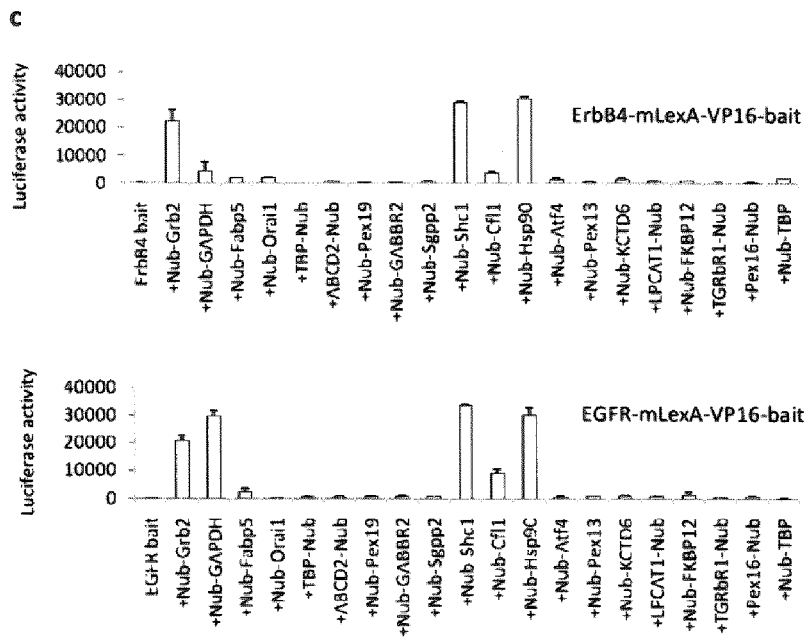
Figure 5:
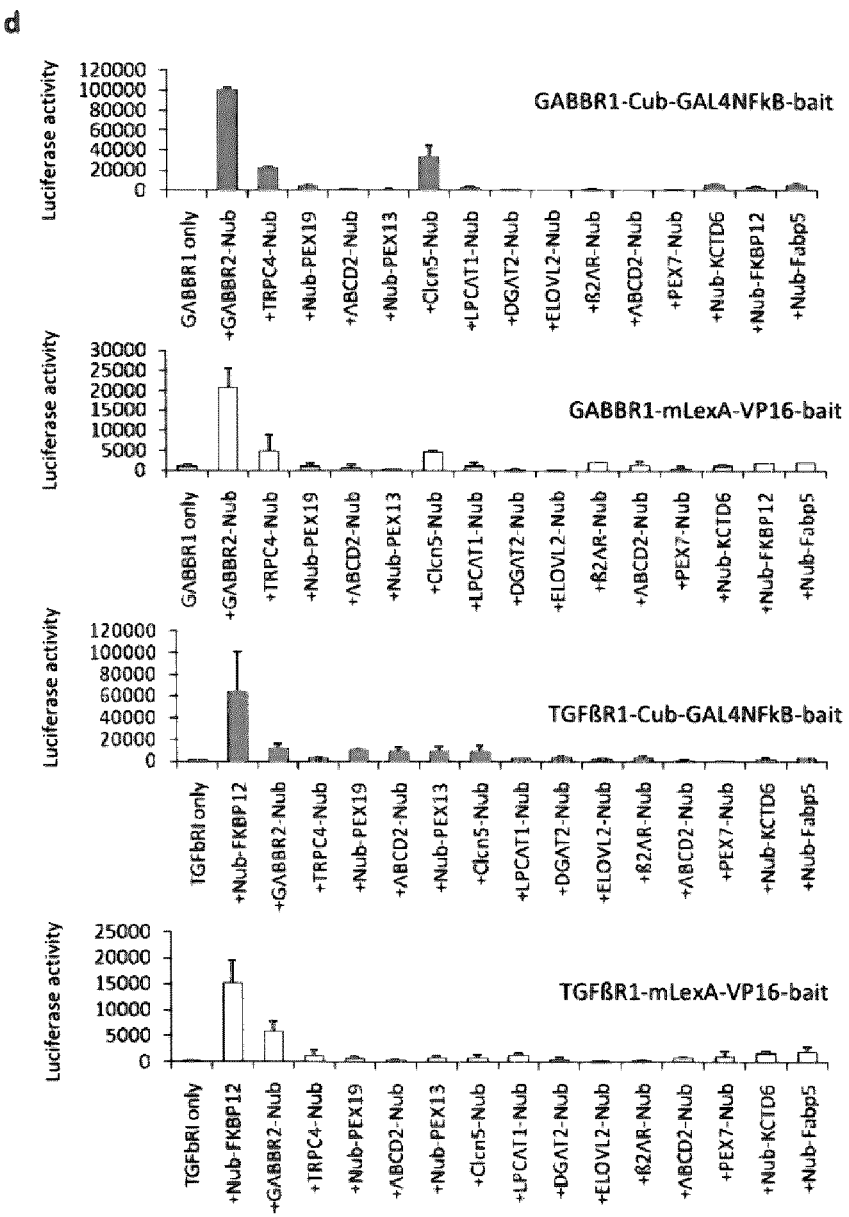
Figure 5:
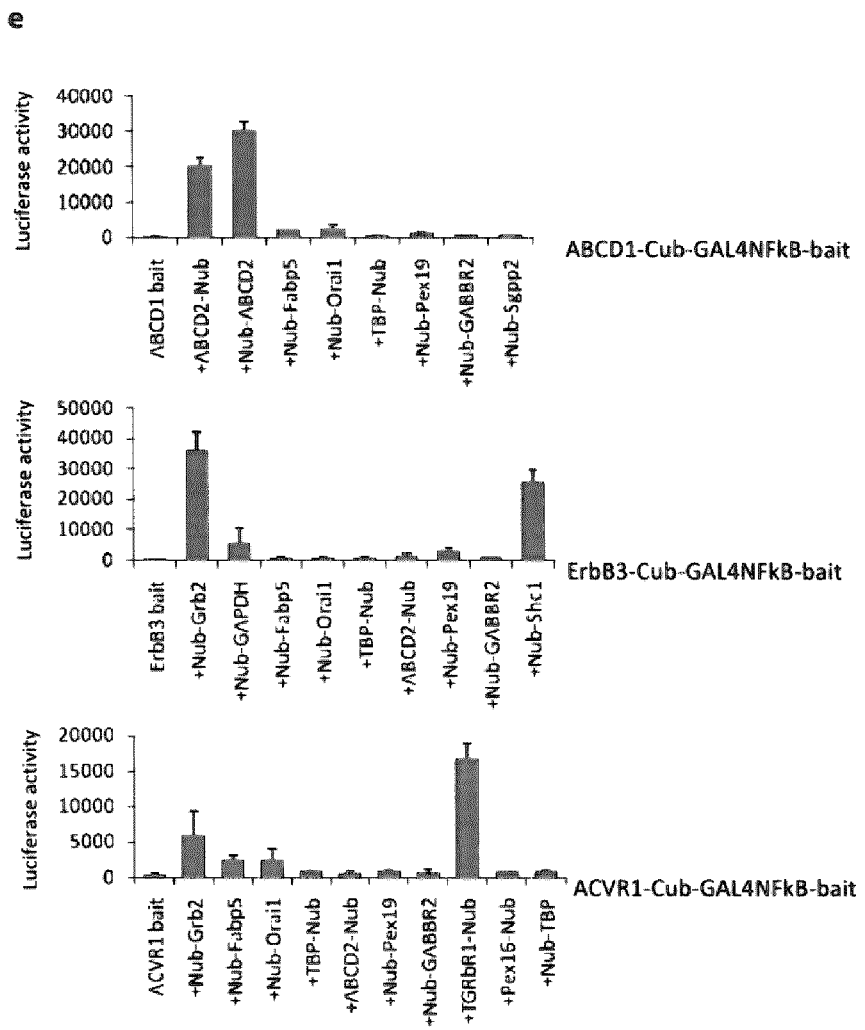

To further assess the specificity of MaMTH, we tested various membrane proteins against their known protein interactors and negative controls (non-interacting proteins) using both TF-bait-set-ups (FIG. 1d, FIG. 5). FIG. 1c shows a representation of correct plasma membrane localization of ErbB-baits that were tagged with Cub-GFP-mLexA-VP16 in order to rule out that the MaMTH-tag has influence on localization and thus function. Bait tags are relatively large, between 1000-1200 bp, thus, bait localization was assayed for ErbB receptors containing Cub-GFP-mLexA-VP16 to test whether the MaMTH tag influences bait localization and thus function. Baits harboring GFP were transfected into reporter cells seeded on poly-L-lysine coated glass plates and 36 h after transfection, cells were stained with a plasma membrane stain (Deep Red, CellMask) and fluorescence microscopy was performed. Next, double EGFR-5× GAL4UAS-reporter- or double ErbB4-5×GAL4UAS-reporter cell lines were infected with indicated preys and luciferase assays were performed (FIG. 1d, FIG. 5c). Double stable bait/luciferase-5×GAL4UAS-luciferase reporter HEK293T cell lines were infected with indicated preys at an MOI (multiplicity of infection) of 0.4. 4 days after infection, cells were lysed and subjected to luciferase assays. As illustrated in FIG. 1d known interactions between EGFR (bottom graph of FIG. 1d) or ErbB4 (top graph of FIG. 1d) with Grb2, Shc1 and Hsp90 could be verified using MaMTH and gave high luciferase signals in comparison to the negative controls. Additionally, EGFR shows interaction with its known partner GAPDH. Positive controls like Grb2, Shc1 and Hsp90 are well detected above background, whereas negative controls were significantly lower or comparable to bait only control. Other known interactions such as the heterodimerization between the G-protein coupled receptor GABBR1-GABBR2 or the TGF-beta receptor TGRβR1-FKBP12 interactions were also successfully reconstituted, among others (FIG. 5b-e). It has to be noted that both co-transfection of bait/prey or infection of bait/prey gives comparable interaction results in both TF-set-ups (FIG. 5b-e).

Figure 4:
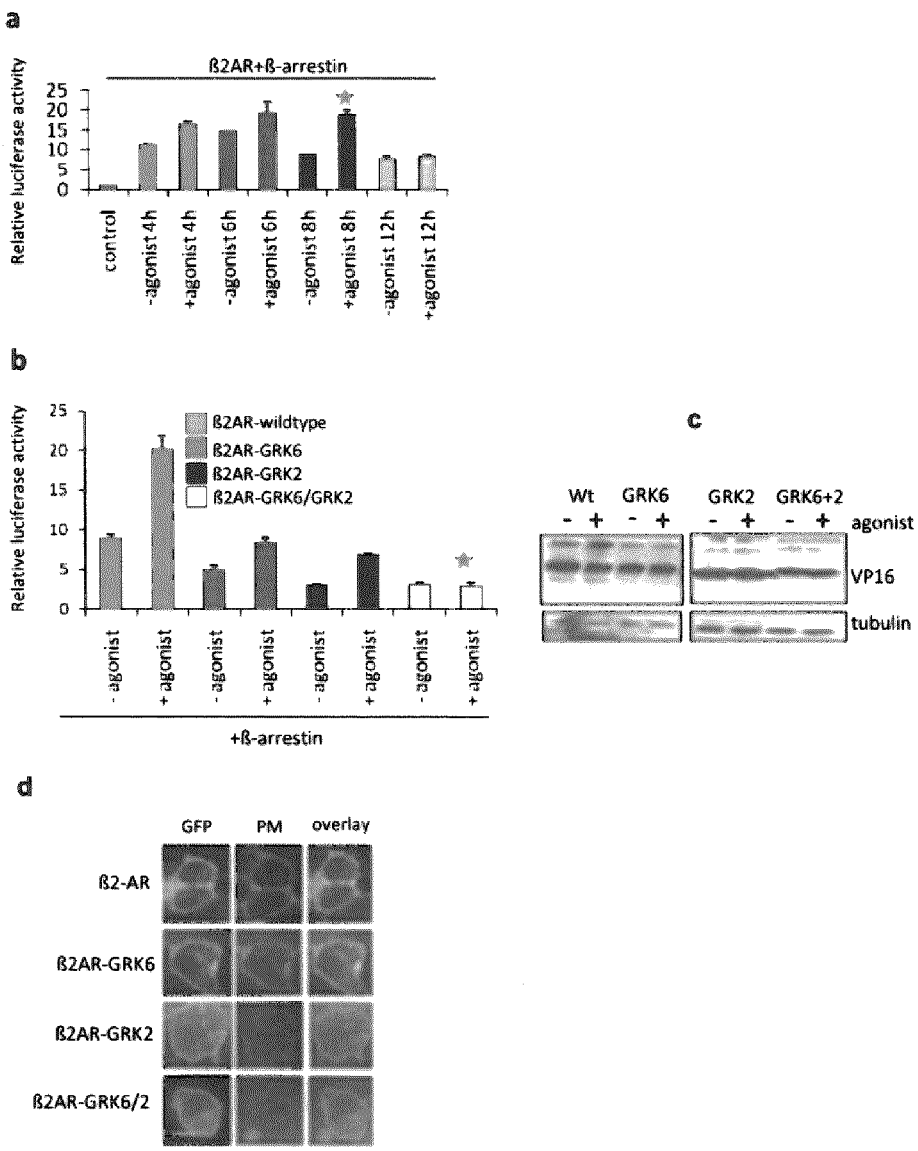
FIG. 4 Graphs and microphotographs illustrating the use of MaMTH to monitor agonist-dependent interactions of β2-AR. (a) Graph illustrating the relative luciferase activity of β2-AR-bait and β-arrestin-prey co-transfected into HEK293T stable 8×lexAops-luciferase reporter cells. Relative luciferase activity is based on fold-change increase above averaged negative controls. (b) Graph illustrating the relative luciferase activity of β2-AR wildtype bait and mutant baits either lacking GRK6-, GRK2 or GRK2+GRK6-phosphorylation sites and β-arrestin-prey co-transfected into HEK293T stable 8×lexAops-luciferase reporter cells. Relative luciferase activity is based on fold-change increase above averaged negative controls. (c) Western Blot analysis using anti-VP16 (to test for bait expression) and anti-tubulin antibodies. (d) Microphotographs illustrating cellular localization of phospho-site mutations (GRK2, GRK6 or GRK2/GRK6-sites) in the β2AR bait construct. Scale bar=10 µM.

MaMTH can Detect Agonist- or Ligand-induced, Drug-inhibited and Phospho-dependent Interactions Monitoring Agonist-induced Interaction Between β2-AR and β-arrestin To further test whether MaMTH can detect inducible interactions, we reconstituted the known protein-protein interactions (PPIs) between the human β2-adrenergic receptor (β2-AR), a G-protein coupled receptor, and β-arrestin[32]. The latter protein will associate with β2-AR only if an agonist such as isoproterenol binds to the receptor, leading to subsequent G-protein signaling, GRK-phosphorylation and β-arrestin binding[32]. FIG. 4a illustrates the efficient detection of the agonist-dependent β2-AR/β-arrestin PPI using MaMTH.

β2-AR-bait and β-arrestin-prey co-transfected into HEK293T stable 8×lexAops-luciferase reporter cells. 24 h after transfection, cells were treated with or without agonist (10 µM isoproterenol) in starvation media for 4-12 h. At indicated time points, cells were harvested and luciferase assays were performed. 8 h after agonist addition, a 2-fold increase in luciferase expression indicated elevated levels of activated receptor, thus leading to increased β-arrestin recruitment. Cell lysates were additionally analyzed for expression levels. Cells are treated with isoproterenol for 8 h in order to better monitor induction of β-arrestin binding. As shown in FIG. 4a binding without agonist can be detected, resulting from residual binding of β-arrestin to β2-AR. In order to test whether this interaction is specific, we mutated GRK phosphorylation sites on β2-AR. β2-AR wildtype bait and mutant baits either lacking GRK6-, GRK2 or GRK2+GRK6-phosphorylation sites and β-arrestin-prey were co-transfected into HEK293T stable 8×lexAops-luciferase reporter cells. 24 h after transfection, cells were treated with 10 µM isoproterenol for 8 h. Cells were lysed and luciferase assays were performed. As shown in FIG. 4b β2-AR lacking GRK2 phospho-sites showed reduced binding of β-arrestin upon agonist addition compared to wildtype, and β2-AR lacking both GRK2 and GRK6 phospho-sites showed no increased binding to β-arrestin upon agonist addition, comparable to untreated conditions. In order to exclude that instability of the mutants leads to decreased binding, we performed Western blot analysis (FIG. 4c) as well as fluorescence microscopy (FIG. 4d). A fraction of the lysates was subjected to Western Blot analysis using anti-VP16 (to test for bait expression) and anti-tubulin antibodies. As shown in FIG. 4c bait mutants show comparable expression with and without agonist, suggesting that reduction of interaction with bait mutants are indeed due to less β-arrestin recruitment. FIG. 4d are microphotographs to test whether introduction of phospho-site mutations (GRK2, GRK6 or GRK2/GRK6-sites) in the β2AR bait construct influences bait localization, GFP was cloned into bait constructs (Cub-GFP-mLexAVP16) and co-localization was performed using a plasma membrane marker (Deep Red Plasma Membrane Stain, Invitrogen CellMask). All mutants tested are equally expressed and localize to the plasma membrane (FIGS. 4c and d).

Figure 7:
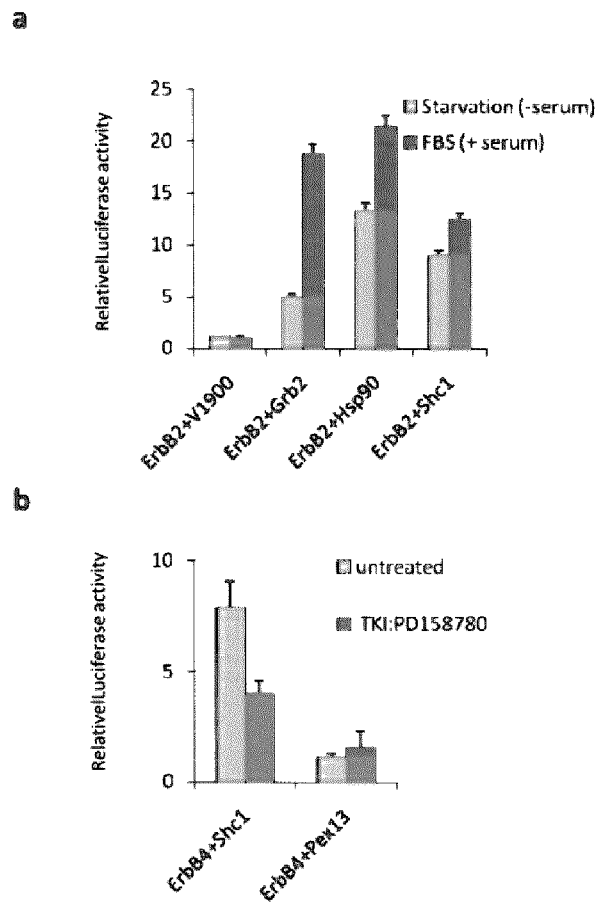
FIG. 7: (a) Graph illustrating relative lucifease activity of serum stimulated PPIs. Stable 5×GAL4UAS-luciferase reporter cell lines were co-transfected with ErbB2 bait and preys. Luciferase activity was measured 24 h following transfection in the absence/presence of serum. Serum-dependent interactions were detected for GrB2, Shc1 and Hsp90. The plotted values represent relative-luciferase signals calculated as fold-change increase above averaged negative controls. (b) Graph illustrating relative luciferase activity of drug-inhibited protein-protein interactions. Following transfection, ErbB4 interaction with either Shc1 or non-interacting Pex13 was measured in presence/absence of non-specfic TKI-PD158780. Plotted values represent relative luciferase signals calculated as fold-change increase above bait only controls.

Monitoring Phosphorylation-dependent Interactions of Oncogenic ErbB Family Members We then sought to more specifically focus on the ErbB subfamily of receptor tyrosine kinases (RTK) to investigate ligand-dependent and drug-inhibited interactions. The ErbB family consists of 4 closely related receptors: EGFR, ErbB2, ErbB3, and ErbB4. Elucidation of cell signaling via all four ErbB receptors is of great therapeutic interest since they are frequently found mutated or overexpressed in several cancer. Upon binding to extracellular ligands, these receptors undergo conformational changes that facilitate their homo- or hetero-dimerization leading to activation of downstream signaling pathways that regulate cell proliferation and survival[33]. To monitor stimuli-dependent PPIs of ErbBs with Shc1 and Grb2 adaptor proteins, and Hsp90-chaperone (which are recruited to the active receptor), we performed MaMTH in the presence and absence of serum. As demonstrated in FIG. 7a, MaMTH allows monitoring of stimuli-dependent PPIs, reflected by an increase in luciferase signal in cells expressing ErbB2 and Grb2, Shc1 or Hsp90 in the presence of serum compared to starved conditions, which was most pronounced in Grb2-expressing cells, while almost no effect was detected in control samples (empty vector or non-interacting Pex13-"prey" protein). Residual activity can be seen in serum-starved cells, reflecting basal receptor phosphorylation. Next, we show that treatment with the non-specific tyrosine kinase inhibitor (TKI-PD158780) can reduce phosphorylation of ErbB4, thus resulting in reduced Shc1-adaptor protein binding, being a first indication that MaMTH allows monitoring of drug-inhibited PPIs (FIG. 7b).

Furthermore, we sought to test if MaMTH interactions can reflect the phosphorylation status of a given receptor through monitoring binding of phospho-dependent interactors. Many versions of oncogenic ErbB receptors are constitutively active, thus increasing downstream signaling involved in proliferative and anti-apoptotic cellular responses[34]. Oncogenic ErbB4 mutants found in melanoma patients[35] were generated and tested for Shc1 binding (FIG. 6a, left panel). Stable 5×GAL4UAS-HEK293T luciferase reporter cells were co-transfected with various oncogenic ErbB baits and Shc1 prey and luciferase activity was measured 24 h after growth in the absence/presence of serum. Oncogenic ErbB4 variants were generated according to Prickett T., et al.[35] ErbB4-E542k and ERbB4-E872K show serum-independent recruitment of Shc1, correlating with the oncogenic characteristics of the receptor. We were able to detect increased Shc1 recruitment to the oncogenic receptors even in the absence of serum compared to wild type receptors, indicating stimuli-independent signaling due to constitutive receptor phosphorylation, correlating with their oncogenic nature. In contrast, ErbB4-R544W mutant shows Shc1 binding comparable to wild type in serum-starved conditions, and has been shown to lead to less pronounced receptor phosphorylation than the other tested mutants[35]. Next, two of the most common oncogenic EGFR-mutants, EGFR-G719S and EGFR-L858R[15] were tested for Shc1 binding (FIG. 6a, right panel). Again, both EGFR-G719S and EGFR-L858R show increased Shc1 binding in serum-independent conditions compared to wild type in serum-starved conditions, with EGFR-L858R also showing an increase in media containing serum. We further investigated mutated forms of EGFR like EGFR-L858R, which, together with EGFR-exon19 deletion, account for 85-90% of all EGFR mutations found in non-small cell lung cancer (NSCLC) patients[15, 36, 37] and which displays constitutively active kinase activity independent of ligand binding[38]. Stable 5×GAL4UAS-HEK293T luciferase reporter cells were co-transfected with EGFR-Wt, EGFR-L858R or EGFR-D855A-kinase dead baits and Shc1 adaptor prey. Cells were grown in the presence/absence of serum for 20 h, lysed and analyzed for luciferase activity. As shown in FIG. 6b constitutively active EGFR-L858R shows increased Shc1 binding in both serum-containing and serum-free media, correlating with its increased phosphorylation status and thus increased Shc1 recruitment compared to wildtype. In contrast, the kinase-dead EGFR-D855A shows no Shc1-binding in both conditions. As seen in FIG. 6b, mutated EGFR-L858R receptor displayed a significantly increased association with Shc1 compared to EGFR-wildtype (EGFR-Wt) in both serum- and serum-free conditions, while the kinase-dead EGFR-D855A lost its ability to bind Shc1 altogether. To exclude that the difference in binding is due to variable receptor protein levels due to different receptor expression, we performed Western blot analysis and show that all mutant receptor are equally expressed as wild type (in both serum- and serum-free conditions, (FIG. 6c, shown is serum-condition only). We also monitored the phosphorylation-status of the various receptors by blotting with anti-phosphotyrosine antibody and show that whereas EGFR-D855A is very weakly phosphorylated, EGFR-L858R shows increased phosphorylation compared to wild type (FIG. 6d).

MaMTH can Capture Erlotinib-inhibited Interactions of Oncogenic EGFR-variants

Figure 8:
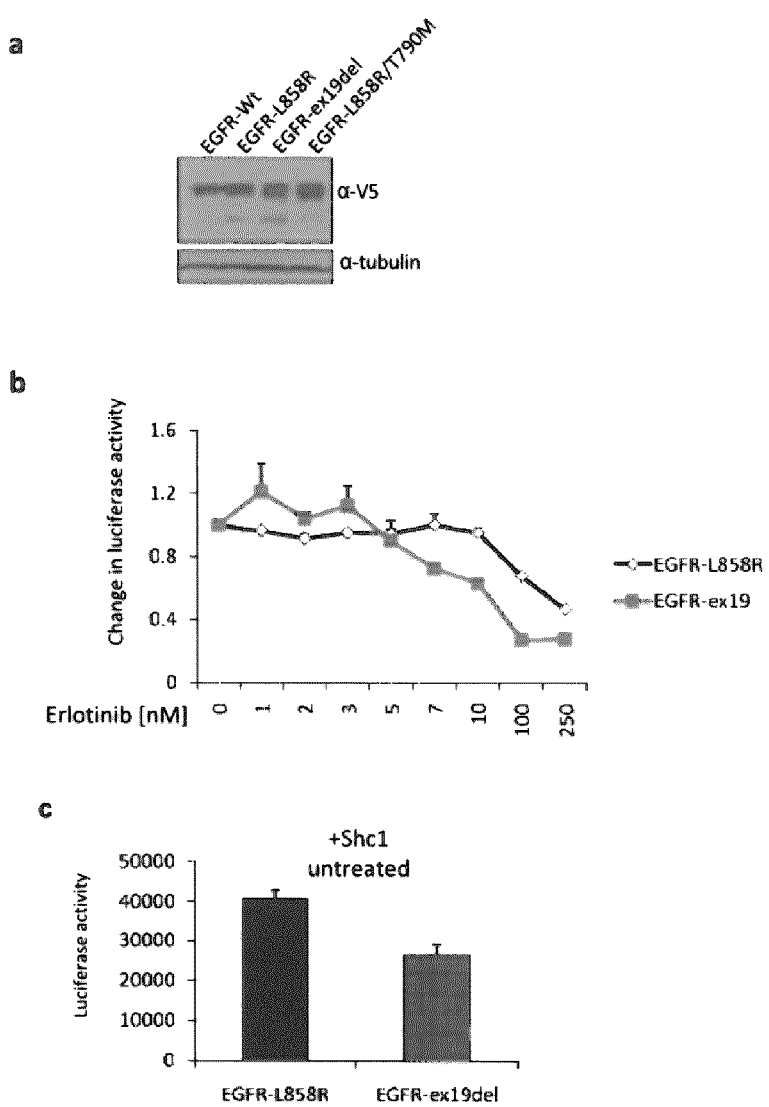
FIG. 8 (a) Western blots using V5 antibodies to test for bait expression show that the mutants are similarly expressed like wildtype. (b) Graph illustrating change in luciferase activity. Stable 5×GAL4UAS-luciferase HEK293T reporter cells were co-transfected with EGFR-L858R or EGFR-exon19del. Cells were grown at indicated concentrations of erlotinib and luciferase assays were performed 20 h after treatment. EGFR-exon19del mutant shows reduced Shc1 binding starting at 5-7 nM, in contrast to EGFR-L858R. (c) Graph illustrating luciferase activity of stable 5×GAL4UAS-luciferase HEK293T reporter cells transfected with EGFR-L858R, EGFR-exon19del and tested for Shc1-binding in serum-containing media without Erlotinib.

Next, we sought to use MaMTH to monitor PPIs that are inhibited by a small molecule drug. Specifically, we used the small-molecule tyrosine kinase inhibitor Erlotinib (Tarceva, OSI-774) that has previously been reported to selectively inhibit the kinase activity of some mutated but not wild type EGFR receptors[15], and thus prevents binding to downstream signaling components such as Shc1 adaptor protein. Erlotinib is in clinical use for lung cancer treatment and especially effective if patients harbor an EGFR-L858R mutation or EGFR-exon19 deletion[39]. Cells were grown at concentrations of erlotinib indicated in FIG. 6e and luciferase assays were performed 20 h after treatment. EGFR-L858R shows decreased Shc1-binding at 150 nM, whereas EGFR-exon19del mutant already at 10 nM. This corresponds with the fact that EGFR-exon19del is more sensitive to erlotinib-treatment than EGFR-L858R. Shc1 binding in EGFR-wildtype is not influenced by erlotinib. FIG. 6e shows that MaMTH efficiently detected the Erlotinib-mediated inhibition of the EGFR-L858R/Shc1 or EGFR-exon19del/Shc1 interaction compared to the EGFR-Wt/Shc1 interaction. Notably, whereas EGFR-Wt/Shc1 binding was unaffected in all Erlotinib concentrations tested, EGFR-L858R had a drop in Shc1 binding starting at 100 nM, whereas EGFR-ex19del mutant showed decreased Shc1 binding at 5-10 nM (FIG. 6e; see also FIG. 8b). This correlates with the previously published study showing that EGFR-ex19del is more sensitive to Erlotinib than EGFR-L858R[40]. Lung cancer patients treated with Erlotinib frequently develop a second EGFR-mutation (L858R/T790M), which renders the receptor unresponsive to Erlotinib treatment due to highly increased ATP affinity and thus increased receptor phosphorylation[36].

In a next step, we monitored Shc1 binding using EGFR-Wt, EGFR-L858R, EGFR-ex1 9del and EGFR-L858R/T790M "bait" proteins. Stable 5×GAL4UAS-luciferase HEK293T reporter cells were co-transfected with indicated baits and Shc1 and treated with 250 nM or 500 nM erlotinib for 20 h, followed by luciferase measurement. As seen in FIG. 6f EGFR-L858R/T790M bait shows constant Shc1 binding in 250/500 nM erlotinib, corresponding with its reported resistance to erlotinib, as the receptor is still phosphorylated irrespective of erlotinib treatment. Importantly, EGFR-L858R/T790M does not show decreased Shc1-binding upon Erlotinib treatment and behaves like EGFR-Wt, correlating with its known Erlotinib-resistance (FIG. 6f). All mutant receptors show higher basal Shc1-binding than EGFR-Wt (FIG. 6g). EGFR-Wt, EGFR-L858R, EGFR-exon19de and EGFR-L858R/T790A baits were transfected into stable5×GAL4UAS-luciferase HEK293T reporter cells in serum-containing media. 6 h after transfection, Erlotinib was added at 0, 250 or 500 nM concentrations and cells were lysed 20 h after treatment and Western Blot analysis was performed using anti-EGFR and anti-phospho-EGFR antibodies. As seen in FIG. 6h increased Shc1 binding correlated with the phosphorylation pattern of the receptors, demonstrating that EGFR-L858R and EGFR-ex19del mutants are sensitive to Erlotinib, whereas both EGFR-Wt and EGFR-L858R/T790 are phosphorylated upon Erlotinib treatment in serum-dependent conditions. Taken together, these examples demonstrate that MaMTH can be used to monitor PPIs that are dependent on the activity (phosphorylation state) of a given receptor.

Using MaMTH to Map Phospho-sites Involved in Protein-protein Interactions We next tested if we can map phospho-sites on a given ErbB receptor responsible for adaptor protein binding. To this end, we generated a set of mutations in designated tyrosines[41], shown in FIG. 9a. We could reconfirm the previously reported Grb2 binding sites on EGFR (FIG. 9b), accurately monitoring an additive effect for double versus single mutant as shown for EGFR-Y1092A and EGFR-Y1092A/Y1138A respectively. Furthermore, we show that ErbB2-Y1139A and ErbB3-Y1262A/Y1199A, which are known phosphor tyrosine binding sites for Grb2, show reduced binding to Grb2 upon ligand-binding compared to wildtype (FIG. 9c). As Shc1 binds to other phosphorylated tyrosines on ErbB2, no effect on Shc1 binding could be observed in the Grb2-phospho-site mutant ErbB2-Y1139A, but could still be detected in ErbB3-Y1262A/Y1199A (FIG. 9d).

Investigation of Dynamic Interaction Patterns of EGFR-wildtype and EGFR-L858R in a Targeted Protein Interaction Screen To this point, we showed that MaMTH can detect phospho-dependent, ligand- or agonist-induced and drug-inhibited interactions between various receptors and their interactors. In order to further our knowledge of EGFR-signaling, we next sought to apply MaMTH to screen for novel interactors of EGFR and its oncogenic variant EGFR-L858R. Mutations in EGFR occur in many cancers such as lung cancer, making this receptor a promising target for anti-cancer therapies. Given that lung cancer is the leading cause of cancer-related mortality worldwide[42], it seems intuitive that gaining insight on how oncogenic receptors are regulated and how they modulate downstream signaling pathways through interactions with various partners is of great importance.

Figure 10:
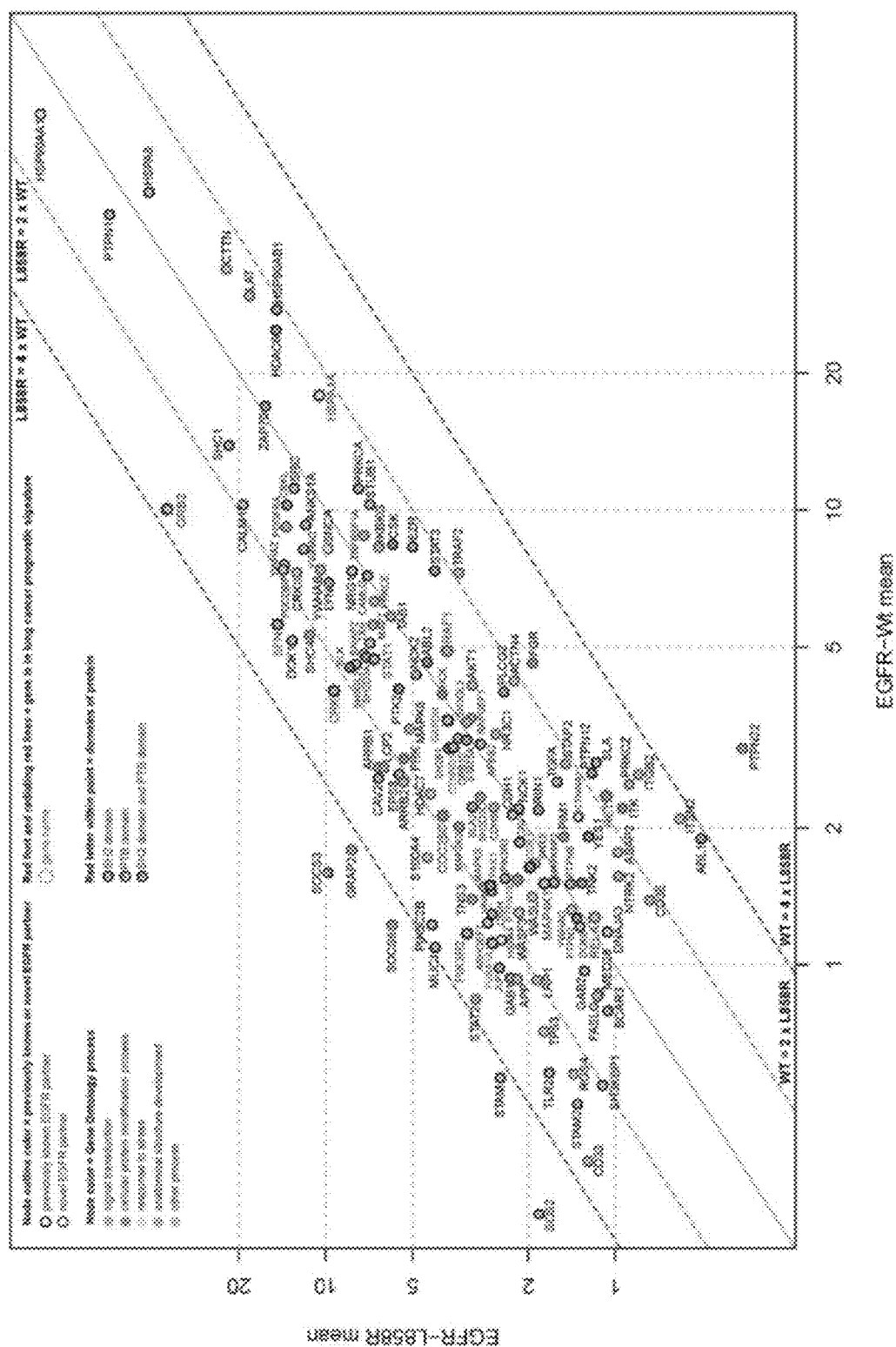
FIG. 10 Dot blot display using MaMTH to identify novel EGFR-Wt and EGFR-L858R interactors.

Therefore, we performed a targeted interaction screen using 206 predicted EGFR-interactors (Table 1). Briefly, stable 5×GAL4UAS-luciferase cell lines were infected with 206 individual lentiviral preys (either C- or N-terminally tagged, depending on their cellular localization) at a low multiplicity of infection (MOI=0.4), selected in puromycin for 3 days and transfected with EGFR-wildtype or EGFR-L858R. It has to be noted that in this case, generation of double reporter/bait stable HEK293T cells was not successful, as stable integration of EGFR-L858R into reporter cells resulted in increased cell death and did not give reproducible luciferase results. Expression of lentiviral preys was assessed (data not shown) and bait expression was randomly tested for both EGFR-Wt and EGFR-L858R. Out of 206 predicted preys, 144 interacted with either EGFR-Wt, EGFR-L858R or both (complete list of interactors tested found in Table 2). Our cut-off of 1 is based on fold-change difference in luciferase activity over averaged negative controls. Negative controls include cytosolic preys (which tend to promiscuously bind to many proteins), plasma membrane- and peroxisomal-prey proteins. In general, we chose stringent conditions by testing preys that tend to have high luciferase background with any bait tested, in order to generate high-confidence interaction data. The interaction data was divided into two sets: preys that bind stronger to EGFR-L858R (86/144 with a ratio interaction score Wt/L858R<0.9), those that bind equally (20/of 144 with an interaction score Wt/L858R 0.9-1.1) and those that bind stronger to EGFR-Wt (38/144 with an interaction score Wt/L858R>1.1). The fact that the majority of preys bind stronger to the mutant receptor is indicative of the increased phospho-status of the mutant receptor and the recruitment of phospho-dependent interactors. Indeed, 27 out of 87 preys that bind stronger to EGFR-L858R contain an SH2 domain, and 2 out of 87 contain a PTB domain (Table 2). Phosphorylated tyrosine residues on the receptor are typically docking sites for downstream cytoplasmic targets and recognized through SH2 or PTB domains[43]. This can be seen with adaptor proteins such as Shc1, CRK and Grb2, which are known to bind more to EGFR-L858R and all contain an SH2 domain. FIG. 10 shows a summarized dot blot of interactions of EGFR-Wt and EGFR-L858R and annotates the interactors to cellular processes as well as lung cancer expression datasets. Among 206 preys tested, around 150 reached the threshold level of 1 (above-mentioned interaction score) in either EGFR-wildtype, EGFR-L858R or both baits tested. The dot blot displays differential strength of binding, preys close to the y-axis are those that interact stronger with EGFR-L858R and preys close to the x-axis show stronger interaction with EGFR-wildtype. Diagonal light grey lines display the area where preys display around a 2-fold higher interaction to either wildtype or mutant. Diagonal dark grey lines display the area where preys display around a 4-fold higher interaction to either wildtype or mutant. Preys at the diagonal black lines interact similar with both wildtype and mutant.

Validation of MaMTH Interactors Using the Orthogonal LUMIER Assay

As a secondary validation of our MaMTH screening assays with either EGFR-wt or EGFR-L858R, a subset of PPIs selected from our interactor dataset was further tested by the orthogonal assay LUMIER[5, 6]. To accomplish this, 60 FLAG-tagged MaMTH interactors were co-transfected with Renilla-tagged EGFR-L858R and EGFR-Wt and serum-starved or starved and treated with EGF and subsequently, LUMIER assay was performed. Out of 60 MaMTH interactors tested, 24 were LUMIER-positive (40%) (FIG. 11a, Table 3). Interactors that were not captured could be those that are transient or weak interactors, thus they might not be picked up by the co-immunoprecipitation (co-IP-based) method.

Figure 11:
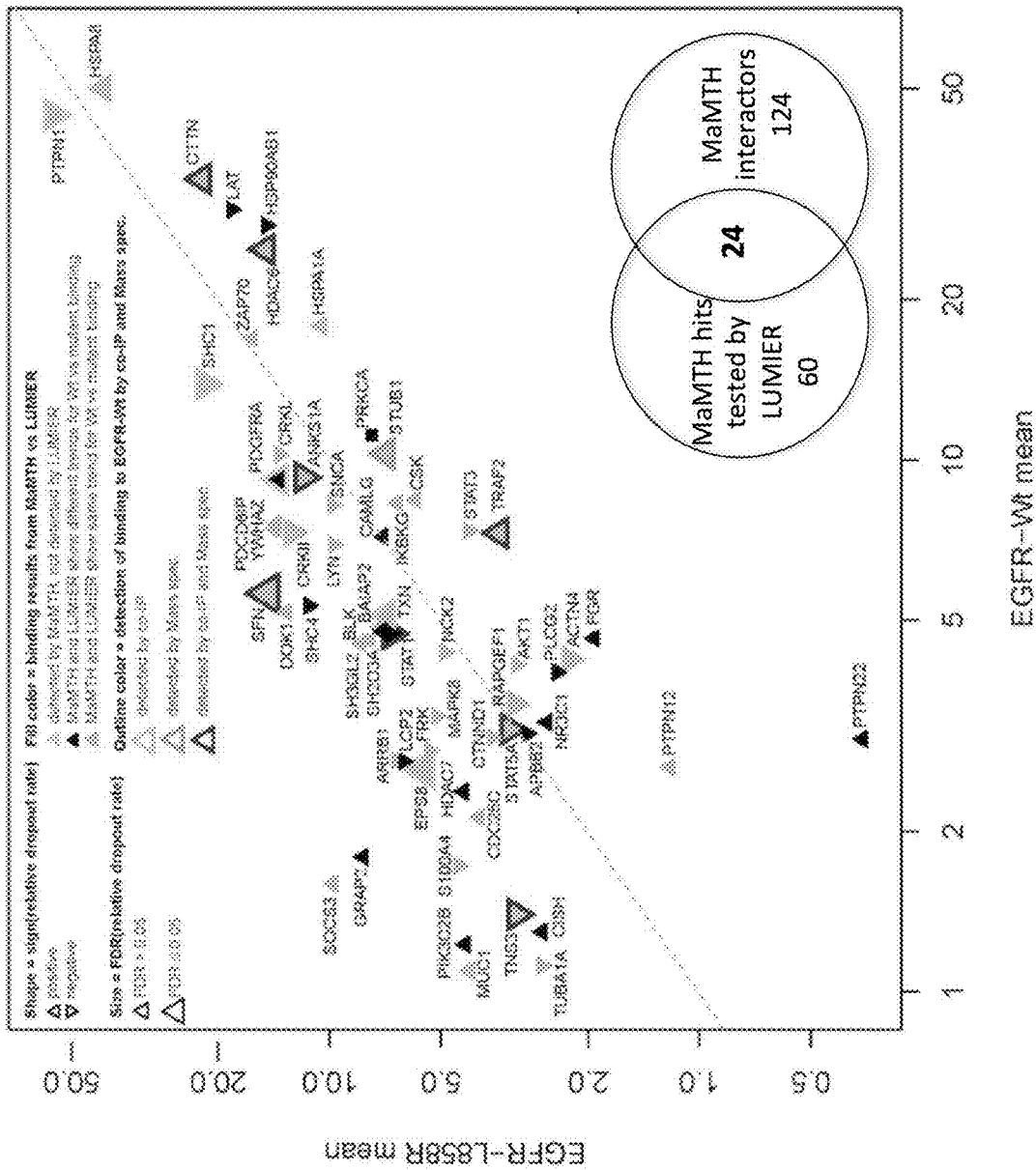
FIG. 11 LUMIER confirmation of MaMTH interactors and shRNA-knockdown overlap. (a) Top MaMTH interactors (based on MaMTH interaction score) were tested by LUMIER. (b) Graphs illustrating MaMTH hits that were confirmed by LUMIER are shown in respect to their shRNA knockdown drop-out rate (fdr<0.3) in Erlotinib-treated cells. Black bars indicate enriched genes (leading to better survival), whereas grey bars indicate depleted genes (leading to less survival).
Figure 11:
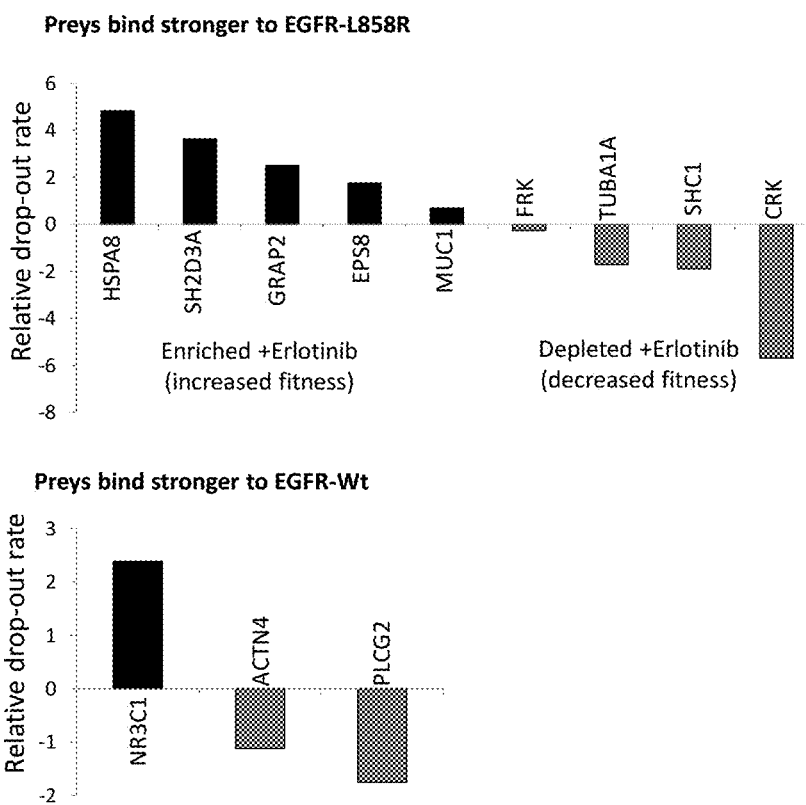

With reference to FIG. 11 (a) genome-wide shRNA-knockdowns were performed in HCC827 cells with and without Erlotinib, and either enrichment or depletion of individual hairpins was measured through microarray hybridiziation. Genes can be depleted in Erlotinib-treated conditions (downward triangle) or enriched, leading to either decreased or increased fitness phenotype.

Overall, given that both assays are substantially different methods (one two-hybrid-based assay, the other co-IP based method), this stresses the quality of our MaMTH PPI screens.

Functional Annotation of MaMTH Hits Reveals Novel Roles of EGFR Interactors in Erlotinib-sensitivity/Resistance In summary, we were able to detect 61 previously undescribed EGFR-interactors (Table 2). Out of 206 bioinformatically predicted interactors, a total of 109 are known EGFR-interactors. Hence, MaMTH could detect 76% of known interactors (87/109), resulting in a false-negative rate of 24%. Several interactors might have been missed due to various reasons such as low lentiviral-based expression of these "prey proteins" or the method of choice to detect interactions.

Overall, it is striking that the EGFR-L858R receptor shows an increased binding pattern to about 60% of the interacting "prey" proteins. This suggests that the oncogenic receptor due to its constitutively active state indeed binds more proteins that are recruited by the phosphorylated receptor. Supporting this notion, it has been postulated that disease-related proteins have a 32% larger number of interactions than their nondisease-versions, which also correlates with our data[44]. Through increased binding of these proteins, down-stream signaling cascades are active, leading to increased proliferation and other cancer-related signatures, which is also reflected by the fact that a large portion of the detected interactors (57/86) are involved in signaling transduction (Table 4). FIG. 10 displays comparison to lung cancer expression datasets. 15 and 38 preys are found either up- or downregulated in 25 lung cancer expression datasets, pointing out a crucial role of these interactors in cancer signaling. Among them, 13 interactors are additionally a prognostic marker for lung cancer (Table 4). One of them is CRK, which, together with CRKL, belongs to the Crk family of adaptor proteins and serve to bridge tyrosine kinases with effector proteins but are also implicated in signaling processes. Both proteins have been shown to contribute to malignant behavior of cells and are often found overexpressed in various cancers[45]. Concomitantly, we show that both CRK and CRKL show increased binding properties towards the EGFR-L858R receptor, being indicative of its oncogenic nature.

STUB1 belongs to the group of interactors that bind stronger to EGFR-Wt. STUB1 has been shown to be implicated in the degradation of ErbB2 in breast cancer, and has been proposed to be a prognostic signature for patient survival. As EGFR-L858R binds less to STUB1, this could indicate that the receptor is more stabilized and less prone to degradation[46].

To further our insight into how these novel preys are involved in EGFR signaling, we compared our MaMTH dataset to shRNA-knockdown experiments performed in HCC827 cells in untreated and Erlotinib-treated conditions. Briefly, HCC827 cells were infected with an 80 k shRNA lentiviral pool at a multiplicity of infection (MOI) of 0.4. Cells were either grown without or with Erlotinib, and over time, certain shRNAs eithe became enriched or depleted from the pools depending on whether the knockdown of the complementary mRNA displays a growth advantage or disadvantage to the cells. At each time point, genomic DNA is isolated from a sub-pool of the cells and the shRNA inserts were PCR-amplified, then digested to reveal the hairpin barcodes and then hybridized to microarrays to determine the relative abundance of each shRNA in the pool. shRNA abundance of untreated and treated HCC827 cells were compared and a relative drop-out rate calculated, which depicts whether knock-down of genes confers a fitness disadvantage (depleted genes) or fitness advantage (enriched genes) upon Erlotinib treatment. We divided our MaMTH interactor dataset into two subsets: preys that bind stronger to EGFR-L858R and preys that bind stronger to EGFR-wildtype and that were also LUMIER-positive. The overlap between interactors and genes that either become depleted (decreased fitness) or enriched (increased fitness) during the shRNA knockdown screen was compared (MaMTH/LUMIER data were compared to the relative drop-out rates of HCC827 untreated/Erlotinib-treated) (FIG. 11a). We just took into account relative drop-out rates with a p-value <0.1 and a fdr (false-discovery rate) of <0.4 to have a high-confident data-set to compare the identified interactors. Preys shown in grey barks fall into the depleted gene category, meaning that knockdown of these candidates leads to decreased fitness with Erlotinib compared to untreated cells. Preys shown in black bars fall into the enriched gene category, meaning that knockdown of these candidates leads to increased fitness with erlotinib compared to untreated cells (FIG. 11b). As an example, GRAP2, which binds stronger to mutant EGFR shows an increased fitness phenotype of HCC827 cells upon Erlotinib treatment, indicating that this protein confers increased sensitivity to Erlotinib. Known interactors such as Shc1 and CRK show decreased fitness in Erlotinib-treated HCC827 cells, suggesting that these proteins confer increased Erlotinib-resistance. This points at important functions of EGFR-interactors in either increasing or decreasing Erlotinib-sensitivity through various regulatory mechanisms, which might involve receptor phosphorylation or stablization or might affect down-stream signaling pathways. In the future, in-depth functional analysis of these novel interactors will give more insight into how 1) EGFR-signaling mechanisms and 2) Erlotinib-mediated sensitivity/resistance are monitored, thus being of utmost importance for future NSCLC drug target definition.

Discussion

Membrane proteins play pivotal roles in cells and have been associated with a variety of diseases. As integral membrane proteins are difficult to work with mainly due to their biochemical features, this poses a major obstacle for designing improved targeted therapies, and importantly, understanding the biology of aberrant signaling pathways associated with integral membrane proteins leading to numerous human diseases.

In the present invention, a novel and inventive MaMTH system is presented, which combines the power of a fast and upscalable genetic assay with the advantage of testing full-length integral membrane proteins and is applicable to specifically test interactions of proteins related to disease-states. The system is based on the reconstitution of ubiquitin from split-halves and presents several advantages over existing techniques to study interactors of membrane proteins: (i) MaMTH can be carried out in virtually any cell line due to the availability of prey/bait/reporter vectors for lentivirus generation, which poses the advantage of single copy integration and diminishes overexpression artefacts. Moreover, MaMTH is carried out in living cells, thus avoiding signal changes arising from cell lysis or protein purification used in biochemical PPI methods; (ii) MaMTH is compatible with the Gateway-recombinatorial cloning technique, allowing for a fast and easy cloning procedure into all vector backbones; (iii) MaMTH can detect subtle changes in interaction patterns, which can be induced/repressed by either drugs, various stimuli or phosphorylation events, in a highly specific manner; (iv) the sensitivity and flexibility of MaMTH makes it amenable for upscaling to high-throughput formats; (v) MaMTH can be used as a platform for drug discovery, specifically used to screen for novel compounds capable of inhibiting signaling mediated by oncogenic receptors.

In this study, we focused on testing interactions of proteins implicated in various diseases like cancer. First, we demonstrated that MaMTH can detect the agonist-induced interaction between the G-protein coupled receptor (GPCR) β2-AR and its cytosolic interactor β-arrestin[32]. GPCRs are often found involved in various diseases and due to their major role in signaling pathways are prime targets for drugs. As many of their interacting proteins have not been identified to date, MaMTH opens new possibilities to test protein partners of other GPCRs in either ligand-occupied or -unoccupied status.

Second, we focused on the ErbB family of receptor tyrosine kinases, whose either overexpression or mutation are involved in many cancers[33]. We showed that MaMTH can successfully detect the oncogenic status of mutant receptors through measurement of associated adaptor proteins. The perturbation of interactions between phospho-tyrosine-dependent proteins like Shc1 or Grb2 and the mutated receptors can terminate or alleviate cancer signatures such as uncontrolled cell proliferation. Additionally, MaMTH can determine Erlotinib-induced loss of Shc1-interaction in two EGFR-mutations that are most commonly found in non-small cell lung cancer patients. Moreover, MaMTH detected increased Shc1-recruitment in the secondary, Erlotinib-resistant EGFR-L858R/T790M mutant[37, 47]. Erlotinib is a tyrosine-kinase inhibitor (TKI) and a potent anti-cancer drug specifically targeting mutant EGFR. TKI-resistance is a major clinical problem, and given that 50% of NSCLC patients who are initially responsive to Erlotinib develop the T790M mutation, this stressed the need for in vivo cell-based assays like MaMTH to test novel pharmaceutical agents directed towards acquired resistance[47, 48].

Last, we expanded MaMTH to test novel EGFR interactors and provide insight into EGFR interactions in both Wt and mutant form. We could detect 76% of known interactors and plus, could identify more than 60 proteins that have not previously been shown to interact with EGFR. This and upscaling MaMTH to genome-wide applications and incorporating shRNA-knockdown data generated in various lung cancer cell lines will greatly increase our knowledge of EGFR-signaling and provide a basis for in-depth mechanistic studies as to how these interactors influence aberrant EGFR signaling.

Taken together, we believe that MaMTH will serve as a powerful platform to identify that specifically interact with disease-variants of receptors, which will be of great importance for the development of novel drugs for the treatment of dysfunctions associated with membrane proteins.

TABLE 1

Predicted preys used for EGFR-Wt and EGFR-L858R screen

| | gene name | EGFR-Wt mean | EGFR-Wt σ | EGFR-L858R mean | EGFR-L858R σ | Wt/L858R | SH2 | PTB |
|---|---|---|---|---|---|---|---|---|
| 1 | ABL1 | 1.894 | 2.502 | 0.504 | 0.114 | 3.76 | yes | |
| 2 | ABL2 | 4.633 | 1.355 | 4.465 | 0.143 | 1.04 | yes | |
| 3 | ACTN4 | 4.215 | 0.524 | 2.239 | 0.926 | 1.88 | | |
| 4 | AKT1 | 4.121 | 0.211 | 3.115 | 1.634 | 1.32 | | |

TABLE 1-continued

Predicted preys used for EGFR-Wt and EGFR-L858R screen

| | gene name | EGFR-Wt mean | EGFR-Wt σ | EGFR-L858R mean | EGFR-L858R σ | Wt/L858R | SH2 | PTB |
|---|---|---|---|---|---|---|---|---|
| 5 | ANKS1A | 9.265 | 0.618 | 11.756 | 1.891 | 0.79 | | |
| 6 | APBB2 | 3.055 | 1.290 | 2.918 | 0.769 | 1.05 | | |
| 7 | APBB3 | 0.506 | 0.085 | 0.972 | 0.298 | 0.52 | | |
| 8 | APP | 0.929 | 0.112 | 2.181 | 0.586 | 0.43 | | |
| 9 | APPL1 | 0.191 | 0.015 | 0.166 | 0.002 | 1.16 | | |
| 10 | APPL2 | 0.780 | 0.267 | 0.614 | 0.329 | 1.27 | | |
| 11 | AREG | 0.855 | 0.197 | 0.655 | 0.177 | 1.30 | | |
| 12 | ARHGEF7 | 1.238 | 0.024 | 2.761 | 0.216 | 0.45 | | |
| 13 | ARRB1 | 2.716 | 0.094 | 6.575 | 1.323 | 0.41 | | |
| 14 | ARRB2 | 2.521 | 0.859 | 5.383 | 1.280 | 0.47 | | |
| 15 | ASAP2 | 1.766 | 0.824 | 0.975 | 0.769 | 1.81 | | |
| 16 | BAIAP2 | 4.832 | 0.544 | 7.370 | 3.366 | 0.66 | | |
| 17 | BCAR3 | 0.791 | 0.373 | 1.057 | 0.525 | 0.75 | yes | |
| 18 | BLK | 4.512 | 0.262 | 8.252 | 0.579 | 0.55 | yes | |
| 19 | BLNK | 0.606 | 0.227 | 0.719 | 0.309 | 0.84 | yes | |
| 20 | BRAF | 0.587 | 0.267 | 0.369 | 0.166 | 1.59 | | |
| 21 | BTC | 0.531 | 0.141 | 0.473 | 0.236 | 1.12 | | |
| 22 | BTK | 0.469 | 0.208 | 0.353 | 0.115 | 1.33 | yes | |
| 23 | CALM1 | 10.260 | 1.812 | 19.357 | 5.062 | 0.53 | | |
| 24 | CAMLG | 7.165 | 0.824 | 7.168 | 2.509 | 1.00 | | |
| 25 | CAV1 | 1.860 | 1.324 | 2.139 | 0.696 | 0.87 | | |
| 26 | CAV2 | 2.569 | 1.069 | 6.577 | 0.063 | 0.39 | | |
| 27 | CBLB | 0.191 | 0.017 | 0.184 | 0.012 | 1.04 | yes | |
| 28 | Cblc | 0.983 | 0.656 | 0.398 | 0.343 | 2.47 | yes | |
| 29 | CD33 | 0.370 | 0.169 | 1.237 | 0.522 | 0.30 | | |
| 30 | CD3E | 1.387 | 0.802 | 0.758 | 0.347 | 1.83 | | |
| 31 | CDC25C | 2.125 | 0.796 | 3.940 | 0.293 | 0.54 | | |
| 32 | Cdh1 | 2.137 | 0.613 | 2.267 | 0.250 | 0.94 | | |
| 33 | CDH5 | 2.216 | 1.028 | 2.627 | 0.562 | 0.84 | | |
| 34 | CDK1 | 1.641 | 0.300 | 1.969 | 0.220 | 0.83 | | |
| 35 | CISH | 1.294 | 0.652 | 2.664 | 0.672 | 0.49 | yes | |
| 36 | Clbc | 0.178 | 0.052 | 0.342 | 0.137 | 0.52 | | |
| 37 | CLTA | 0.143 | 0.097 | 0.111 | 0.032 | 1.29 | | |
| 38 | CRK | 4.007 | 0.185 | 9.356 | 0.938 | 0.43 | yes | |
| 39 | CRKII | 7.287 | 0.342 | 12.623 | 1.041 | 0.58 | | |
| 40 | CRKL | 10.248 | 1.230 | 13.647 | 1.301 | 0.75 | yes | |
| 41 | CSK | 8.401 | 2.023 | 5.863 | 2.914 | 1.43 | yes | |
| 42 | CTNNA1 | 2.115 | 1.731 | 1.339 | 0.661 | 1.58 | | |
| 43 | CTNND1 | 3.004 | 1.198 | 3.626 | 0.920 | 0.83 | | |
| 44 | CTTN | 33.809 | 4.327 | 22.111 | 2.042 | 1.53 | | |
| 45 | DDR1 | 0.927 | 0.210 | 0.942 | 0.226 | 0.98 | | |
| 46 | DLG3 | 0.377 | 0.183 | 0.182 | 0.094 | 2.07 | | |
| 47 | DNAJA3 | 1.183 | 1.401 | 1.062 | 0.348 | 1.11 | | |
| 48 | DOK1 | 5.168 | 0.919 | 13.097 | 2.019 | 0.39 | | |
| 49 | DOK2 | 0.056 | 0.028 | 0.026 | 0.015 | 2.15 | | |
| 50 | DOK4 | 0.971 | 0.245 | 0.802 | 0.375 | 1.21 | | |
| 51 | DOK6 | 1.215 | 0.149 | 1.320 | 0.145 | 0.92 | | |
| 52 | EPHB2 | 0.355 | 0.055 | 0.119 | 0.062 | 3.00 | | |
| 53 | EPHB3 | 0.380 | 0.157 | 0.305 | 0.139 | 1.25 | | |
| 54 | EPS8 | 2.618 | 1.672 | 5.580 | 3.393 | 0.47 | | yes |
| 55 | ESR1 | 0.196 | 0.008 | 0.306 | 0.248 | 0.64 | | |
| 56 | EZR | 8.300 | 2.637 | 5.004 | 0.934 | 1.66 | | |
| 57 | FASLG | 0.852 | 0.135 | 1.150 | 1.032 | 0.74 | | |
| 58 | FES | 0.933 | 0.338 | 0.785 | 0.312 | 1.19 | yes | |
| 59 | FGR | 2.618 | 1.026 | 4.987 | 0.401 | 0.52 | yes | |
| 60 | FLT1 | 0.257 | 0.060 | 0.437 | 0.326 | 0.59 | | |
| 61 | FRK | 2.840 | 0.452 | 5.363 | 1.287 | 0.53 | yes | |
| 62 | FYN | 0.627 | 0.206 | 0.382 | 0.193 | 1.64 | yes | |
| 63 | GAB1 | 0.934 | 0.247 | 2.301 | 0.520 | 0.41 | | |
| 64 | GAB2 | 0.968 | 0.373 | 1.273 | 0.766 | 0.76 | | |
| 65 | Gapdh | 3.443 | 0.462 | 3.789 | 0.620 | 0.91 | | |
| 66 | GHRHR | 0.783 | 0.215 | 0.821 | 0.381 | 0.95 | | |
| 67 | GRAP2 | 1.789 | 0.289 | 8.118 | 2.349 | 0.22 | yes | |
| 68 | GRB10 | 3.145 | 0.951 | 3.488 | 0.555 | 0.90 | yes | |
| 69 | Grb2 | 10.033 | 0.617 | 35.370 | 1.986 | 0.28 | yes | |
| 70 | Grb7 | 0.952 | 0.676 | 0.577 | 0.189 | 1.65 | yes | |
| 71 | HCK | 3.942 | 0.834 | 3.958 | 0.901 | 1.00 | yes | |
| 72 | HDAC1 | 0.532 | 0.162 | 0.757 | 0.164 | 0.70 | | |
| 73 | HDAC6 | 24.861 | 2.741 | 14.896 | 2.723 | 1.67 | | |
| 74 | HDAC7 | 2.372 | 0.832 | 4.347 | 0.848 | 0.55 | | |
| 75 | HRAS | 0.411 | 0.229 | 0.751 | 0.342 | 0.55 | | |
| 76 | Hsp90aa1 | 74.199 | 6.957 | 97.063 | 1.600 | 0.76 | | |
| 77 | HSP90AB1 | 27.578 | 6.513 | 14.811 | 6.636 | 1.86 | | |
| 78 | HSPA1A | 12.770 | 4.200 | 19.200 | 6.7 | 0.67 | | |
| 79 | HSPA4 | 1.135 | 0.746 | 2.477 | 0.252 | 0.46 | | |

TABLE 1-continued

Predicted preys used for EGFR-Wt and EGFR-L858R screen

| | gene name | EGFR-Wt mean | EGFR-Wt σ | EGFR-L858R mean | EGFR-L858R σ | Wt/L858R | SH2 | PTB |
|---|---|---|---|---|---|---|---|---|
| 80 | HSPA8 | 25.000 | 5.000 | 39.200 | 8.100 | 0.64 | | |
| 81 | IGF1R | 0.565 | 0.084 | 0.750 | 0.363 | 0.75 | | |
| 82 | IKBKG | 8.279 | 3.171 | 6.547 | 1.869 | 1.26 | | |
| 83 | INPP5D | 0.433 | 0.103 | 0.678 | 0.111 | 0.64 | yes | |
| 84 | IRS1 | 0.635 | 0.226 | 0.154 | 0.084 | 4.14 | | |
| 85 | ITGB2 | 2.618 | 0.206 | 0.829 | 0.537 | 3.16 | | |
| 86 | ITK | 2.208 | 0.742 | 0.941 | 0.821 | 2.35 | yes | |
| 87 | ITSN2 | 2.093 | 0.728 | 0.598 | 0.204 | 3.50 | | |
| 88 | JAK2 | 0.199 | 0.179 | 0.066 | 0.045 | 2.99 | yes | |
| 89 | JUP | 0.983 | 0.107 | 2.514 | 2.025 | 0.39 | | |
| 90 | LAT | 29.540 | 3.291 | 18.388 | 7.232 | 1.61 | | |
| 91 | LCK | 0.374 | 0.271 | 0.510 | 0.344 | 0.73 | yes | |
| 92 | LCP2 | 2.708 | 1.271 | 6.293 | 0.640 | 0.43 | yes | |
| 93 | LRP1 | 0.923 | 0.408 | 1.863 | 0.260 | 0.50 | | |
| 94 | LYN | 6.921 | 0.569 | 9.741 | 1.446 | 0.71 | yes | |
| 95 | MAP3K13 | 0.528 | 0.151 | 0.424 | 0.284 | 1.24 | | |
| 96 | MAP3K3 | 2.013 | 0.295 | 3.462 | 0.464 | 0.58 | | |
| 97 | MAP4K1 | 1.510 | 0.330 | 1.758 | 0.565 | 0.86 | | |
| 98 | MAPK8 | 3.295 | 1.699 | 5.129 | 0.391 | 0.64 | | |
| 99 | MAPK8IP1 | 0.532 | 0.177 | 0.297 | 0.191 | 1.79 | | |
| 100 | MAPK8IP2 | 1.516 | 0.169 | 1.628 | 0.129 | 0.93 | | |
| 101 | MAPK8IP3 | 0.335 | 0.052 | 0.150 | 0.076 | 2.22 | | |
| 102 | MAPK9 | 1.483 | 0.981 | 2.832 | 0.526 | 0.52 | | |
| 103 | MAPT | 5.592 | 0.829 | 6.862 | 0.403 | 0.81 | | |
| 104 | MATK | 0.092 | 0.009 | 0.088 | 0.057 | 1.05 | yes | |
| 105 | MDM2 | 0.439 | 0.152 | 0.403 | 0.057 | 1.09 | | |
| 106 | MED28 | 0.865 | 0.163 | 1.138 | 0.600 | 0.76 | | |
| 107 | MERTK | 0.173 | 0.122 | 0.368 | 0.199 | 0.47 | | |
| 108 | MUC1 | 1.094 | 0.224 | 4.179 | 3.936 | 0.26 | | |
| 109 | NCK1 | 2.204 | 0.588 | 2.154 | 1.250 | 1.02 | yes | |
| 110 | NCK2 | 4.347 | 1.027 | 4.870 | 1.633 | 0.89 | yes | |
| 111 | NEDD4 | 0.355 | 0.079 | 0.181 | 0.111 | 1.96 | | |
| 112 | NEDD9 | 0.458 | 0.322 | 0.328 | 0.161 | 1.39 | | |
| 113 | NR3C1 | 3.209 | 0.196 | 2.586 | 1.230 | 1.24 | | |
| 114 | NRG1 | 7.339 | 3.278 | 8.101 | 3.087 | 0.91 | | |
| 115 | NTRK2 | 1.566 | 0.336 | 0.971 | 0.150 | 1.61 | | |
| 116 | PAK1 | 1.496 | 1.817 | 2.702 | 0.654 | 0.55 | | |
| 117 | PDCD6IP | 7.391 | 1.814 | 14.051 | 0.623 | 0.53 | | |
| 118 | Pdgfra | 9.182 | 1.985 | 13.730 | 5.467 | 0.67 | | |
| 119 | PDGFRb | 0.233 | 0.205 | 0.096 | 0.013 | 2.42 | | |
| 120 | PIK3C2B | 1.226 | 0.852 | 4.297 | 0.521 | 0.29 | | |
| 121 | PIK3CA | 0.089 | 0.075 | 0.053 | 0.059 | 1.68 | | |
| 122 | PIK3R1 | 0.294 | 0.074 | 0.460 | 0.055 | 0.64 | yes | |
| 123 | PIK3R2 | 1.173 | 0.381 | 3.251 | 0.620 | 0.36 | yes | |
| 124 | PIK3R3 | 1.549 | 0.329 | 2.402 | 0.615 | 0.64 | yes | |
| 125 | PIM1 | 1.911 | 0.211 | 1.510 | 0.210 | 1.27 | | |
| 126 | PLCG2 | 3.986 | 1.543 | 2.427 | 1.317 | 1.64 | yes | |
| 127 | PPP2R2B | 0.624 | 0.042 | 0.640 | 0.328 | 0.98 | | |
| 128 | PRKCA | 11.129 | 3.152 | 7.698 | 2.444 | 1.45 | | |
| 129 | PRKCE | 6.301 | 3.938 | 6.774 | 4.744 | 0.93 | | |
| 130 | PRKCH | 0.817 | 0.033 | 0.883 | 0.016 | 0.92 | | |
| 131 | PRKCZ | 2.493 | 0.453 | 0.892 | 0.244 | 2.79 | | |
| 132 | PTK2 | 4.046 | 0.318 | 5.587 | 1.097 | 0.72 | | |
| 133 | PTPN1 | 44.557 | 2.651 | 55.899 | 9.522 | 0.80 | | |
| 134 | PTPN11 | 0.086 | 0.029 | 0.253 | 0.298 | 0.34 | yes | |
| 135 | PTPN12 | 2.637 | 1.507 | 1.201 | 0.299 | 2.20 | | |
| 136 | PTPN14 | 0.402 | 0.194 | 0.488 | 0.296 | 0.82 | | |
| 137 | PTPN18 | 1.538 | 0.544 | 2.180 | 0.876 | 0.71 | | |
| 138 | PTPN2 | 1.267 | 0.256 | 1.356 | 0.981 | 0.93 | | |
| 139 | PTPN22 | 2.986 | 4.641 | 0.363 | 0.064 | 8.23 | | |
| 140 | PTPN6 | 1.507 | 0.624 | 1.431 | 1.505 | 1.05 | yes | |
| 141 | PTPRA | 0.333 | 0.214 | 0.814 | 0.292 | 0.41 | | |
| 142 | PTPRM | 0.354 | 0.182 | 0.355 | 0.195 | 1.00 | | |
| 143 | Pxn | 0.341 | 0.102 | 0.272 | 0.087 | 1.26 | | |
| 144 | RAF1 | 4.906 | 0.419 | 3.809 | 0.502 | 1.29 | | |
| 145 | RAPGEF1 | 3.476 | 0.440 | 3.149 | 0.509 | 1.10 | | |
| 146 | RELA | 1.271 | 0.521 | 1.177 | 0.767 | 1.08 | | |
| 147 | RET | 2.347 | 0.744 | 1.071 | 0.542 | 2.19 | | |
| 148 | Rgs4 | 0.575 | 0.262 | 1.392 | 0.595 | 0.41 | | |
| 149 | RIN1 | 2.189 | 1.648 | 1.842 | 0.655 | 1.19 | yes | |
| 150 | ROS1 | 0.504 | 0.186 | 0.264 | 0.051 | 1.91 | | |
| 151 | S100A4 | 1.722 | 0.519 | 4.461 | 1.491 | 0.39 | | |
| 152 | SFN | 5.605 | 0.681 | 14.701 | 0.391 | 0.38 | | |
| 153 | SH2B1 | 2.988 | 0.974 | 3.761 | 1.349 | 0.79 | yes | |
| 154 | SH2B3 | 0.248 | 0.082 | 0.227 | 0.066 | 1.09 | yes | |

TABLE 1-continued

Predicted preys used for EGFR-Wt and EGFR-L858R screen

| | gene name | EGFR-Wt mean | EGFR-Wt σ | EGFR-L858R mean | EGFR-L858R σ | Wt/L858R | SH2 | PTB |
|---|---|---|---|---|---|---|---|---|
| 155 | SH2D2A | 0.228 | 0.158 | 0.436 | 0.104 | 0.52 | yes | |
| 156 | SH2D3A | 4.752 | 0.627 | 7.233 | 1.568 | 0.66 | yes | |
| 157 | SH2D3C | 2.333 | 0.399 | 2.924 | 0.755 | 0.80 | yes | |
| 158 | SH3BP2 | 0.337 | 0.095 | 0.532 | 0.153 | 0.63 | yes | |
| 159 | SH3GL1 | 0.812 | 0.632 | 0.718 | 0.319 | 1.13 | | |
| 160 | SH3GL2 | 4.583 | 0.341 | 7.850 | 1.261 | 0.58 | | |
| 161 | SH3GL3 | 3.413 | 0.550 | 3.258 | 1.017 | 1.05 | | |
| 162 | SH3KBP1 | 0.543 | 0.337 | 1.102 | 0.556 | 0.49 | | |
| 163 | Shc1 | 13.893 | 1.250 | 21.648 | 3.644 | 0.64 | yes | |
| 164 | SHC4 | 5.313 | 0.844 | 11.387 | 1.366 | 0.47 | yes | |
| 165 | SLA | 2.783 | 2.074 | 1.160 | 0.237 | 2.40 | yes | |
| 166 | SLA2 | 2.222 | 0.874 | 3.113 | 0.086 | 0.71 | yes | |
| 167 | SNCA | 8.214 | 1.575 | 9.827 | 4.881 | 0.84 | | |
| 168 | SNX9 | 1.670 | 0.371 | 1.894 | 0.291 | 0.88 | | |
| 169 | SOCS3 | 1.594 | 0.664 | 9.826 | 4.051 | 0.16 | yes | |
| 170 | SOCS5 | 0.294 | 0.121 | 0.876 | 0.278 | 0.34 | yes | |
| 171 | SOCS6 | 1.224 | 0.342 | 5.900 | 0.979 | 0.21 | yes | |
| 172 | SOS2 | 0.283 | 0.053 | 1.834 | 0.341 | 0.15 | | |
| 173 | Src | 11.156 | 1.745 | 12.900 | 0.542 | 0.86 | yes | |
| 174 | STAM | 0.564 | 0.349 | 2.495 | 1.227 | 0.23 | | |
| 175 | STAM2 | 0.494 | 0.266 | 1.349 | 0.120 | 0.37 | | |
| 176 | STAP2 | 2.763 | 0.201 | 1.488 | 0.965 | 1.86 | yes | |
| 177 | STAT1 | 4.705 | 0.594 | 6.800 | 2.807 | 0.69 | yes | |
| 178 | STAT2 | 0.838 | 0.243 | 3.034 | 0.258 | 0.28 | yes | |
| 179 | STAT3 | 7.348 | 2.861 | 4.199 | 0.719 | 1.75 | yes | |
| 180 | STAT5A | 3.116 | 1.055 | 3.261 | 1.111 | 0.96 | yes | |
| 181 | STUB1 | 10.282 | 1.710 | 7.036 | 1.455 | 1.46 | | |
| 182 | SYK | 0.761 | 0.219 | 0.956 | 0.606 | 0.80 | yes | |
| 183 | TAB1 | 5.840 | 2.812 | 5.948 | 1.401 | 0.98 | | |
| 184 | TBK1 | 0.285 | 0.150 | 0.334 | 0.064 | 0.85 | | |
| 185 | TENC1 | 0.738 | 0.263 | 0.193 | 0.229 | 3.83 | yes | yes |
| 186 | TGFA | 2.523 | 1.649 | 1.590 | 0.931 | 1.59 | | |
| 187 | TLR2 | 0.578 | 0.195 | 1.692 | 1.120 | 0.34 | | |
| 188 | TNFRSF1A | 8.777 | 2.653 | 7.369 | 2.573 | 1.19 | | |
| 189 | TNK2 | 1.512 | 1.618 | 1.299 | 0.802 | 1.16 | | |
| 190 | TNS3 | 1.395 | 0.581 | 3.120 | 0.509 | 0.45 | yes | yes |
| 191 | TP53 | 0.713 | 0.259 | 1.765 | 0.699 | 0.40 | | |
| 192 | TRAF2 | 7.278 | 1.243 | 3.472 | 0.749 | 2.10 | | |
| 193 | TUBA1A | 1.117 | 0.474 | 2.662 | 0.558 | 0.42 | | |
| 194 | TXN | 5.099 | 0.852 | 7.026 | 0.402 | 0.73 | | |
| 195 | TYK2 | 0.570 | 0.075 | 0.790 | 0.201 | 0.72 | yes | |
| 196 | VAV1 | 1.454 | 0.106 | 2.675 | 0.143 | 0.54 | yes | |
| 197 | WAS | 0.231 | 0.198 | 0.149 | 0.084 | 1.56 | | |
| 198 | WASF3 | 1.303 | 0.688 | 2.154 | 0.198 | 0.61 | | |
| 199 | WASL | 1.411 | 0.134 | 1.933 | 0.295 | 0.73 | | |
| 200 | YES1 | 1.913 | 0.767 | 1.233 | 0.260 | 1.55 | yes | |
| 201 | YWHAB | 7.392 | 2.991 | 10.442 | 2.583 | 0.71 | | |
| 202 | YWHAB | 1.338 | 0.795 | 0.868 | 0.027 | 1.54 | | |
| 203 | YWHAG | 1.323 | 0.954 | 1.415 | 0.671 | 0.93 | | |
| 204 | YWHAQ | 8.195 | 1.358 | 11.957 | 3.303 | 0.69 | | |
| 205 | YWHAZ | 7.577 | 0.892 | 13.937 | 3.130 | 0.54 | | |
| 206 | ZAP70 | 16.923 | 0.872 | 16.203 | 0.977 | 1.04 | yes | |

TABLE 2

Identified EGFR-Interactors (previously unknown EGFR-interactors are shown in bold)

| | Gene | EGFR-Wt mean | EGFR-L858R mean | Wt/L858R | SH2 | PTB |
|---|---|---|---|---|---|---|
| 1 | SOS2 | 0.28 | 1.83 | 0.15 | | |
| 2 | SOCS3 | 1.59 | 9.83 | 0.16 | yes | |
| 3 | SOCS6 | 1.22 | 5.90 | 0.21 | yes | |
| 4 | GRAP2 | 1.79 | 8.12 | 0.22 | yes | |
| 5 | STAM | 0.56 | 2.49 | 0.23 | | |
| 6 | MUC1 | 1.09 | 4.18 | 0.26 | | |
| 7 | STAT2 | 0.84 | 3.03 | 0.28 | yes | |
| 8 | Grb2 | 10.03 | 35.37 | 0.28 | yes | |
| 9 | PIK3C2B | 1.23 | 4.30 | 0.29 | | |
| 10 | CD33 | 0.37 | 1.24 | 0.30 | | |
| 11 | TLR2 | 0.58 | 1.69 | 0.34 | | |
| 12 | PIK3R2 | 1.17 | 3.25 | 0.36 | yes | |
| 13 | STAM2 | 0.49 | 1.35 | 0.37 | | |
| 14 | SFN | 5.60 | 14.70 | 0.38 | | |
| 15 | S100A4 | 1.72 | 4.46 | 0.39 | | |
| 16 | CAV2 | 2.57 | 6.58 | 0.39 | | |
| 17 | JUP | 0.98 | 2.51 | 0.39 | | |
| 18 | DOK1 | 5.17 | 13.10 | 0.39 | | |
| 19 | TP53 | 0.71 | 1.77 | 0.40 | | |
| 20 | GAB1 | 0.93 | 2.30 | 0.41 | | |
| 21 | ARRB1 | 2.72 | 6.57 | 0.41 | | |
| 22 | Rgs4 | 0.58 | 1.39 | 0.41 | | |

TABLE 2-continued

Identified EGFR-Interactors (previously unknown EGFR-interactors are shown in bold)

| | Gene | EGFR-Wt mean | EGFR-L858R mean | Wt/L858R | SH2 | PTB |
|---|---|---|---|---|---|---|
| 23 | TUBA1A | 1.12 | 2.66 | 0.42 | | |
| 24 | APP | 0.93 | 2.18 | 0.43 | | |
| 25 | LCP2 | 2.71 | 6.29 | 0.43 | yes | |
| 26 | TNS3 | 1.39 | 3.12 | 0.45 | yes | yes |
| 27 | ARHGEF7 | 1.24 | 2.76 | 0.45 | | |
| 28 | HSPA4 | 1.13 | 2.48 | 0.46 | | |
| 29 | SHC4 | 5.31 | 11.39 | 0.47 | yes | |
| 30 | ARRB2 | 2.52 | 5.38 | 0.47 | | |
| 31 | EPS8 | 2.62 | 5.58 | 0.47 | | yes |
| 32 | CISH | 1.29 | 2.66 | 0.49 | yes | |
| 33 | SH3KBP1 | 0.54 | 1.10 | 0.49 | | |
| 34 | LRP1 | 0.92 | 1.86 | 0.50 | | |
| 35 | MAPK9 | 1.48 | 2.83 | 0.52 | | |
| 36 | PDCD6IP | 7.39 | 14.05 | 0.53 | | |
| 37 | FRK | 2.84 | 5.36 | 0.53 | yes | |
| 38 | CALM1 | 10.26 | 19.36 | 0.53 | | |
| 39 | CDC25C | 2.12 | 3.94 | 0.54 | | |
| 40 | VAV1 | 1.45 | 2.68 | 0.54 | yes | |
| 41 | YWHAZ | 7.58 | 13.94 | 0.54 | | |
| 42 | HDAC7 | 2.37 | 4.35 | 0.55 | | |
| 43 | BLK | 4.51 | 8.25 | 0.55 | yes | |
| 44 | PAK1 | 1.50 | 2.70 | 0.55 | | |
| 45 | CRKII | 7.29 | 12.62 | 0.58 | | |
| 46 | MAP3K3 | 2.01 | 3.46 | 0.58 | | |
| 47 | SH3GL2 | 4.58 | 7.85 | 0.58 | | |
| 48 | WASF3 | 1.30 | 2.15 | 0.61 | | |
| 49 | HSPA8 | 25.00 | 39.20 | 0.64 | | |
| 50 | Shc1 | 13.89 | 21.65 | 0.64 | yes | |
| 51 | MAPK8 | 3.30 | 5.13 | 0.64 | | |
| 52 | PIK3R3 | 1.55 | 2.40 | 0.64 | yes | |
| 53 | BAIAP2 | 4.83 | 7.37 | 0.66 | | |
| 54 | SH2D3A | 4.75 | 7.23 | 0.66 | yes | |
| 55 | HSPA1A | 12.77 | 19.20 | 0.67 | | |
| 56 | Pdgfra | 9.18 | 13.73 | 0.67 | | |
| 57 | YWHAQ | 8.19 | 11.96 | 0.69 | | |
| 58 | STAT1 | 4.70 | 6.80 | 0.69 | yes | |
| 59 | PTPN18 | 1.54 | 2.18 | 0.71 | | |
| 60 | YWHAB | 7.39 | 10.44 | 0.71 | | |
| 61 | LYN | 6.92 | 9.74 | 0.71 | yes | |
| 62 | SLA2 | 2.22 | 3.11 | 0.71 | yes | |
| 63 | PTK2 | 4.05 | 5.59 | 0.72 | | |
| 64 | TXN | 5.10 | 7.03 | 0.73 | | |
| 65 | WASL | 1.41 | 1.93 | 0.73 | | |
| 66 | FASLG | 0.85 | 1.15 | 0.74 | | |
| 67 | BCAR3 | 0.79 | 1.06 | 0.75 | yes | |
| 68 | CRKL | 10.25 | 13.65 | 0.75 | yes | |
| 69 | GAB2 | 0.97 | 1.27 | 0.76 | | |
| 70 | MED28 | 0.87 | 1.14 | 0.76 | | |
| 71 | Hsp90aa1 | 74.20 | 97.06 | 0.76 | | |
| 72 | ANKS1A | 9.27 | 11.76 | 0.79 | | |
| 73 | SH2B1 | 2.99 | 3.76 | 0.79 | yes | |
| 74 | PTPN1 | 44.56 | 55.90 | 0.80 | | |
| 75 | SH2D3C | 2.33 | 2.92 | 0.80 | yes | |
| 76 | MAPT | 5.59 | 6.86 | 0.81 | | |
| 77 | CTNND1 | 3.00 | 3.63 | 0.83 | | |
| 78 | CDK1 | 1.64 | 1.97 | 0.83 | | |
| 79 | SNCA | 8.21 | 9.83 | 0.84 | | |
| 80 | CDH5 | 2.22 | 2.63 | 0.84 | | |
| 81 | MAP4K1 | 1.51 | 1.76 | 0.86 | | |
| 82 | Src | 11.16 | 12.90 | 0.86 | yes | |
| 83 | CAV1 | 1.86 | 2.14 | 0.87 | | |
| 84 | SNX9 | 1.67 | 1.89 | 0.88 | | |
| 85 | NCK2 | 4.35 | 4.87 | 0.89 | yes | |
| 86 | GRB10 | 3.14 | 3.49 | 0.90 | yes | |
| 87 | NRG1 | 7.34 | 8.10 | 0.91 | | |
| 88 | Gapdh | 3.44 | 3.79 | 0.91 | | |
| 89 | DOK6 | 1.22 | 1.32 | 0.92 | | |
| 90 | PRKCE | 6.30 | 6.77 | 0.93 | | |
| 91 | MAPK8IP2 | 1.52 | 1.63 | 0.93 | | |
| 92 | PTPN2 | 1.27 | 1.36 | 0.93 | | |
| 93 | YWHAG | 1.32 | 1.42 | 0.93 | | |
| 94 | Cdh1 | 2.14 | 2.27 | 0.94 | | |
| 95 | STAT5A | 3.12 | 3.26 | 0.96 | yes | |
| 96 | TAB1 | 5.84 | 5.95 | 0.98 | | |
| 97 | HCK | 3.94 | 3.96 | 1.00 | yes | |
| 98 | CAMLG | 7.16 | 7.17 | 1.00 | | |
| 99 | NCK1 | 2.20 | 2.15 | 1.02 | yes | |
| 100 | ABL2 | 4.63 | 4.47 | 1.04 | yes | |
| 101 | ZAP70 | 16.92 | 16.20 | 1.04 | yes | |
| 102 | APBB2 | 3.05 | 2.92 | 1.05 | | |
| 103 | SH3GL3 | 3.41 | 3.26 | 1.05 | | |
| 104 | PTPN6 | 1.51 | 1.43 | 1.05 | yes | |
| 105 | RELA | 1.27 | 1.18 | 1.08 | | |
| 106 | RAPGEF1 | 3.48 | 3.15 | 1.10 | | |
| 107 | DNAJA3 | 1.18 | 1.06 | 1.11 | | |
| 108 | TNK2 | 1.51 | 1.30 | 1.16 | | |
| 109 | RIN1 | 2.19 | 1.84 | 1.19 | yes | |
| 110 | TNFRSF1A | 8.78 | 7.37 | 1.19 | | |
| 111 | NR3C1 | 3.21 | 2.59 | 1.24 | | |
| 112 | IKBKG | 8.28 | 6.55 | 1.26 | | |
| 113 | PIM1 | 1.91 | 1.51 | 1.27 | | |
| 114 | RAF1 | 4.91 | 3.81 | 1.29 | | |
| 115 | AKT1 | 4.12 | 3.11 | 1.32 | | |
| 116 | CSK | 8.40 | 5.86 | 1.43 | yes | |
| 117 | PRKCA | 11.13 | 7.70 | 1.45 | | |
| 118 | STUB1 | 10.28 | 7.04 | 1.46 | | |
| 119 | CTTN | 33.81 | 22.11 | 1.53 | | |
| 120 | YES1 | 1.91 | 1.23 | 1.55 | yes | |
| 121 | CTNNA1 | 2.11 | 1.34 | 1.58 | | |
| 122 | TGFA | 2.52 | 1.59 | 1.59 | | |
| 123 | LAT | 29.54 | 18.39 | 1.61 | | |
| 124 | NTRK2 | 1.57 | 0.97 | 1.61 | | |
| 125 | PLCG2 | 3.99 | 2.43 | 1.64 | yes | |
| 126 | EZR | 8.30 | 5.00 | 1.66 | | |
| 127 | HDAC6 | 24.86 | 14.90 | 1.67 | | |
| 128 | STAT3 | 7.35 | 4.20 | 1.75 | yes | |
| 129 | ASAP2 | 1.77 | 0.97 | 1.81 | | |
| 130 | CD3E | 1.39 | 0.76 | 1.83 | | |
| 131 | STAP2 | 2.76 | 1.49 | 1.86 | yes | |
| 132 | HSP90AB1 | 27.58 | 14.81 | 1.86 | | |
| 133 | ACTN4 | 4.21 | 2.24 | 1.88 | | |
| 134 | TRAF2 | 7.28 | 3.47 | 2.10 | | |
| 135 | RET | 2.35 | 1.07 | 2.19 | | |
| 136 | PTPN12 | 2.64 | 1.20 | 2.20 | | |
| 137 | ITK | 2.21 | 0.94 | 2.35 | yes | |
| 138 | FGR | 2.62 | 4.99 | 0.52 | yes | |
| 139 | SLA | 2.78 | 1.16 | 2.40 | yes | |
| 140 | PRKCZ | 2.49 | 0.89 | 2.79 | | |
| 141 | ITGB2 | 2.62 | 0.83 | 3.16 | | |
| 142 | ITSN2 | 2.09 | 0.60 | 3.50 | | |
| 143 | ABL1 | 1.89 | 0.50 | 3.76 | yes | |
| 144 | PTPN22 | 2.99 | 0.36 | 8.23 | | |

TABLE 3

Confirmation of MaMTH hits by LUMIER (p-value <0.05)

| | |
|---|---|
| 1 | APBB2 |
| 2 | CAMLG |
| 3 | CISH |
| 4 | CRKII |
| 5 | FGR |
| 6 | GRAP2 |
| 7 | HDAC7 |
| 8 | HSP90AB1 |
| 9 | HSPA1A |
| 10 | HSPA8 |
| 11 | LAT |
| 12 | LCP2 |
| 13 | MUC1 |
| 14 | NR3C1 |
| 15 | PDGFRA |
| 16 | PIK3C2B |
| 17 | PLCG2 |
| 18 | PRKCA |

TABLE 3-continued

Confirmation of MaMTH hits by LUMIER (p-value <0.05)

| | |
|---|---|
| 19 | PTPN22 |
| 20 | SH2D3A |
| 21 | SHC1 |
| 22 | SHC4 |
| 23 | STAT1 |
| 24 | TNS3 |

TABLE 5

MaMTH vector backbones

| | | Features |
|---|---|---|
| Prey destination vectors | | |
| pCMV-y/hNubI-tripleFLAG-linker-Gateway | N-tagged NubI-plasmid for transfection | CMV-promoter, Kozak(GCCACC)-yeast or human NubI (aa1-37)-3xFLAG-(GGGGS)2-Gateway cassette |
| pCMV-y/hNubV-tripleFLAG-linker-Gateway | N-tagged NubV-plasmid for transfection | CMV-promoter, Kozak(GCCACC)-yeast or human NubV (aa1-37)-3xFLAG-(GGGGS)2-Gateway cassette |
| pCMV-y/hNubA-tripleFLAG-linker-Gateway | N-tagged NubA-plasmid for transfection | CMV-promoter, Kozak(GCCACC)-yeast or human NubA (aa1-37)-3xFLAG-(GGGGS)2-Gateway cassette |
| pCMV-y/hNubG-tripleFLAG-linker-Gateway | N-tagged NubG-plasmid for transfection | CMV-promoter, Kozak(GCCACC)-yeast or human NubG (aa1-37)-3xFLAG-(GGGGS)2-Gateway cassette |
| pCMV-Gateway-linker-tripleFLAG-y/hNubi | C-tagged Nubi-plasmid for transfection | CMV-promoter, Gateway cassette, (GGGGS)2-3xFLAG-yeast or human Nubi (aa1-37) |
| pCMV-Gateway-linker-tripleFLAG-y/hNubV | C-tagged NubV-plasmid for transfection | CMV-promoter, Gateway cassette, (GGGGS)2-3xFLAG-yeast or human NubV (aa1-37) |
| pCMV-Gateway-linker-tripleFLAG-y/hNubA | C-tagged NubA-plasmid for transfection | CMV-promoter, Gateway cassette, (GGGGS)2-3xFLAG-yeast or human NubA (aa1-37) |
| pCMV-Gateway-linker-tripleFLAG-y/hNubG | C-tagged NubG-plasmid for transfection | CMV-promoter, Gateway cassette, (GGGGS)2-3xFLAG-yeast or human NubG (aa1-37) |
| pLV-CMV-y/hNubI-tripleFLAG-linker-Gateway-PuroR | lentiviral N-tagged Nubi-plasmid, puromycin marker | CMV-promoter, Kozak(GCCACC)-yeast or human NubI (aa1-37)-3xFLAG-(GGGGS)2-Gateway cassette |
| pLV-CMV-Gateway-linker-tripleFLAG-y/hNubi | lentiviral C-tagged Nubi-plasmid, puromycin marker | CMV-promoter, Gateway cassette, (GGGGS)2-3xFLAG-yeast or human Nubi (aa1-37) |
| Bait destinaction vectors | | |
| pCMV-Gateway-linker-GAL4-mNFkB-V5 | C-tagged-linker-Cub-GAL4-mNFkB-V5 bait for transfection | CMV-promoter, Gateway cassette, (GGGGS)2, Cub-GAL4(aa1-147)-mNFkB(aa364-550)-V5 |
| pCMV-Gateway-linker-mLexAVP16 | C-tagged-linker-Cub-mLexA-VP16 bait for transfection | CMV-promoter, Gateway cassette, (GGGGS)2, Cub-mLexA(aa1-202)-VP16(aa413-490)-V5 |
| pLV-CMV-Gateway-linker-GAL4-mNFkB-V5-PuroR | lentiviral C-tagged-linker-Cub-GAL4-mNFkB-V5 bait, puromycin marker | CMV-promoter, Gateway cassette, (GGGGS)2, Cub-GAL4(aa1-147)-mNFkB(aa364-550)-V5 |
| pLV-CMV-Gateway-linker-mLexAVP16-PuroR | lentiviral C-tagged-linker-Cub-mLexA-VP16 bait, puromycin marker | CMV-promoter, Gateway cassette, (GGGGS)2, Cub-mLexA(aa1-202)-VP16(aa413-490)-V5 |
| Lentiviral reporter constructs | | |
| pLV-5xGAL4-luciferase-hygroR | lentiviral luciferase reporter (5xGAL4UAS-binding sites), hygromycin marker | 5xGAL4UAS-TATAbox-firefly luciferase |
| pLV-5xGAL4-GFP-hygroR | lentiviral GFP reporter (5xGAL4UAS-binding sites), hygromycin marker | 5xGAL4UAS-TATAbox-eGFP |
| pLV-8xlexAops-luciferase-hygroR | lentiviral luciferase reporter (8xlexAops-binding sites), hygromycin marker | 8xlexAops-TATAbox-firefly luciferase |
| pLV-8xlexAops-GFP-hygroR | lentiviral GFP reporter (8xlexAops-binding sites), hygromycin marker | 8xlexAops-TATAbox-eGFP |
| Other expression vectors used | | |
| pCMV-Gateway-tripleFLAG | C-terminal tripleFLAG-tagging for transfection | CMV-Gateway cassette, 3xFLAG |

TABLE 5-continued

MaMTH vector backbones

| | Features | |
|---|---|---|
| pCMV-tripleFLAG-Gateway | N-terminal tripleFLAG-tagging for transfection | CMV-3xFLAG, Gateway cassette |

TABLE 6

Primers to generate all MaMTH reagents

Bait gap repair primers for cloning into pCCW-Ste-NotI/FspI

Cub-mLexA-GAL4

| | |
|---|---|
| mLexA-GAL4_F1 | aaggctaagaggtggtatgcacagatcagcttgcggccgcatgaaagcgttaacggccag |
| mLexA-GAL4_R1 | acaatgagctatcagcaatattcccactttgattaaaattgaattccagccagtcgccgt |
| mLexA-GAL4_F2 | tggcggttggggttattcgcaacggcgactggctggaattcaattttaatcaaagtggga |
| mLexA-GAL4_R2 | aatgcgccgctacagggcgcgtcgcgccattcgccattcattactcttttttgggtttg |

Cub-LexA-VP16

| | |
|---|---|
| LexA-VP16 | all primers same as mLexA-VP16 |
| mLexA-VP16_F1 | same as mLexA-GAL4_F1 |
| mLexA-VP16_R1 | agtggagctcgtcccccaggctgacatcggtcggggggcccagatcccgggaattccagcca gtcgccgt |
| mLexA-VP16_F2 | cggttggggttattcgcaacggcgactggctggaattcccggggatctgggccccccgaccgat gtcag |
| mLexA-VP16_R2 | aatgcgccgctacagggcgcgtcgcgccattcgccattcactacccaccgtactcgtcaa |

Cub-mLexA-mNFkB364-550

| | |
|---|---|
| mLexA-mNFkB-364-550_F1 | same as mLexA-GAL4_F1 |
| mLexA-mNFkB-364-550_R1 | ggtttgagatctgccctgatggtaacagcatgggggaaaaccagatcccgggaattccagccag tcgccgt |
| mLexA-mNFkB-364-550_F2 | ggcggttggggttattcgcaacggcgactggctggaattcccggggatctggttttcccccatgc tgttacca |
| mLexA-mNFkB-364-550_R2_V5tag | same as Gal4-mNFkB-364-550_R2_V5 |
| mLexA-mNFkB-364-550_R3 | same as Gal4-mNFkB-364-550_R3 |

Cub-mLexA-hNFkB451-549

| | |
|---|---|
| mLexA-hNFkB-451-549_F1 | same as mLexA-GAL4_F1 |
| mLexA-hNFkB-451-549_R1 | tgaacacagctgggtctgtgctgttgccaagcaaggcccccagatcccgaattccagccagtcg ccgtt |
| mLexA-hNFkB-451-549_F2 | gttattcgcaacggcgactggctggaattcgggatctgggggggccttgcttggcaaca |
| mLexA-hNFkB-451-549_R2 | same as Gal4-hNFkB-451-550_R2_V5tag |
| mLexA-hNFkB-451-549_R3 | same as Gal4-mNFkB-364-550_R3 |

Cub-mLexA-hNFkB521-549

| | |
|---|---|
| mLexA-hNFkB-521-549_F1 | same as mLexA-GAL4_F1 |
| mLexA-hNFkB-521-549_R1 | ggagaagtcttcatctcctgaaaggaggccattggggagccccggccagatcccgaattccagc cagtcgccgt |
| mLexA-hNFkB-521-549_F2 | ggcggttggggttattcgcaacggcgactggctggaattcgggatctggccgggggctccccaatgg cctcc |
| mLexA-hNFkB-521-549_R2 | same as Gal4-hNFkB-451-550_R2_V5tag |
| mLexA-hNFkB-521-549_R3 | same as Gal4-mNFkB-364-550_R3 |

Cub-mLexA-VP16-trimer

| | |
|---|---|
| mLexA-VP16-trimer_F1 | same as mLexA-GAL4_F1 |
| mLexA-VP16-trimer_R1 | caacatgtccagatcgaaatcgtctagcgcgtcgctacgggtgccgaattccagccagtc |
| mLexA-VP16-trimer_R2 | gctgcccagcatatccaagtcaaagtcatccaatgcatcactacccaacatgtccagatcgaaat |
| mLexA-VP16-trimer_R3 | actaccaagcatgtctagatcgaagtcgtcaagagcgtcgctgcccagcatatccaa |
| mLexA-VP16-trimer_R4_V5tag | ttacgtagaatcgagaccgaggagagggttagggataggcttaccactaccaagcatgtctagat |

Cub-mLexA-VP16-dimer

| | |
|---|---|
| mLexA-VP16-dimer_F1 | same as mLexA-GAL4_F1 |
| mLexA-VP16-dimer_R1 | actacccaacatgtccagatcgaaatcgtctagcgcgtcgctacgggtgccgaattccagccagtc gcc |
| mLexA-VP16-dimer_R2 | ttagctgctggtactacccagcatatccaagtcaaagtcatccaatgcatcactacccaacatgtcc aga |

TABLE 6 -continued

Primers to generate all MaMTH reagents

Cub-GAL4-mNFkB364-550

| | |
|---|---|
| Gal4-mNFkB-364-550_F1 | cttgtgctaaggctaagaggtggtatgcacagatcagctttgtcgacggtatcgataagcttgatgaagctactgtcttctat |
| Gal4-mNFkB-364-550_R1 | ggtttgagatctgccctgatggtaacagcatgggggaaaaaatcgatacagtcaactgtc |
| Gal4-mNFkB-364-550_F2 | gagtagtaacaaaggtcaaagacagttgactgtatcgattttttcccccatgctgttacc |
| Gal4-mNFkB-364-550_R2_V5 | ttacgtagaatcgagaccgaggagagggttagggataggcttacctccgccacctccggagctgatctgactcaaaa |
| Gal4-mNFkB-364-550_R3 | aatgcgccgctacagggcgcgtcgcgccattcgccattcattacgtagaatcgagaccga |

Cub-GAL4-mNFkB451-550

| | |
|---|---|
| Gal4-mNFkB-451-550_F1 | same as Gal4-NFkB-364-550_F1 |
| Gal4-mNFkB-451-550_R1 | tgaacactcctgggtctgtgctgttgccaagcaaggcccccaatcgatacagtcaactg |
| Gal4-mNFkB-451-550_F2 | agtagtaacaaaggtcaaagacagttgactgtatcgattggggccttgcttggcaacagca |
| Gal4-mNFkB-451-550_F1 | same as Gal4-NFkB-364-550_R2_V5 |
| Gal4-mNFkB-451-550_F1 | same as Gal4-NFkB-364-550_R3 |

Cub-GAL4-hNFkB451-549

| | |
|---|---|
| Gal4-hNFkB-451-549_F1 | same as Gal4-NFkB-364-550_F1 |
| Gal4-hNFkB-451-549_R1 | agctgggtctgtgctgttgccaagcaaggccccccagatcccaatcgatacagtcaactg |
| Gal4-hNFkB-451-549_F2 | aaaggtcaaagacagttgactgtatcgattgggatctggggggccttgcttggcaacagc |
| Gal4-hNFkB-451-549_R2_V5tag | ttacgtagaatcgagaccgaggagagggttagggataggcttaccggagctgatctgactcagcagg |
| Gal4-hNFkB-451-549_R3 | same as Gal4-mNFkB-364-550_R3 |

Cub-GAL4-hNFkB521-549

| | |
|---|---|
| Gal4-hNFkB-521-549_F1 | same as Gal4-NFkB-364-550_F1 |
| Gal4-hNFkB-521-549_R1 | cttcatctcctgaaaggaggccattggggagccccggccagatcccaatcgatacagtcaactgtc |
| Gal4-hNFkB-521-549_F2 | gtagtaacaaaggtcaaagacagttgactgtatcgattgggatctggccgggggctcccaatggcc |
| Gal4-hNFkB-521-549_R2_V5tag | same as Gal4-hNFkB-451-550_R2_V5tag |
| Gal4-hNFkB-521-549_R3 | same as Gal4-mNFkB-364-550_R3 |

Cloning of TFs into expression vectors

TF with GAL4-NfKB:

| | |
|---|---|
| TF_Gal4_F_Kpn1 | acgtaggtaccatgaagctactgtcttctatcgaacaag |
| TF_Gal4_R_XbaI_V5 | acgtatctagattacgtagaatcgagaccgaggag |

TF with mLexA or LexA

| | |
|---|---|
| TF_mLexA_F_KpnI | acgtaggtaccatgaaagcgttaacggccagg |
| TF_mLexAVP16_R_XbaI | acgtatctagactacccaccgtactcgtcaa |
| TF_mLexAGAL4_R_XbaI | acgta tctaga ttactctttttttgggtttggtgggta |
| TF_Gal4_R_XbaI_V5 | for TF9, 10 |
| TF_mLexA-VP16dimer_R_XbaI | acgta tctaga ttagctgctggtactacccagc |

Primers for cloning to create bait destination vectors

| | |
|---|---|
| linker_C-tagged_baits_XbaI | acgta tctaga ggtggcggtggctctggaggtggtgggtccatgtcggggggatccctcc |
| reverse_binding to V5_XbaI | acgtatctagattacgtagaatcgagaccgagg |
| reverse_binding to VP16_XbaI | acgtatctagactacccaccgtactcgtcaatt |
| linker_C-tagged_baits_EcoRV | ggtggcggtggctctggaggtggtgggtccatgtcggggggatccctcc |
| reverse_binding to V5_BstBI | acgtattcgaattacgtagaatcgagaccgagg |
| reverse_binding to VP16_BstBI | acgtattcgaactacccaccgtactcgtcaatt |

Creation of prey destination vectors (yNubi)

| | |
|---|---|
| N-taggedprey_F_KpnI | acgtaggtaccgccaccatgcagattttcgtcaagactttg |
| N-tagged_prey_R1_FLAGtag | cttgtcatcgtcatccttgtaatcgatgtcatgatctttataatcaccgtcatggtctttgtagtcagggatccttccttgtcttg |
| N-tagged_prey_R2_HindIII | acgtaaagcttggacccaccacctccagagccaccgccacccttgtcatcgtcatccttgtgactacaaagaccatgacggtgattataaagatcatgacatcgattacaaggatgacgatgacaa |
| C-tagged_prey_F1 | gatgcagattttcgtcaagac |
| C-tagged_prey_R1_XbaI | acgtatctagattagataccttccttgtcttgaatt |
| C-tagged_prey_F2_XbaI | acgtatctagaggtggcggtggctctggaggtggtgggtccgactacaaagaccatgacgg |

TABLE 6 -continued

Primers to generate all MaMTH reagents

Creation of prey destination vectors (hNubi)

| | |
|---|---|
| N-tagged_prey_F_KpnI | acgtaggtaccgccaccatgcagatcttcgtgaaaac |
| N-tagged_prey_R1_FLAG | cttgtcatcgtcatccttgtaatcgatgtcatgatctttataatcaccgtcatggtctttgtagtcgggaattaggccttccttatcctg |
| N-tagged_prey_R2_HindIII | same as N-tagged_prey_R2_HindIII |
| N-tagged_prey_F_NheI | acgtagctagcgccaccatgcagatcttcgt |
| N-tagged_prey_R2_EcoRV | ggacccaccacctccagagc |
| C-tagged_prey_F1 | gactacaaagaccatgacggtgattataaagatcatgacatcgattacaaggatgacgatgacaagatgcagatcttcgtgaaaaccc |
| C-tagged_prey_R1_XbaI | acgtatctagattagggaatgccttccttatcct |
| C-tagged_prey_F2_XbaI | acgtatctagaggtggcggtggctctggaggtggtgggtccgactacaaagaccatgacgg |
| C-tagged_prey_F1_EcoRV | ggtggcggtggctctggagg |
| C-tagged_prey_R1_BstBi | acgtattcgaattagggaatgccttccttatcctgg |

Mutagenesis primers Nub variants

| | |
|---|---|
| NubA_h_F | cccttaccggcaagaccgccacccttgaggtggagcc |
| NubA_h_R | ggctccacctcaagggtggcggtcttgccggtaaggg |
| NubV_h_F | cccttaccggcaagaccgtcacccttgaggtggagcc |
| NubV_h_R | ggctccacctcaagggtgacggtcttgccggtaaggg |
| NubG_h_F | cccttaccggcaagaccggcacccttgaggtggagcc |
| NubG_h_R | ggctccacctcaagggtgccggtcttgccggtaaggg |
| NubA_y_F | actttgaccggtaaaaccgccacattggaagttgaatct |
| NubA_y_R | agattcaacttccaatgtggcggttttaccggtcaaagt |
| NubV_y_F | actttgaccggtaaaaccgtcacattggaagttgaatct |
| NubV_y_R | agattcaacttccaatgtgacggttttaccggtcaaagt |
| NubG_y_F | actttgaccggtaaaaccggcacattggaagttgaatct |
| NubG_y_R | agattcaacttccaatgtgccggttttaccggtcaaagt |

Primers reporter generation generation of 5xGAL4UAS-luciferase-hygroR

| | |
|---|---|
| Hygro_F | acgtattcgaatcgagacaaatggcagtattcatc |
| Hygro_R | acgtaggtaccctattcctttgccctcggacg |
| pFR-Luc_F_SandI | acgtagggaccctcggagtactgtcctccgag |
| pFR-Luc_R_SalI | acgtagtcgacttacaatttggactttccgccc | generation of 8xlexAops-luciferase-hygroR

| | |
|---|---|
| lexAops_F_SandI | acgta gggaccc acatatccatatctaatcttacctcgactg |
| lexAops_R_BamHI | acgta ggatcc attatataccctctagagt atcgcattatcatccctcgacgt | generation of 5xGAL4UAS/8xlexAops-GFP-hygroR

| | |
|---|---|
| GFP_F_BamHI | acgta ggatcc ccgggtaccgagctcgaattccagcttggcattccggtactgttggtaaaatggtgagcaagggcgagg |
| GFP_R_BstBI | acgta ttcgaa ttacttgtacagctcgtccatgccg |

Gateway primers, common flanking primer regions

| | |
|---|---|
| GW_F | ggggacaagtttgtacaaaaaagcaggctta atg of gene |
| GW_R | ggggaccactttgtacaagaaagctgggta end of gene (reverse) |

Entry clone generation, Gateway primers

| | |
|---|---|
| EGFR_GW_F | ggggacaagtttgtacaaaaaagcaggctta gccacc atgcgaccctccgggacgg |
| EGFR_GW_R | ggggaccactttgtacaagaaagctgggta tgctccaataaattcactgctttg |
| ErbB2_GW_F | ggggacaagtttgtacaaaaaagcaggcttagccacc atggagctggcggccttg |
| ErbB2_GW_R | ggggaccactttgtacaagaaagctgggtacactggcacgtccagaccc |
| ErbB3_GW_F | ggggacaagtttgtacaaaaaagcaggcttaatgagggcgaacgacgctct |
| ErbB3_GW_R | ggggaccactttgtacaagaaagctgggtaccctggttcatgggcatgta |
| ErbB4_GW_F | ggggacaagtttgtacaaaaaagcaggcttagccacc atgaagccggcgacaggac |
| ErbB4_GW_R | ggggaccactttgtacaagaaagctgggtacaccacagtattccggtgtctg |
| GABBR1_GW_F | ggggacaagtttgtacaaaaaagcaggcttaatgggcccggggcccct |
| GABBR1_GW_R | ggggaccactttgtacaagaaagctgggtacttataaagcaaatgcactcgactcc |
| GABBR2_GW_F | ggggacaagtttgtacaaaaaagcaggcttaatgggcctcatgccgctc |
| GABBR2_GW_R | ggggaccactttgtacaagaaagctgggtacaggcccgagaccatgactc |
| TGFbR1_GW_F | ggggacaagtttgtacaaaaaagcaggcttaatggaggcggcggtcgctgc |
| TGFbR1_GW_R | ggggaccactttgtacaagaaagctgggtacattttgatgccttcctgttgactga |

TABLE 6 -continued

Primers to generate all MaMTH reagents

ErbB mutants

| | |
|---|---|
| ErbB4-R544W_F | ctctatgatggtgaattttgggagtttgagaatgg |
| ErbB4-R544W_R | ccattctcaaactcccaaaattcaccatcatagag |
| ERbB4-E872K_F | gactcttggaaggagataaaaaagagtacaatgctg |
| ErbB4-E872K_R | cagcattgtactctittttatctccttccaagagtc |
| ErbB4-E542K_F | gtaacctctatgatggtaaatttcgggagtttgag |
| ErbB4-E542K_R | ctcaaactcccgaaatttaccatcatagaggttac |
| EGFR-G719S_F | gatcaaagtgctgagctccggtgcgttc |
| EGFR-G719S_R | gaacgcaccggagctcagcactttgatc |
| EGFR-T790M_F | gtgcagctcatcatgcagctcatgcc |
| EGFR-T790M_R | ggcatgagctgcatgatgagctgcac |
| ErbB2_1139_A_F | ccagcctgaagctgtgaaccagccag |
| ErbB2_1139_A_R | ctggctggttcacagcttcaggctgg |
| EGFR_Y1092A_F | cagtgcctgaagccataaaccagtccg |
| EGFR_Y1092A_R | cggactggtttatggcttcaggcactg |
| EGFR_Y1138A_F | caaccccgaggctctcaacactgtc |
| EGFR_Y1138A_R | gacagtgttgagagcctcggggttg |
| EGFR_L858R_F | cacagatttgggcgggccaaactgctggg |
| EGFR_L858R_R | cccagcagtttggcccgcccaaaatctgtg |
| EGFR_855D_A_F | gtcaagatcacagcttttgggctggcc |
| EGFR_855D_A_R | ggccagcccaaaagctgtgatcttgac |
| EGFR_ex19del_F | gttaaaattcccgtcgctatcaagacatctccgaaagccaacaagg |
| EGFR_ex19del_R | ccttgttggctttcggagatgtcttgatagcgacgggaattttaac |
| ErbB3-Y1262A_F | gatgaagactatgaagctatgaatcggcaacg |
| ErbB3Y-1262A_R | cgttgccgattcatagcttcatagtcttcatc |
| ErbB3-Y1199A_F | gatgaggagtatgaagccatgaaccggagg |
| ErbB3-Y1199A_R | cctccggttcatggcttcatactcctcatc | b2AR-mutagenesis primers

| | |
|---|---|
| b2AR_F | atggggcaacccgggaacgg |
| GRK6_355, 356_F | ctatgggaatggctacgccggcaacggcaacacagggg |
| GRK6_355, 356_R | cccctgtgttgccgttgccggcgtagccattcccatag |
| GRK2_360_F | ctccagcaacggcaacgcaggggagcagagtggat |
| GRK2_360_R | atccactctgctcccctgcgttgccgttgctggag |
| GRK6_355, 356_GRK2_360_F | cgccggcaacggcaacgcaggggagcagagtggat |
| GRK6_355, 356_GRK2_360_R | atccactctgctcccctgcgttgccgttgccggcg |
| GRK2_364_F | caacgcaggggacagggtggatatcacgtggaac |
| GRK2_364_F | gttccacgtgatatccaccctgctcccctgcgttg |
| GRK2_396, 401 | tgcatcaatgttatcgccaggcacagtaccttgatggc |
| GRK2_407, 411 | cagcagtgcgtcatttgtaccacaattcctcccttgtgcatcaatg |

Gap repair primers to put b2AR-mutants into pCCW-Ste-NotI/FspI

| | |
|---|---|
| GR_1_F | gtccacttacatcttgtgctaaggctaagaggtggtatggccaccatggggcaacccgggaacgg |
| GR_1_R | acagcagtttattttctttctcctgttccacgtgatatccaccctgctcccctgcgttgc |
| GR_2_F | gaatggctacgccggcaacggcaacgcaggggagcagggtggatatcacgtggaacaggag |
| GR_2_R | cgcgcttaatgcgccgctacagggcgcgtcgcgccattcgcagcagtgcgtcatttgtaccac |

Gateway primers for cloning b2AR-mutants into entry clones

| | |
|---|---|
| b2AR-Mutants_GW_F | ggggacaagtttgtacaaaaaagcaggctta gccaccatggggcaacccgggaacgg |
| b2AR-Mutants_GW_R | ggggaccactttgtacaagaaagctgggta cagcagtgagtcatttgtactacaattcc |
| b2AR-Mutants_GW_R+GRK6 | ggggaccactttgtacaagaaagctgggtacagcagtgcgtcatttgtaccac |

TABLE 7

List of antibodies rabbit anti-ERK1/2, p44/42 MAPK #45955, Cell Sigaling
rabbit anti-phospho-ERK1/2, p44/42 MAPK (T202/Y204) #4370S, Cell Sigaling
mouse anti-GFP, JL-8, Living Colors
rabbit anti-AKT, #9272, Cell Signaling
rabbit anti-phospho-AKT (Ser473) #4058, Cell Signaling
rabbit anti-EGFR (1005), sc-03, Santa Cruz
rabbit anti-phospho-EGFR (pTyr 1068), LS-C6640, Life Span
rabbit anti-VP16 V4388, Sigma
mouse anti-FLAG M2, F3165 Sigma
mouse anti-tubulin sc-8035, Santa Cruz
mouse anti-V5 R960-25, Invitrogen
anti-mouse IgG, HRP-linked (sheep) NXA931 GE Healthcare
anti-rabbit IgG, HRP-linked (donkey) NA934V GE Healthcare The subject matter has been described with reference to particular embodiments. However, it will be readily apparent to those skilled in the art that it is possible other embodiments of described above. Nevertheless, it will be understood that various modifications to the described embodiments may be made without departing from the spirit and scope of the claimed invention. Accordingly, the scope of the invention should be determined by the following claims and their legal equivalents.

REFERENCES

1. Stevens, T. J. & Arkin, I. T. Do more complex organisms have a greater proportion of membrane proteins in their genomes? Proteins 39, 417-420 (2000).
2. Overington, J. P., Al-Lazikani, B. & Hopkins, A. L. How many drug targets are there? Nat Rev Drug Discov 5, 993-996 (2006).
3. Fields, S. & Song, O. A novel genetic system to detect protein-protein interactions. Nature 340, 245-246 (1989).
4. Lievens, S., Lemmens, I. & Tavernier, J. Mammalian two-hybrids come of age. Trends Biochem Sci 34, 579-588 (2009).
5. Barrios-Rodiles, M. et al. High-throughput mapping of a dynamic signaling network in mammalian cells. Science 307, 1621-1625 (2005).
6. Taipale, M., Jarosz, D. F. & Lindquist, S. HSP90 at the hub of protein homeostasis: emerging mechanistic insights. Nat Rev Mol Cell Biol 11, 515-528.
7. Kerppola, T. K. Visualization of molecular interactions by fluorescence complementation. Nat Rev Mol Cell Biol 7, 449-456 (2006).
8. Michnick, S. W., Ear, P. H., Manderson, E. N., Remy, I. & Stefan, E. Universal strategies in research and drug discovery based on protein-fragment complementation assays. Nat Rev Drug Discov 6, 569-582 (2007).
9. Vidi, P. A. & Watts, V. J. Fluorescent and bioluminescent protein-fragment complementation assays in the study of G protein-coupled receptor oligomerization and signaling. Mol Pharmacol 75, 733-739 (2009).
10. Ciruela, F. Fluorescence-based methods in the study of protein-protein interactions in living cells. Curr Opin Biotechnol 19, 338-343 (2008).
11. Lemmens, I., Lievens, S. & Tavernier, J. MAPPIT: a versatile tool to study cytokine receptor signalling. Biochem Soc Trans 36, 1448-1451 (2008).
12. Johnsson, N. & Varshavsky, A. Split ubiquitin as a sensor of protein interactions in vivo. Proc Natl Acad Sci USA 91, 10340-10344 (1994).
13. Stagljar, I., Korostensky, C., Johnsson, N. & to Heesen, S. A genetic system based on split-ubiquitin for the analysis of interactions between membrane proteins in vivo. Proc Natl Acad Sci USA 95, 5187-5192 (1998).
14. Rojo-Niersbach, E., Morley, D., Heck, S. & Lehming, N. A new method for the selection of protein interactions in mammalian cells. Biochem J 348 Pt 3, 585-590 (2000).
15. da Cunha Santos, G., Shepherd, F. A. & Tsao, M. S. EGFR mutations and lung cancer. Annu Rev Pathol 6, 49-69.
16. Remy, I. & Michnick, S. W. Application of protein-fragment complementation assays in cell biology. Biotechniques 42, 137, 139, 141 passim (2007).
17. Snider, J. et al. Detecting interactions with membrane proteins using a membrane two-hybrid assay in yeast. Nat Protoc 5, 1281-1293.
18. Ballard, D. W. et al. The 65-kDa subunit of human NF-kappa B functions as a potent transcriptional activator and a target for v-Rel-mediated repression. Proc Natl Acad Sci USA 89, 1875-1879 (1992).
19. Baron, U., Gossen, M. & Bujard, H. Tetracycline-controlled transcription in eukaryotes: novel transactivators with graded transactivation potential. Nucleic Acids Res 25, 2723-2729 (1997).
20. Corton, J. C., Moreno, E. & Johnston, S. A. Alterations in the GAL4 DNA-binding domain can affect transcriptional activation independent of DNA binding. J Biol Chem 273, 13776-13780 (1998).
21. Emami, K. H. & Carey, M. A synergistic increase in potency of a multimerized VP16 transcriptional activation domain. Embo J 11, 5005-5012 (1992).
22. Ptashne, M. & Gann, A. A. Activators and targets. Nature 346, 329-331 (1990).
23. Ruben, S. M., Narayanan, R., Klement, J. F., Chen, C. H. & Rosen, C. A. Functional characterization of the NF-kappa B p65 transcriptional activator and an alternatively spliced derivative. Mol Cell Biol 12, 444-454 (1992).
24. Sadowski, I., Ma, J., Triezenberg, S. & Ptashne, M. GAL4-VP16 is an unusually potent transcriptional activator. Nature 335, 563-564 (1988).
25. Schmitz, M. L. et al. Structural and functional analysis of the NF-kappa B p65 C terminus. An acidic and modular transactivation domain with the potential to adopt an alpha-helical conformation. J Biol Chem 269, 25613-25620 (1994).
26. Seipel, K., Georgiev, O. & Schaffner, W. Different activation domains stimulate transcription from remote ('enhancer') and proximal ('promoter') positions. Embo J 11, 4961-4968 (1992).
27. Dunkler, A., Muller, J. & Johnsson, N. Detecting protein-protein interactions with the Split-Ubiquitin sensor. Methods Mol Biol 786, 115-130.
28. Johnsson, N. & Varshavsky, A. Ubiquitin-assisted dissection of protein transport across membranes. Embo J 13, 2686-2698 (1994).
29. Nijman, S. M. et al. A genomic and functional inventory of deubiquitinating enzymes. Cell 123, 773-786 (2005).
30. Wilkinson, K. D. DUBs at a glance. J Cell Sci 122, 2325-2329 (2009).
31. Rhee, Y., Gurel, F., Gafni, Y., Dingwall, C. & Citovsky, V. A genetic system for detection of protein nuclear import and export. Nat Biotechnol 18, 433-437 (2000).
32. Moore, C. A., Milano, S. K. & Benovic, J. L. Regulation of receptor trafficking by GRKs and arrestins. Annu Rev Physiol 69, 451-482 (2007).
33. Yarden, Y. & Sliwkowski, M. X. Untangling the ErbB signalling network. Nat Rev Mol Cell Biol 2, 127-137 (2001).
34. Kolch, W. & Pitt, A. Functional proteomics to dissect tyrosine kinase signalling pathways in cancer. Nat Rev Cancer 10, 618-629.
35. Prickett, T. D. et al. Analysis of the tyrosine kinome in melanoma reveals recurrent mutations in ERBB4. Nat Genet 41, 1127-1132 (2009).
36. Pines, G., Kostler, W. J. & Yarden, Y. Oncogenic mutant forms of EGFR: lessons in signal transduction and targets for cancer therapy. FEBS Lett 584, 2699-2706.
37. Sun, J. M. et al. The different efficacy of gefitinib or erlotinib according to epidermal growth factor receptor exon 19 and exon 21 mutations in Korean non-small cell lung cancer patients. J Cancer Res Clin Oncol 137, 687-694.
38. Bublil, E. M. & Yarden, Y. The EGF receptor family: spearheading a merger of signaling and therapeutics. Curr Opin Cell Biol 19, 124-134 (2007).
39. Favoni, R. E. & Alama, A. Preclinical strategies targeted at non-small-cell lung cancer signalling pathways with striking translational fallout. Drug Discov Today 18, 11-24.
40. Carey, K. D. et al. Kinetic analysis of epidermal growth factor receptor somatic mutant proteins shows increased sensitivity to the epidermal growth factor receptor tyrosine kinase inhibitor, erlotinib. Cancer Res 66, 8163-8171 (2006).
41. Schulze, W. X., Deng, L. & Mann, M. Phosphotyrosine interactome of the ErbB-receptor kinase family. Mol Syst Biol 1, 2005 0008 (2005).
42. Jemal, A. et al. Cancer statistics, 2009. CA Cancer J Clin 59, 225-249 (2009).
43. Pawson, T. Regulation and targets of receptor tyrosine kinases. Eur J Cancer 38 Suppl 5, S3-10 (2002).
44. Goh, K. I. et al. The human disease network. Proc Natl Acad Sci USA 104, 8685-8690 (2007).
45. Sriram, G. & Birge, R. B. Emerging roles for crk in human cancer. Genes Cancer 1, 1132-1139.
46. Jan, C. I. et al. Tid1, CHIP and ErbB2 interactions and their prognostic implications for breast cancer patients. J Pathol 225, 424-437.
47. Kosaka, T., Yamaki, E., Mogi, A. & Kuwano, H. Mechanisms of resistance to EGFR TKIs and development of a new generation of drugs in non-small-cell lung cancer. J Biomed Biotechnol 2011, 165214.
48. Zhang, J. et al. Analysis of bypass signaling in EGFR pathway and profiling of bypass genes for predicting response to anticancer EGFR tyrosine kinase inhibitors. Mol Biosyst 8, 2645-2656.
49. Yang, X. et al. A public genome-scale lentiviral expression library of human ORFs. Nat Methods 8, 659-661.
50. Lemercier, C. et al. mHDA1/HDAC5 histone deacetylase interacts with and represses MEF2A transcriptional activity. J Biol Chem 275, 15594-15599 (2000).
51. Gietz, R. D. & Woods, R. A. Transformation of yeast by lithium acetate/single-stranded carrier DNA/polyethylene glycol method. Methods Enzymol 350, 87-96 (2002).

The following claims are provided to add additional clarity to this disclosure. Future applications claiming priority to this application may or may not include the following claims, and may include claims broader, narrower, or entirely different from the following claims.

Therefore what is claimed is:

1. A method for detecting the interaction between a first membrane protein or part thereof and a second membrane or soluble protein or part thereof comprising: (a) providing a host mammalian cell including at least one detectable gene (reporter gene) having a binding site for a transcription factor, such that the detectable gene expresses a detectable product; (b) expressing in the host mammalian cell the first protein or part thereof, the first protein or part thereof being attached through a suitable first linker to a C-terminal sub-domain of a human ubiquitin (Cub) and a transcription factor; (c) expressing in the host mammalian cell the second protein or part thereof, the second protein or part thereof being attached to a wild-type N-terminal sub-domain of the human ubiquitin protein (Nub) through a second suitable linker; and (d) determining whether the detectable product is detected, detection of the detectable product being indicative that the first protein and the second protein interact, wherein the first linker and the second linker is a peptide comprising the amino acid sequence (GGGGS)n, wherein "n" is an integer equal to or larger than 1, and wherein the detectable gene includes a fluorescent reporter gene and the detectable product is luciferase.

2. A method for quantitatively measuring strength and affinity of an interaction between a first membrane protein or part thereof and a second membrane or soluble protein or part thereof comprising: (a) providing a host mammalian cell including a detectable gene (reporter gene) having a binding site for a transcription factor, such that the detectable gene expresses a measurable detectable product when the detectable gene is transcriptionally activated; (b) expressing in the host mammalian cell the first protein or part thereof, the first protein or part thereof being attached through a suitable first linker to a C-terminal sub-domain of a human ubiquitin (Cub) and the transcription factor; (c) expressing in the host mammalian cell the second protein or part thereof, the second protein or part thereof being attached to a wild-type N-terminal sub-domain of the human ubiquitin protein (Nub) through a second suitable linker; and (d) measuring an expression output of the detectable product as a measure of the amount of interaction between the first and the second proteins, wherein the first linker and the second linker is a peptide comprising the amino acid sequence (GGGGS)n, wherein "n" is an integer equal to or larger than 1, and wherein the detectable gene includes a fluorescent reporter gene and the detectable product is luciferase.

3. The method of claim 2, wherein the expression output of the detectable product is emission of light and step (d) comprises measuring the resulting light emission as a measure of the amount of interaction between the first and the second proteins.

4. The method of claim 1, wherein step (b) comprises introducing into the mammalian host cell as part of a bait vector, a first gene under the control of a promoter, said first gene coding inter alia for the first protein or part thereof which gene is attached to the DNA-sequence of a first module encoding inter alia the Cub, the first suitable linker between the first protein and the Cub and the transcription factor.

5. The method of claim 1, wherein step (c) comprises introducing into the mammalian host cell, as part of a prey vector, a second gene under the control of a promoter, the second gene coding inter alia for the second protein or part thereof which gene is attached to the DNA sequence of a second module encoding inter alia the Nub and the second suitable linker between the second protein and the Nub.

6. The method of claim 1, wherein the first and second suitable linkers are substantially identical.

7. The method of claim 1, wherein the first and second proteins or parts thereof are mammalian proteins.

8. The method of claim 1, wherein the bait vector is maintained episomally in the host mammalian cell or is integrated into the genome of the host mammalian cell.

9. The method of claim 1, wherein the prey vector is maintained episomally in the host mammalian cell or is integrated into the genome of the host mammalian cell.

10. The method of claim 1, wherein "n" is an integer equal to or larger than 2.

11. The method of claim 1, wherein the transcription factor is a chimeric transcription factor selected from mLexA-VP16 and Gal4-mouseNFkB.

12. A kit of reagents for quantitatively measuring strength and affinity binding between a first membrane protein or part thereof and a second membrane or soluble protein or part thereof comprising:
   (a) a host cell including at least one detectable gene (reporter gene) having a binding site for a transcription factor, such that the detectable gene expresses a detectable product when the detectable gene is transcriptionally activated, the at least one detectable gene including a fluorescent reporter gene and the detectable product is luciferase;
   (b) a first vector (bait) comprising a first site that can receive a first nucleic acid coding for the first protein or part thereof such that when the first nucleic acid is inserted it becomes attached to the DNA sequence of a first module encoding inter alia a C-terminal sub-domain of a human ubiquitin protein (Cub), a first suitable linker between the first protein and the Cub, the first module further comprising a nucleic acid for the transcription factor, and a promoter, the first linker being a peptide comprising the amino acid sequence (GGGGS)n, wherein "n" is an integer equal to or larger than 1;

(c) a second vector (prey) comprising a second site that can receive a second nucleic acid coding for the second protein or part thereof such that when the second nucleic acid is inserted it becomes attached to the DNA sequence of a second module encoding inter alia a wild-type N-terminal sub-domain of the human ubiquitin protein (Nub) and a second suitable linker between the second protein and the Nub, wherein the second module further comprises a promoter, the second linker being a peptide comprising the amino acid sequence (GGGGS)n, wherein "n" is an integer equal to or larger than 1.

13. The kit of claim 12, wherein the first and second suitable linkers are substantially identical.

14. The kit according to claim 12, wherein the second protein or part thereof is a membrane protein.

15. The kit according to claim 12, wherein the bait vector is maintained episomally in the host mammalian cell or is integrated into the genome of the host mammalian cell.

16. The kit according to claim 12, wherein the prey vector is maintained episomally in the host mammalian cell or is integrated into the genome of the host mammalian cell.

17. The kit according to claim 12, wherein "n" is an integer equal to or larger than 2.

18. The kit according to claim 12, wherein the transcription factor is a chimeric transcription factor selected from mLexA-VP16 and Ga14-mouseNFkB.

19. The kit according to claim 12, wherein the first membrane protein or part thereof and the second membrane or soluble protein or part thereof are mammalian proteins.

20. A method of identifying a potentially pharmaceutically active agent comprising using the kit of claim 12 to screen an agent for the ability to interfere with protein-protein interaction, whereupon the ability to interfere with protein-protein interaction is indicative of the agent being potentially pharmaceutically active.

21. A method for providing a compound that can interfere with protein-protein interaction, the method comprising: (a) providing a mammalian host cell having the prey vector and the bait vector described in claim 4, the first and second proteins or parts therefore being selected such that they are known to interact when expressed; (b) incubating the mammalian host cell in the presence and absence of the compound to be tested; (c) measuring the difference in reporter gene expression between the incubation containing the compound to be tested and the incubation free of the compound to be tested; and optionally (d) purifying or synthesizing the compound that can interfere with protein-protein interaction.

22. The kit according to claim 12, wherein the kit is used in a screening process for identifying pharmaceutical drugs.

23. The kit according to claim 12, wherein the kit is used in screening the phosphorylation status of the first or second proteins.

* * * * *